US011224361B2

(12) United States Patent
Garai et al.

(10) Patent No.: US 11,224,361 B2
(45) Date of Patent: Jan. 18, 2022

(54) FLEXIBLE PHYSIOLOGICAL CHARACTERISTIC SENSOR ASSEMBLY

(71) Applicant: MEDTRONIC MINIMED, INC., Northridge, CA (US)

(72) Inventors: Ellis Garai, Studio City, CA (US); David Choy, San Gabriel, CA (US); Robert C. Mucic, Glendale, CA (US); David C. Antonio, Montrose, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 234 days.

(21) Appl. No.: 16/392,528

(22) Filed: Apr. 23, 2019

(65) Prior Publication Data

US 2020/0337608 A1 Oct. 29, 2020

(51) Int. Cl.
*A61B 5/145* (2006.01)
*A61B 5/00* (2006.01)

(52) U.S. Cl.
CPC .......... *A61B 5/14532* (2013.01); *A61B 5/688* (2013.01); *A61B 5/6833* (2013.01);
(Continued)

(58) Field of Classification Search
CPC ............ A61B 5/14532; A61B 2560/02; A61B 2560/0209; A61B 2560/029; A61B 2560/0325; A61B 2560/0366; A61B 2562/242; A61B 2564/24; A61B 5/145–14503; A61B 5/1451; A61B 5/14546; A61B 5/1468–14735; A61B 5/11486–4865; A61B 5/6833; A61B 5/6848; A61B 2560/063; A61B 2560/0204–0209; A61B 2560/0412; A61M 5/158; A61M 5/20; A61M 5/2003;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| WO | WO-2011119896 A1 * | 9/2011 | ........... A61B 5/1513 |
| WO | WO-2012118872 A2 * | 9/2012 | ........... A61B 5/6849 |

*Primary Examiner* — Eric F Winakur
*Assistant Examiner* — Alice Ling Zou
(74) *Attorney, Agent, or Firm* — Lorenz & Kopf, LLP

(57) ABSTRACT

A sensor introducer for a physiological characteristic sensor assembly includes a sensor introducer body that includes an outer housing that defines an opening to receive the physiological characteristic sensor assembly and an inner housing surrounded by the outer housing. The sensor introducer includes a cradle movable relative to the inner housing from a first position to a second position to deploy the physiological characteristic sensor assembly. The cradle has a cradle flange to receive the physiological characteristic sensor assembly and a cradle body that receives a needle assembly. The cradle body includes at least one locking projection that engages the inner housing to inhibit the movement of the cradle relative to the inner housing in the first position and the at least one locking projection is movable relative to the inner housing to enable the cradle to move from the first position to the second position.

13 Claims, 63 Drawing Sheets

(52) U.S. Cl.
CPC .......... *A61B 5/6848* (2013.01); *A61B 5/0015* (2013.01); *A61B 5/6804* (2013.01); *A61B 2562/164* (2013.01)

(58) Field of Classification Search
CPC ...... A61M 5/3293; A61M 5/329; A61M 5/34; A61M 5/344; A61M 5/345; A61M 5/346; A61M 5/347; A61M 5/348; A61M 2005/1585; A61M 2005/202; A61M 2005/2006; A61M 2005/2026; A61M 2005/2073; A61M 2005/208
See application file for complete search history.

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,892,085 | B2 | 5/2005 | McIvor et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,468,033 | B2 | 12/2008 | Van Antwerp et al. |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 8,979,808 | B1* | 3/2015 | Chong ............... A61M 5/31511 604/246 |
| 9,295,786 | B2 | 3/2016 | Gottlieb et al. |
| 2007/0123819 | A1 | 5/2007 | Mernoe et al. |
| 2009/0299301 | A1 | 12/2009 | Gottlieb et al. |
| 2010/0160861 | A1 | 6/2010 | Causey, III et al. |
| 2010/0217105 | A1* | 8/2010 | Yodfat ............... A61B 5/14532 600/365 |
| 2012/0078071 | A1* | 3/2012 | Bohm ................ A61B 5/14532 600/345 |
| 2015/0174319 | A1 | 6/2015 | Rieck |
| 2016/0331284 | A1* | 11/2016 | Pace .................. A61B 5/14532 |
| 2017/0000359 | A1* | 1/2017 | Kohli .................. A61B 5/0022 |
| 2017/0027514 | A1* | 2/2017 | Biederman .......... A61B 5/1451 |
| 2017/0188912 | A1* | 7/2017 | Halac ................. A61B 5/14865 |
| 2017/0290533 | A1* | 10/2017 | Antonio ............. A61B 5/6832 |
| 2017/0290546 | A1* | 10/2017 | Antonio ............. A61B 17/3468 |

* cited by examiner

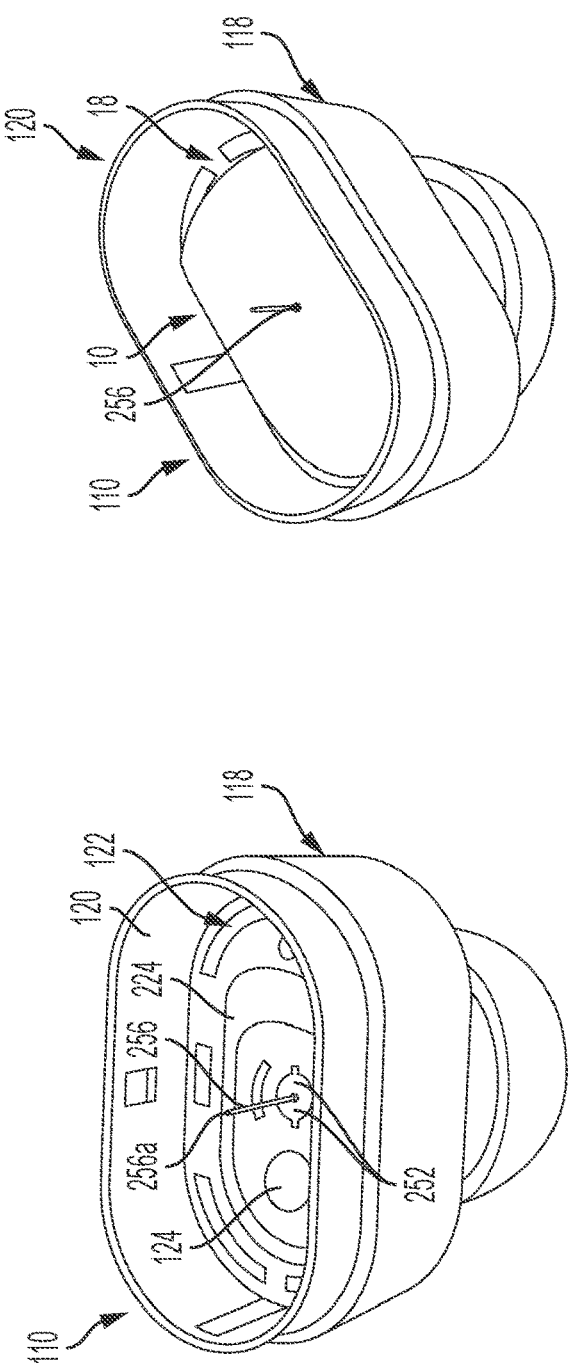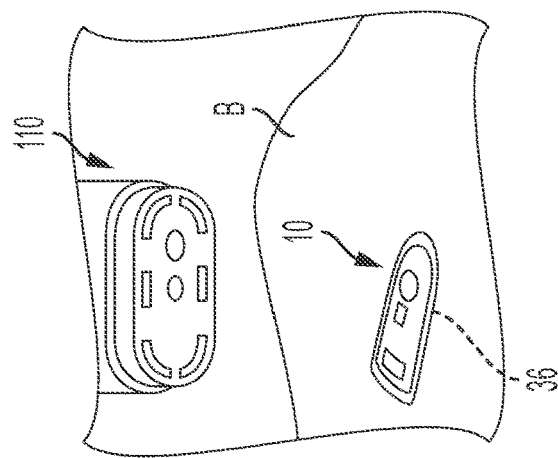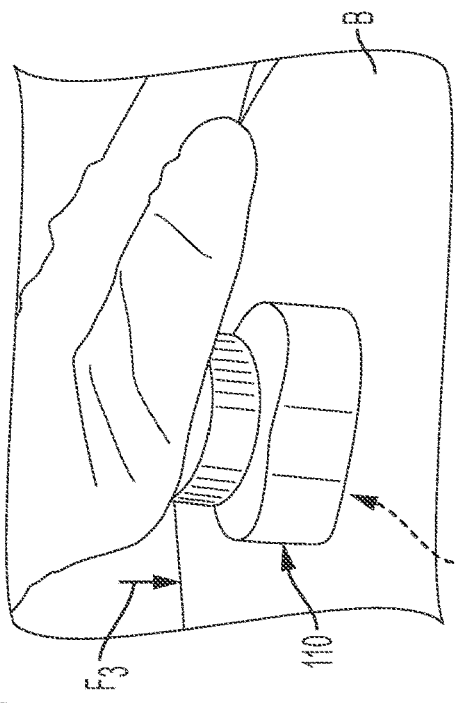

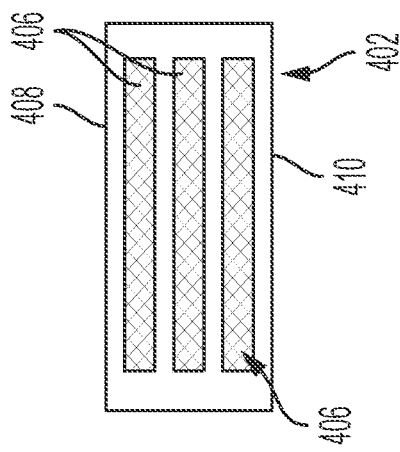
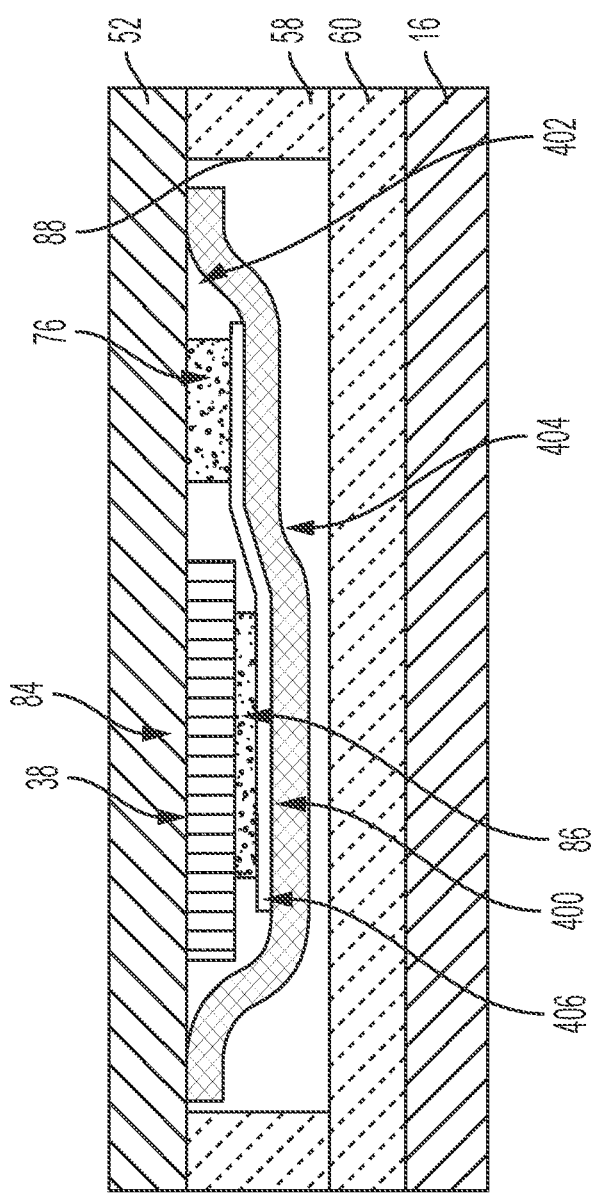
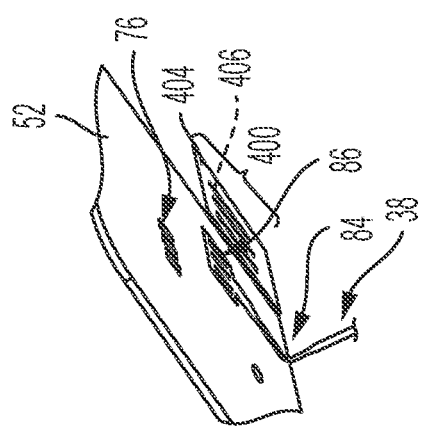

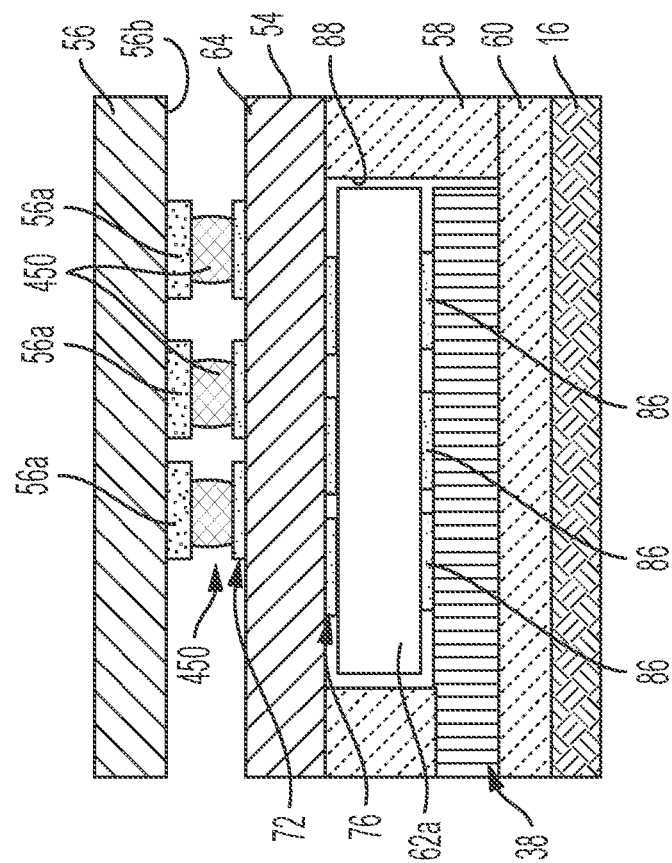
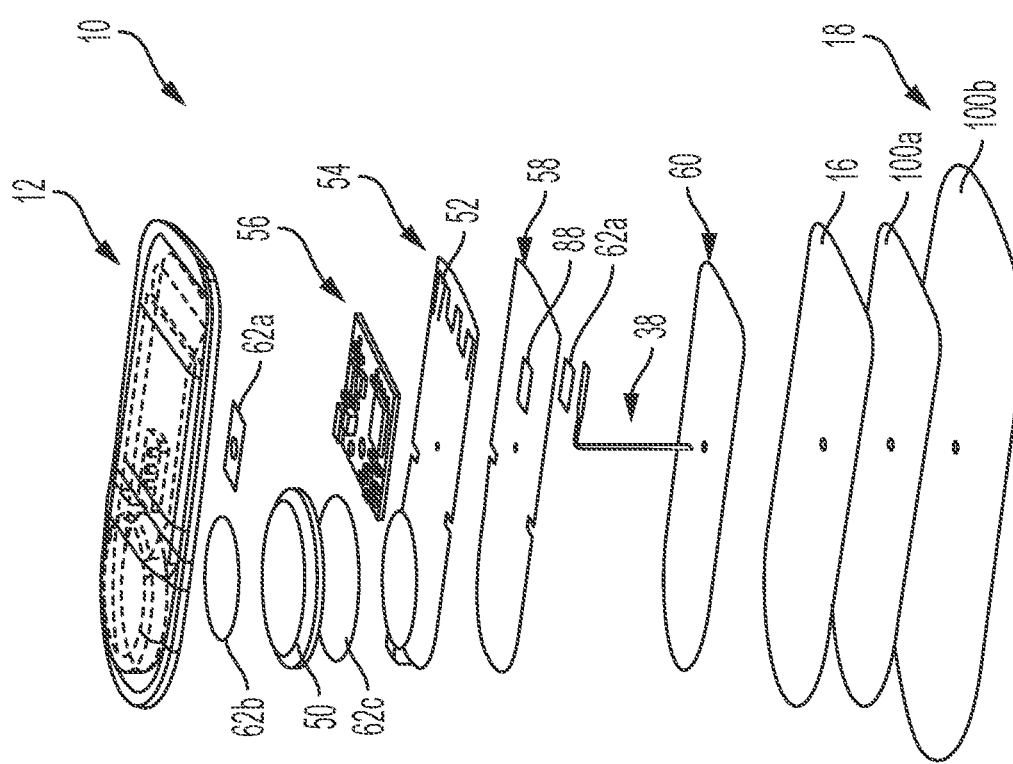
FIG. 27A
FIG. 27

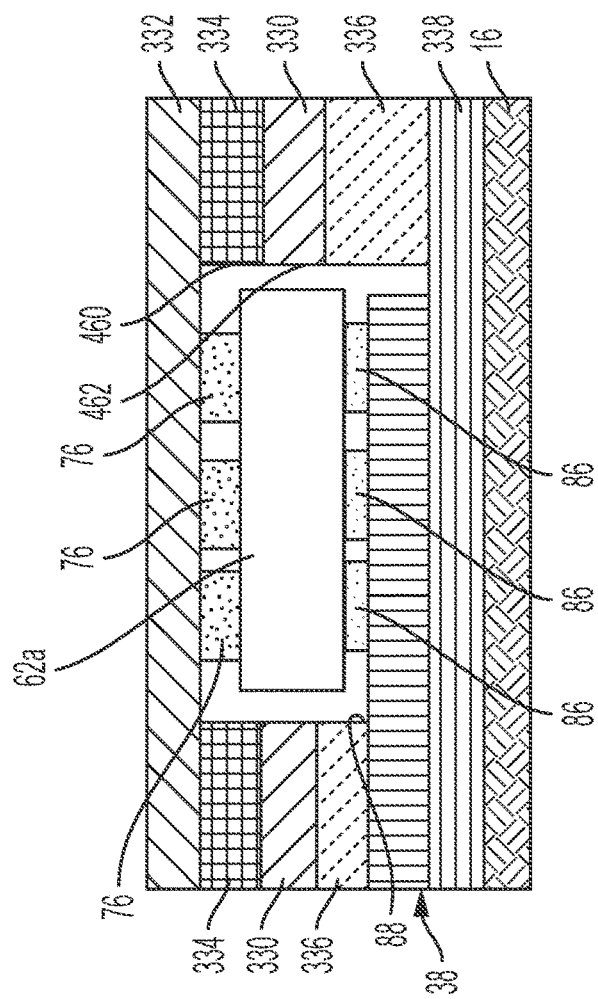
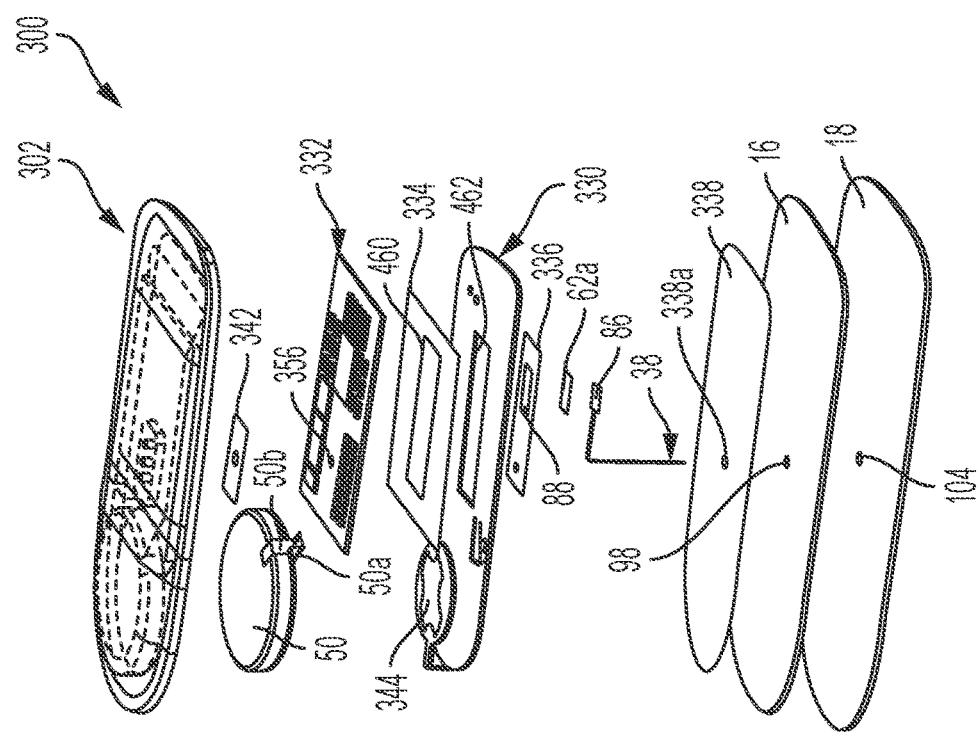
FIG. 28A
FIG. 28

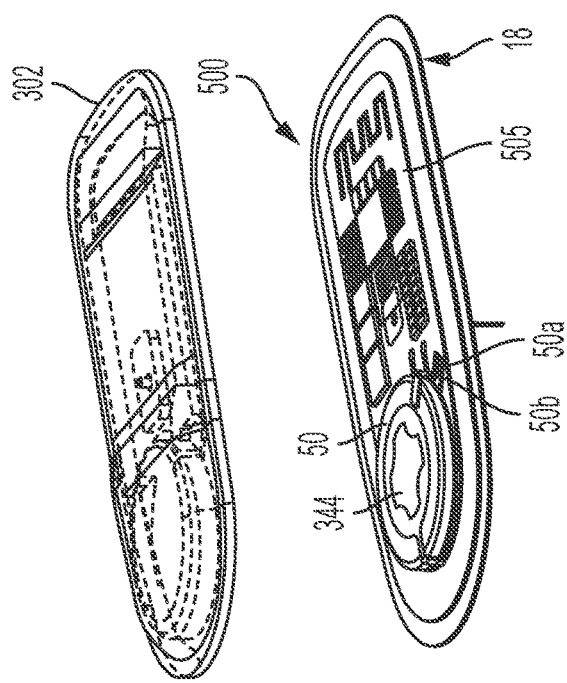
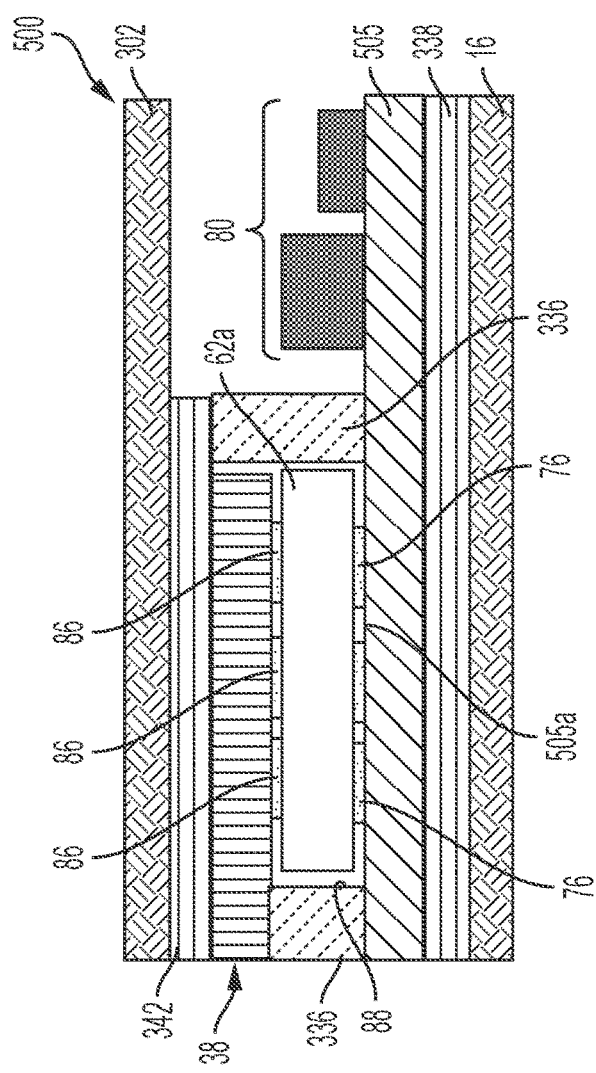
FIG. 29
FIG. 29A

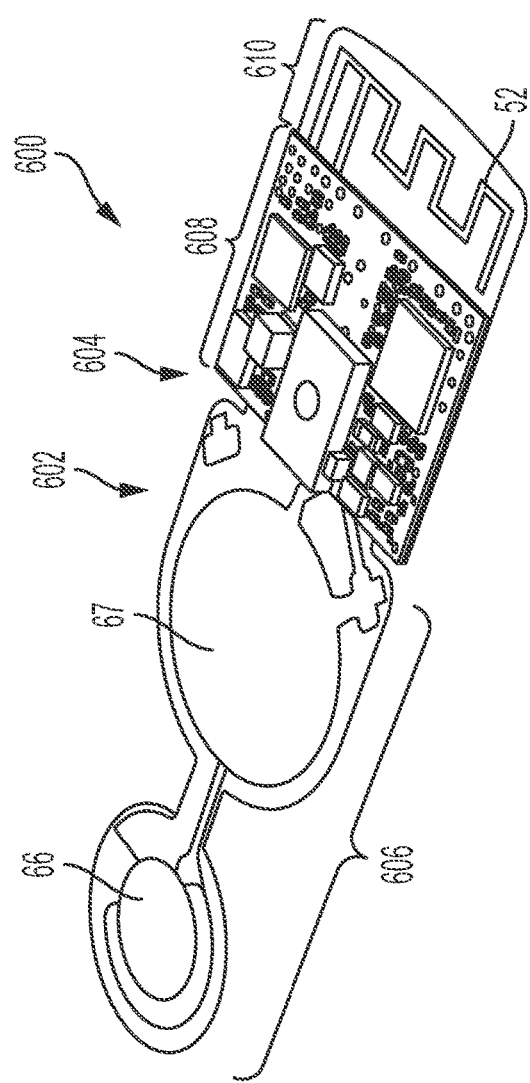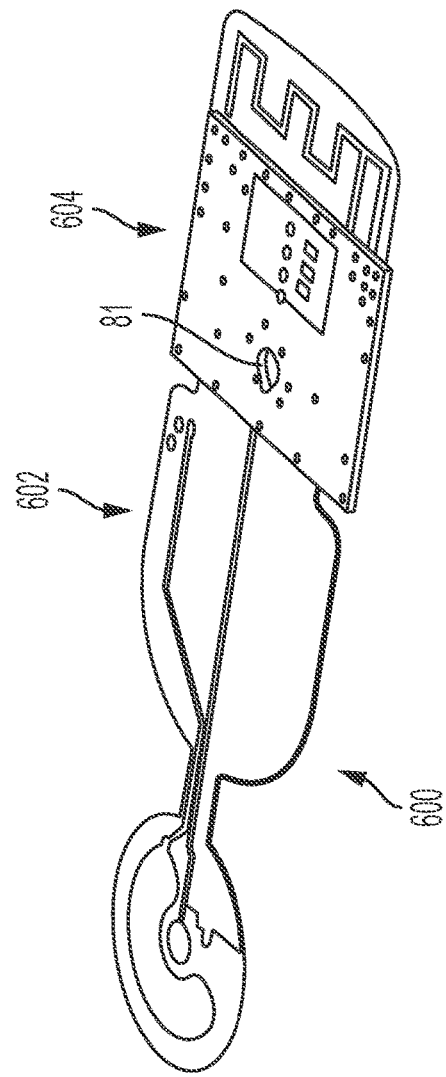
FIG. 33
FIG. 33A

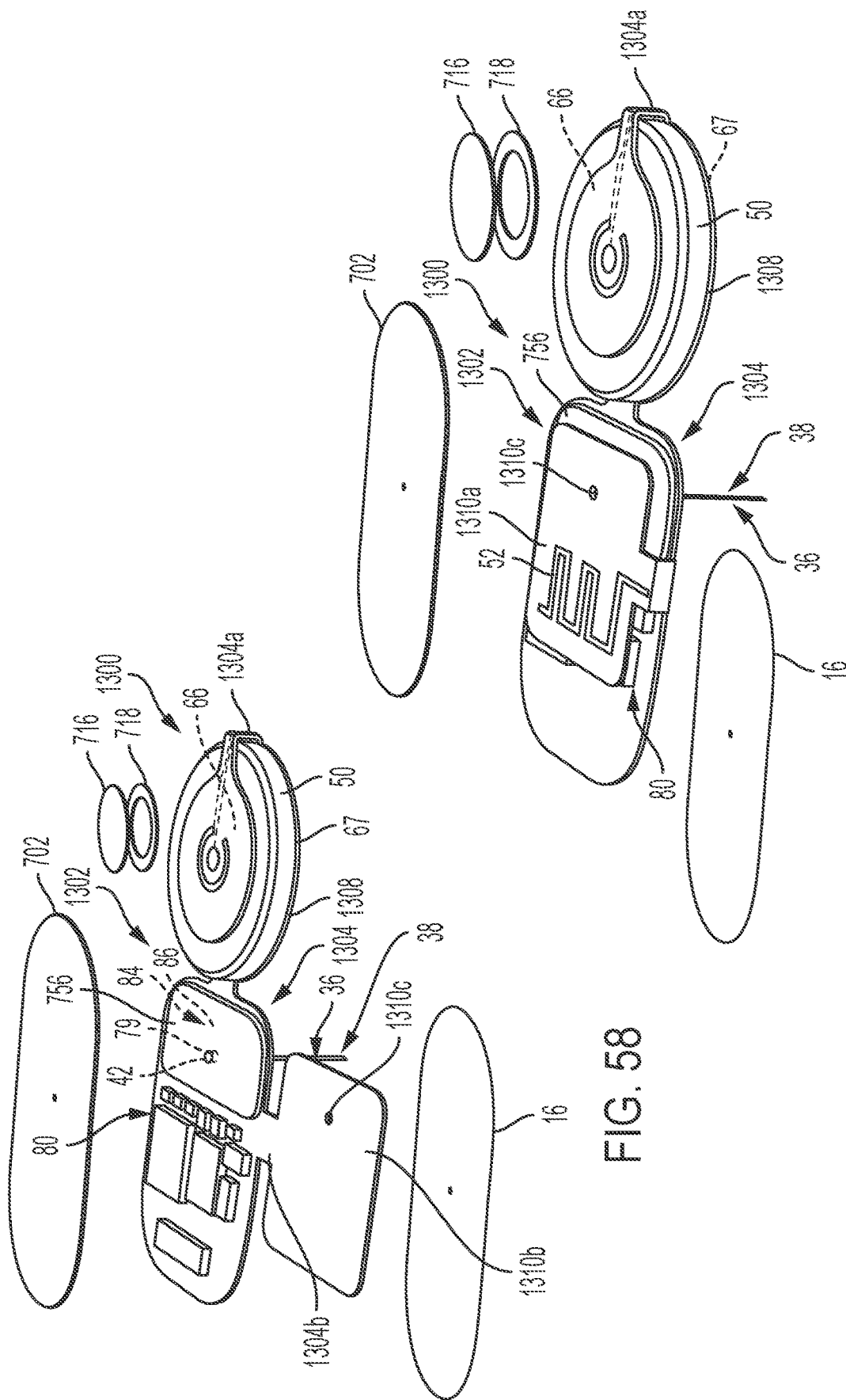

FLEXIBLE PHYSIOLOGICAL CHARACTERISTIC SENSOR ASSEMBLY

FIELD

Embodiments of the subject matter described herein relate generally to medical devices, such as a physiological characteristic sensor assembly. More particularly, embodiments of the subject matter relate to a flexible physiological characteristic sensor assembly for coupling to a user having at least one physiological characteristic sensor that observes a physiological characteristic of the user. In various embodiments, the physiological characteristic sensor is a glucose sensor.

BACKGROUND

Sensors may be employed in the treatment of or monitoring of various medical conditions. In one example, electrochemical sensors are used to test analyte levels in patients or users. More specifically, sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

Generally, sensors for monitoring BG levels are coupled to the body of the user over a period of time. In most instances, the sensors for monitoring BG levels are coupled to a continuous glucose monitor (CGM), which has associated electronics that process the sensor signals, monitor BG levels and may transmit the BG levels to a remote device, such as an infusion device. The housing of the CGM is a rigid structure. The rigid nature of the housing for the CGM may tend to transfer moment forces from one end of the device to the other, which may lead to a peeling of an adhesive that couples the sensor for monitoring BG levels and the CGM to the body, or may lead to a partial removal of the distal segment portion of the sensor from the subcutaneous tissue, both of which may impact the sensor readings. Moreover, the rigid nature of the CGM may be uncomfortable to the user, as the rigid nature of the CGM does not enable the CGM to conform to the user's anatomy.

Accordingly, it is desirable to provide a physiological characteristic sensor assembly, such as a blood glucose sensor, that is flexible to reduce the transfer of forces in order to maintain the sensor's signal stability and accuracy. Further, it is desirable to provide a physiological characteristic sensor assembly, such as a blood glucose sensor, that is flexible to conform the user's anatomy, and thus, improve user comfort during use. Furthermore, other desirable features and characteristics will become apparent from the subsequent detailed description and the appended claims, taken in conjunction with the accompanying drawings and the foregoing technical field and background.

SUMMARY

The techniques of this disclosure generally relate to a flexible physiological characteristic sensor assembly that includes at least one physiological characteristic sensor, such as a blood glucose sensor.

According to various embodiments, provided is a physiological characteristic sensor assembly. The physiological characteristic sensor assembly includes a flexible top housing including a needle port having a central opening, and a flexible lower housing defining a sensor bore through the lower housing, the sensor bore coaxial with the central opening of the needle port. The physiological characteristic sensor assembly also includes an electrical subsystem disposed between the top housing and the lower housing. The electrical subsystem includes a flexible printed circuit board having a sensor contact pad, a physiological characteristic sensor and an electrically conductive adhesive patch. The physiological characteristic sensor has a distal end that extends through the needle port and a proximal end that includes at least one electrical contact. The conductive adhesive patch electrically and physically couples the at least one electrical contact of the physiological characteristic sensor to the sensor contact pad of the flexible printed circuit board.

Also provided is a physiological characteristic sensor assembly. The physiological characteristic sensor assembly includes a flexible top housing including a needle port having a central opening, and a flexible lower housing defining a sensor bore through the lower housing, the sensor bore coaxial with the central opening of the needle port. The physiological characteristic sensor assembly includes an electrical subsystem disposed between the top housing and the lower housing. The electrical subsystem includes a rigid printed circuit board, a flexible printed circuit board, a sensor contact pad, a physiological characteristic sensor and an electrically conductive adhesive patch. The rigid printed circuit board is electrically coupled to the flexible printed circuit board and disposed between the flexible printed circuit board and the top housing. The physiological characteristic sensor has a distal end that extends through the needle port and a proximal end that includes at least one electrical contact. The conductive adhesive patch electrically and physically couples the at least one electrical contact of the physiological characteristic sensor to the sensor contact pad.

According to various embodiments, provided is a physiological characteristic sensor assembly. The physiological characteristic sensor assembly includes a flexible top housing including a needle port having a central opening, and a flexible lower housing defining a sensor bore through the lower housing, the sensor bore coaxial with the central opening of the needle port. The physiological characteristic sensor assembly includes an electrical subsystem disposed between the top housing and the lower housing. The electrical subsystem includes a rigid printed circuit board having a sensor contact pad, a physiological characteristic sensor and an electrically conductive adhesive patch. The physiological characteristic sensor has a distal end that extends through the needle port and a proximal end that includes at least one electrical contact. The conductive adhesive patch electrically couples the at least one electrical contact of the physiological characteristic sensor to the sensor contact pad.

Further provided is a method of assembling a physiological characteristic sensor assembly. The method includes coupling one or more electrical components to a rigid printed circuit board by temperature reflow soldering at a first temperature, and coupling the rigid printed circuit board to a flexible printed circuit board by temperature reflow soldering at a second temperature. The second temperature less than the first temperature. The rigid printed circuit board and the flexible printed circuit board form an electrical subsystem. The method includes coupling a power source to the flexible printed circuit board such that a portion of the flexible printed circuit board is folded over the power source, and electrically coupling a physiological characteristic sensor to the electrical subsystem. The method includes coupling a double sided adhesive layer to the electrical subsystem, and coupling a second double sided adhesive layer to the double sided adhesive layer such that a proximal end of a physiological characteristic sensor is positioned between the double sided adhesive layer and the second double sided adhesive layer to waterproof the proximal end of the physiological characteristic sensor. The method includes coupling at least a lower housing to the second double sided adhesive layer.

According to various embodiments, provided is a sensor introducer for a physiological characteristic sensor assembly. The sensor introducer includes a sensor introducer body that includes an outer housing that defines an opening to receive the physiological characteristic sensor assembly and an inner housing surrounded by the outer housing. The sensor introducer includes a cradle movable relative to the inner housing from a first position to a second position to deploy the physiological characteristic sensor assembly. The cradle has a cradle flange to receive the physiological characteristic sensor assembly and a cradle body that receives a needle assembly. The cradle body includes at least one locking projection that engages the inner housing to inhibit the movement of the cradle relative to the inner housing in the first position and the at least one locking projection is movable relative to the inner housing to enable the cradle to move from the first position to the second position.

Also provided according to various embodiments is a physiological characteristic sensor system. The system includes a physiological characteristic sensor assembly including a flexible top housing having an alignment feature, a flexible lower housing, an electrical subsystem disposed between the top housing and the lower housing. The electrical subsystem includes a physiological characteristic sensor and an adhesive patch having a first adhesive layer opposite a second adhesive layer, and the first adhesive layer is coupled to the electrical subsystem. The system includes a sensor introducer body that includes an outer housing that defines an opening and an inner housing surrounded by the outer housing. The sensor introducer body includes a cradle movable relative to the inner housing from a first position to a second position to deploy the physiological characteristic sensor assembly. The cradle has a flange that defines a recess that receives the physiological characteristic sensor assembly and a cradle body that receives a needle shuttle having a needle cradle. The sensor introducer includes a lid coupled to the outer housing to enclose the opening.

This summary is provided to introduce a selection of concepts in a simplified form that are further described below in the detailed description. The details of one or more aspects of the disclosure are set forth in the accompanying drawings and the description below. Other features, objects, and advantages of the techniques described in this disclosure will be apparent from the description and drawings, and from the claims. This summary is not intended to identify key features or essential features of the claimed subject matter, nor is it intended to be used as an aid in determining the scope of the claimed subject matter.

BRIEF DESCRIPTION OF DRAWINGS

A more complete understanding of the subject matter may be derived by referring to the detailed description and claims when considered in conjunction with the following figures, wherein like reference numbers refer to similar elements throughout the figures.

FIG. 14 is a bottom view of the sensor introducer of FIG. 10 in the first, retracted position;

FIG. 15 is a bottom view of the sensor introducer of FIG. 10, in which the physiological characteristic sensor assembly is coupled to the sensor introducer of FIG. 10;

FIG. 17 is a schematic environmental view of a user applying a force to move the sensor introducer to the second, deployed position;

FIG. 19 is a schematic environmental view of the physiological characteristic sensor assembly coupled to the body of the user;

FIG. 26 is a cross-sectional view of a portion of an electrical subsystem for use with the physiological characteristic sensor assembly of FIG. 1, in which an adhesive conductive film is used to electrically couple a sensor to the flexible printed circuit board;

FIG. 26A is a top view of the adhesive conductive film of FIG. 26;

FIG. 26B is an exploded rear view of the exemplary electrical subsystem of FIG. 26;

FIG. 27 is an exploded view of another exemplary mounting for a sensor of a physiological characteristic sensor assembly in accordance with various embodiments;

FIG. 27A is a cross-section taken through a portion of the electrical subsystem of FIG. 27, which illustrates the electrical coupling of the sensor;

FIG. 28 is an exploded view of another exemplary mounting for a sensor of a physiological characteristic sensor assembly in accordance with various embodiments;

FIG. 28A is a cross-section taken through a portion of the electrical subsystem of FIG. 28, which illustrates the electrical coupling of the sensor;

FIG. 29 is a partially exploded view of another exemplary mounting for a sensor of a physiological characteristic sensor assembly in accordance with various embodiments;

FIG. 29A is a cross-section taken through a portion of the electrical subsystem of FIG. 29, which illustrates the electrical coupling of the sensor;

FIG. 33 is a top view of another exemplary printed circuit board for a physiological characteristic sensor assembly in accordance with various embodiments;

FIG. 33A is a bottom view of the exemplary printed circuit board of FIG. 33 in accordance with various embodiments;

FIG. 57 is a partially exploded perspective view of another exemplary physiological characteristic sensor assembly in accordance with various embodiments;

FIG. 58 is a partially exploded perspective view of the physiological characteristic sensor assembly of FIG. 57, in which a portion of the flexible printed circuit board of the physiological characteristic sensor assembly has been folded outward in accordance with various embodiments;

DETAILED DESCRIPTION

Figure 1:
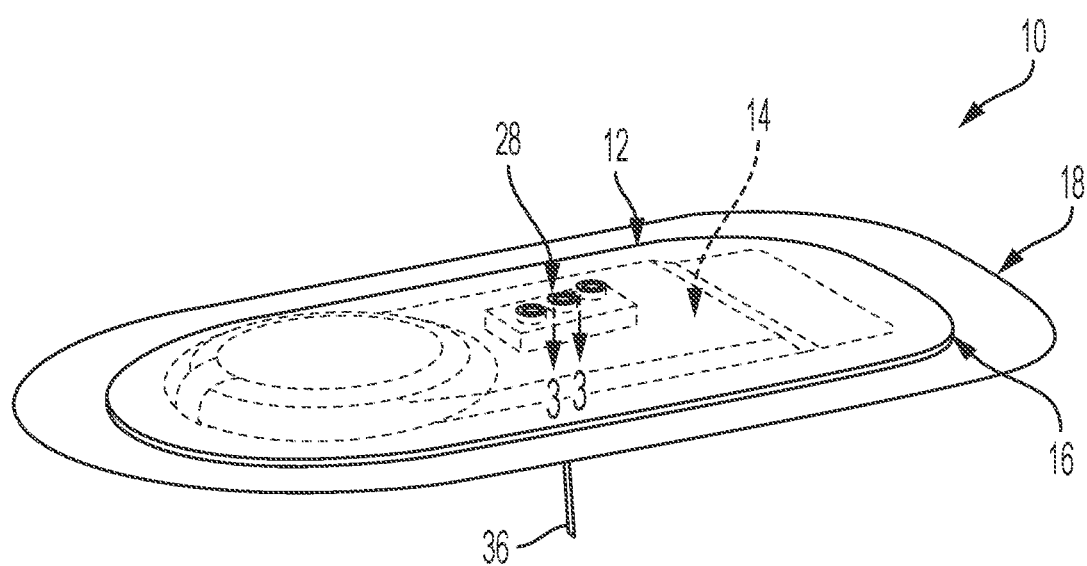
FIG. 1 is a perspective view of an exemplary physiological characteristic sensor assembly in accordance with various embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of schematic, functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the physiological characteristic monitoring systems described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to various embodiments of a physiological characteristic sensor assembly, and in one example, the physiological characteristic sensor assembly is a blood glucose sensor. It should be noted that while the assembly is described herein as being a blood glucose sensor assembly, it will be understood that the method and system of assembly may be employed with a variety of other sensors and/or medical devices. Moreover, the assembly may be employed to integrate a variety of other sensors into a single medical device such that sensors for blood glucose and sensors associated with a variety of other physiological analytes or characteristics of interest may be integrated within this single assembly. Thus, while the non-limiting examples described below relate to an assembly for a blood glucose sensor used to treat diabetes, embodiments of the disclosed subject matter are not so limited. As will be discussed herein, the various embodiments provide a physiological characteristic sensor assembly that is thin and flexible for observing a blood glucose (BG) level of a user. The flexibility of the physiological characteristic sensor assembly enables the physiological characteristic sensor assembly to conform to the varying topography of users and helps minimize sensor motion in-vivo by reducing a transfer of forces. In this regard, if a moment is applied on one end of the physiological characteristic sensor assembly, the flexibility of the physiological characteristic sensor assembly reduces the likelihood of the transfer of the moment to the other end of the physiological characteristic sensor assembly. The reduction in the transfer of forces or moments lowers the probability of the distal segment portion or end of the sensor being partially removed from the subcutaneous tissue, which ensures the performance of the sensor is consistent throughout the duration of wear. Generally, the physiological characteristic sensor assembly has at least one axis of inflection, which enables the physiological characteristic sensor assembly to conform to the anatomy of the user. In addition, a perimeter of the physiological characteristic sensor assembly is flexible and conforms to the surface of the user. The physiological characteristic sensor assembly has a low profile, with a larger surface area that enables the user to wear the physiological characteristic sensor assembly for a prolonged period of time, for example, greater than 14 days. Moreover, the low profile enables the physiological characteristic sensor assembly to be worn more easily under clothing and is more discrete. Further, the low profile reduces the chance of the physiological characteristic sensor assembly catching on objects, such as clothing, chairs, doors, etc., while being worn by the user, thereby improving user comfort. In addition, the various embodiments of the physiological characteristic sensor assembly has a reduced weight, which reduces loading on an adhesive that attaches the physiological characteristic sensor assembly to the user. The reduction in loading also improves the longevity of the physiological characteristic sensor assembly coupled onto the body of the user.

For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295, 786; and United States patent application number 2009/ 0299301 (which are each incorporated by reference herein).

With reference to FIG. 1, a physiological characteristic sensor assembly 10 is shown in accordance with various embodiments. The physiological characteristic sensor assembly 10 is flexible, and has a low profile. In one example, the physiological characteristic sensor assembly 10 includes a first or top housing 12, an electrical subsystem 14, a second or lower housing 16 and a coupling member or adhesive patch 18. It should be noted that the top housing 12 and the lower housing 16 may be integrated into a single housing component, if desired.

Figure 2:
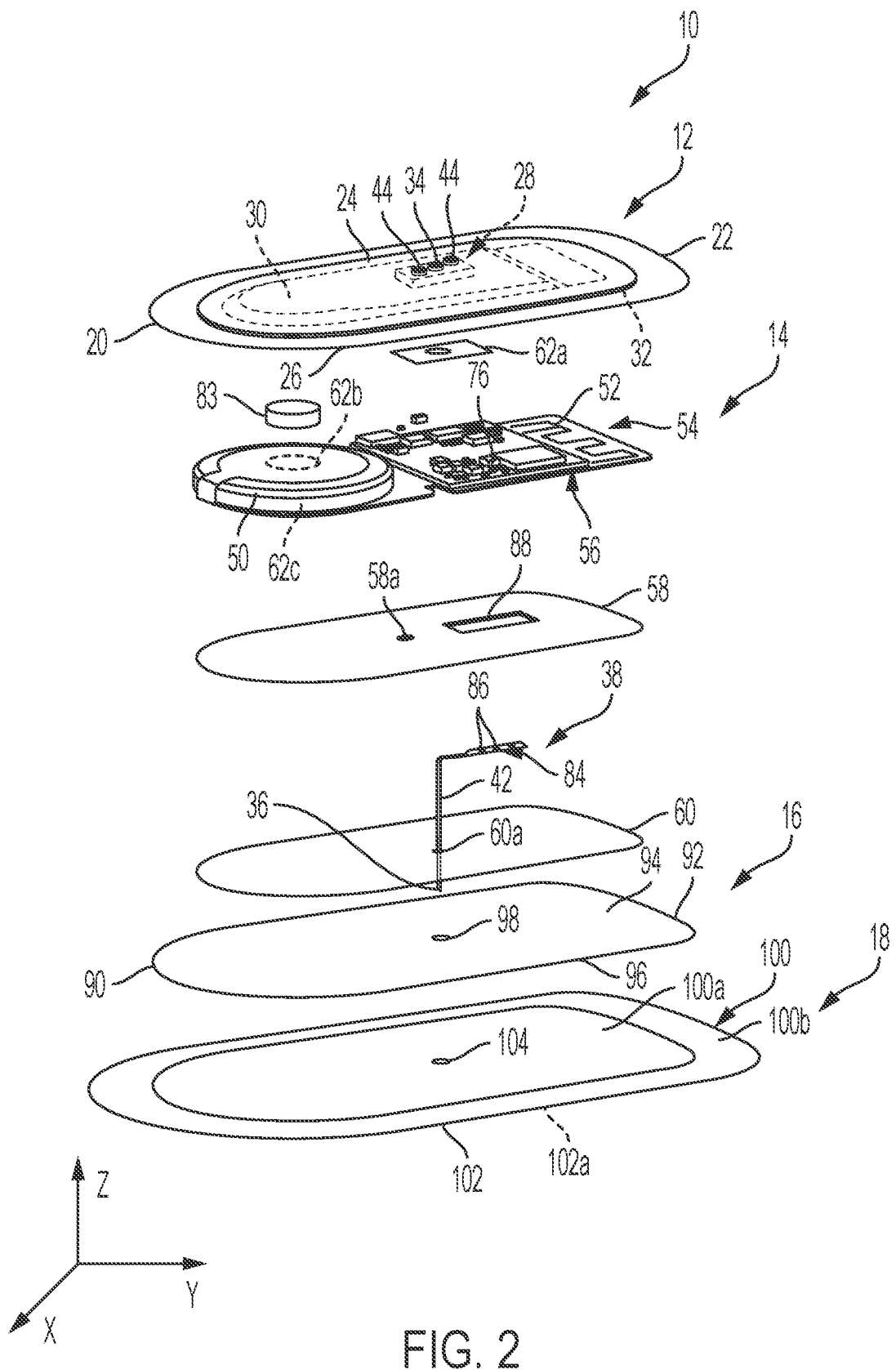
FIG. 2 is an exploded view of the physiological characteristic sensor assembly of FIG. 1.

The top housing 12 is opposite the lower housing 16 and the adhesive patch 18. The top housing 12 forms a portion of an outermost surface of the physiological characteristic sensor assembly 10. The top housing 12 is flexible, and in one example is composed of a biocompatible polymer, including, but not limited to, a polyphenyl ether, thermoplastic polyurethane, silicone, etc. The top housing 12 may be molded, three-dimensionally printed, etc. With reference to FIG. 2, the top housing 12 includes a first end 20 opposite a second end 22, a first side 24 opposite a second side 26 and a needle port 28 coupled to the top housing 12 to extend through the top housing 12 from the first side 24 to the second side 26. In one example, the first end 20 is curved or arcuate in shape, to provide a rounded edge for the user's comfort. The first end 20 also conforms to a portion of the electrical subsystem 14. The second end 22 is substantially rectangular in shape, to conform with a portion of the electrical subsystem 14. The first side 24 is substantially smooth to reduce the likelihood of catching on objects while being worn by the user. The second side 26 defines a cavity 30 and a recess 32. The cavity 30 and the recess 32 are each sized to receive a portion of the electrical subsystem 14. Generally, the cavity 30 is defined through the second side 26 proximate the first end 20 and extends towards the second end 22. The recess 32 is in communication with the cavity 30, and extends from the cavity 30 toward the second end 22 and in this example, extends to be proximate the second end 22.

Figure 3:
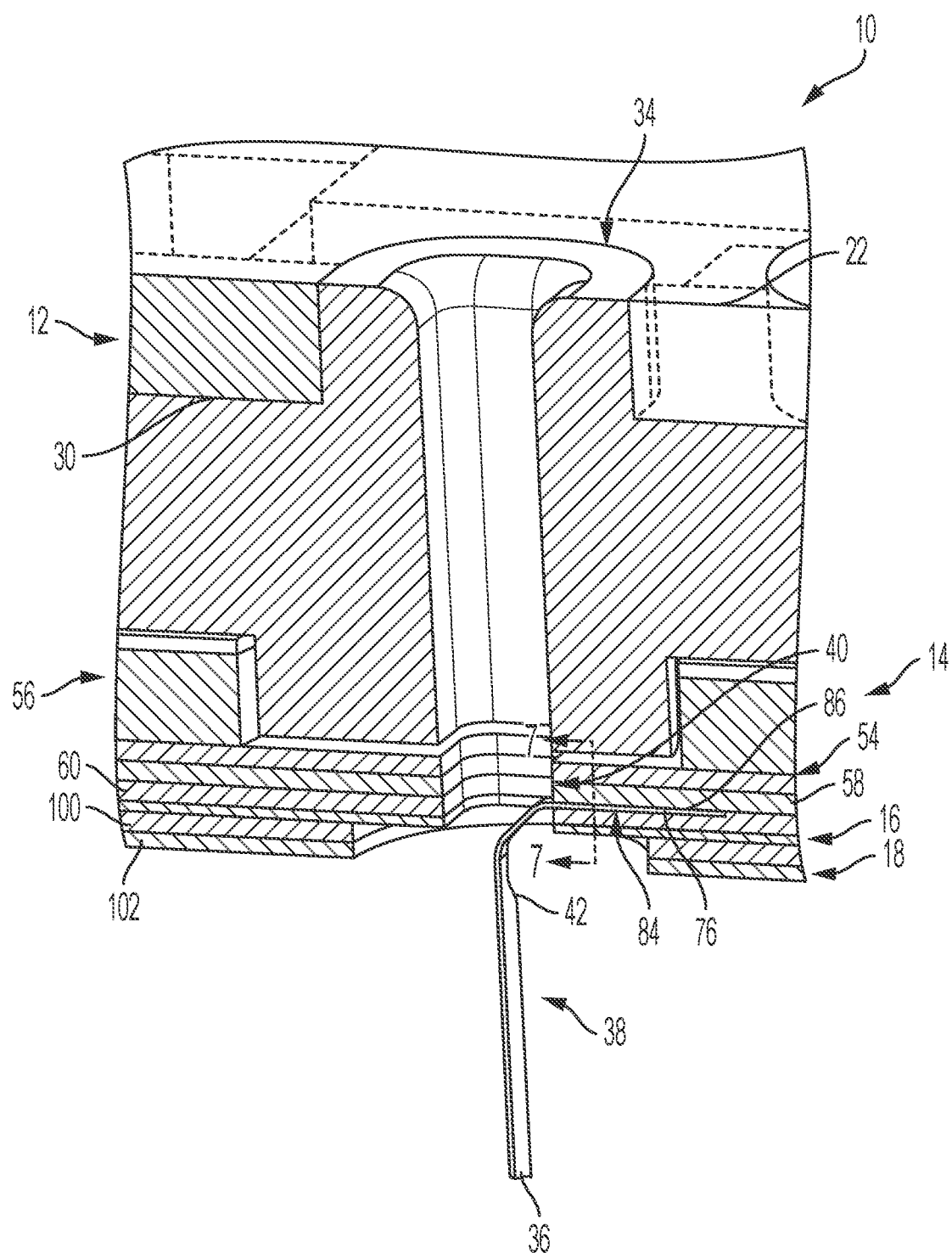
FIG. 3 is a cross-sectional view of a needle port of the physiological characteristic sensor assembly of FIG. 1, taken along line 3-3 of FIG. 1.
Figure 10:
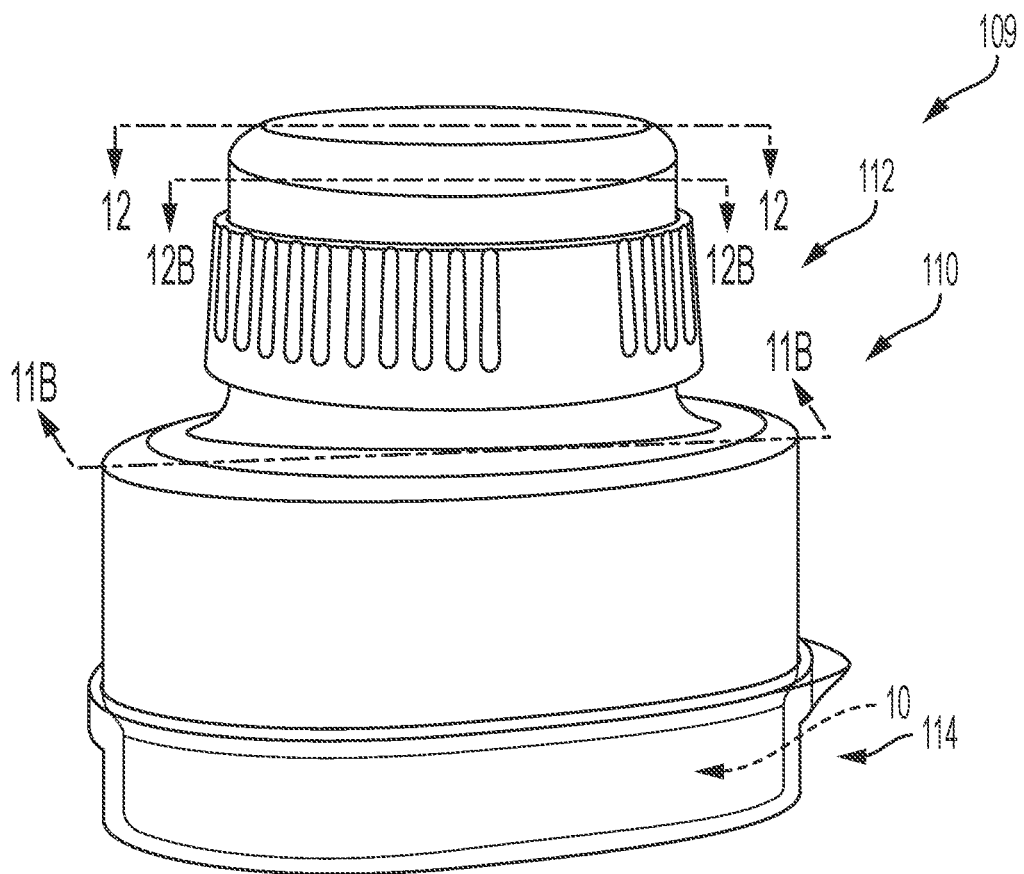
FIG. 10 is a perspective view of a sensor introducer for use with the physiological characteristic sensor assembly of FIG. 1.

As will be discussed further herein, the needle port 28 cooperates with a sensor introducer 110 (FIG. 10) to couple the physiological characteristic sensor assembly 10 to the body of the user. The needle port 28 is composed of a biocompatible polymer, including, but not limited to acrylonitrile butadiene styrene (ABS), polypropylene, etc. The needle port 28 is formed through molding, casting, three dimensional printing, etc., and in one example, the needle port 28 is co-molded with the top housing 12. The needle port 28 includes a central opening or port 34, which enables a needle 256 of the sensor introducer 110 (FIG. 10) to be inserted through the physiological characteristic sensor assembly 10 to insert a distal segment portion or end 36 of a sensor 38 into subcutaneous tissue of the user. With reference to FIG. 3, a cross-section through the central port 34 is shown. The central port 34 extends from first end 20 of the top housing 12 and into the recess 32. The central port 34 is in communication with a needle bore 40 defined through the electrical subsystem 14 and a cannulated portion 42 of the sensor 38 to insert the distal segment end 36 into the body of the user.

With reference back to FIG. 2, the needle port 28 also includes at least one alignment feature or recess 44. In this example, the needle port 28 includes two alignment recesses 44, one on each side of the central port 34. The alignment recesses 44 define substantially cylindrical recesses, which each receive a portion of the sensor introducer 110 (FIG. 10) to couple the inserter to the physiological characteristic sensor assembly 10. It should be noted that the alignment recesses 44 may be located at any desired position relative to the central port 34, and thus, the configuration shown herein is merely an example. Moreover, other techniques, such as alignment pins, projections, notches, etc., may be used to align the sensor introducer 110 (FIG. 10) with the top housing 12 of the physiological characteristic sensor assembly 10.

The electrical subsystem 14 is contained between the top housing 12 and the lower housing 16. In one example, the electrical subsystem 14 includes a power source or battery 50, an antenna 52, a flexible printed circuit board 54, a rigid printed circuit board 56, the sensor 38, a first double sided adhesive layer 58, a second double sided adhesive layer 60, and at least one or a plurality of conductive adhesive patches 62.

The battery 50 provides power to the various components of the electrical subsystem 14. In one example, the battery 50 is a coin-cell battery. It should be noted that in other embodiments the battery 50 may be a flexible thin film battery. Further, while a single battery is shown herein, the battery 50 may also comprise a dual coin cell battery, a dual flexible thin battery, a single thin flat flexible pack battery, etc. As will be discussed, the battery 50 is electrically and physically coupled to the flexible printed circuit board 54.

The antenna 52 enables wireless communication between the physiological characteristic sensor assembly 10 and another device, including, but not limited to, an infusion pump, handheld device (tablet, smart phone, etc.) or other monitoring device. In one example, the antenna 52 is a trace antenna formed on or coupled to the flexible printed circuit board 54. In other embodiments, the antenna 52 may comprise a chip antenna, wire antenna or a stamped metal antenna. The antenna 52 is in electrically coupled to the flexible printed circuit board 54. In one example, the antenna 52 is a Bluetooth low energy (BLE) trace antenna. It should be noted, however, that the antenna 52 may include, but is not limited to, a near field communication (NFC) antenna, RF radio antenna, a far field communication antenna, a wireless communication system configured to communicate via a wireless local area network (WLAN) using IEEE 802.11 standards or by using cellular data communication, a Bluetooth antenna, etc. In certain embodiments, the antenna 52 of the physiological characteristic sensor assembly 10 may include more than one communication device, such as a near field communication (NFC) antenna and a Bluetooth low energy (BLE) trace antenna.

Figure 4:
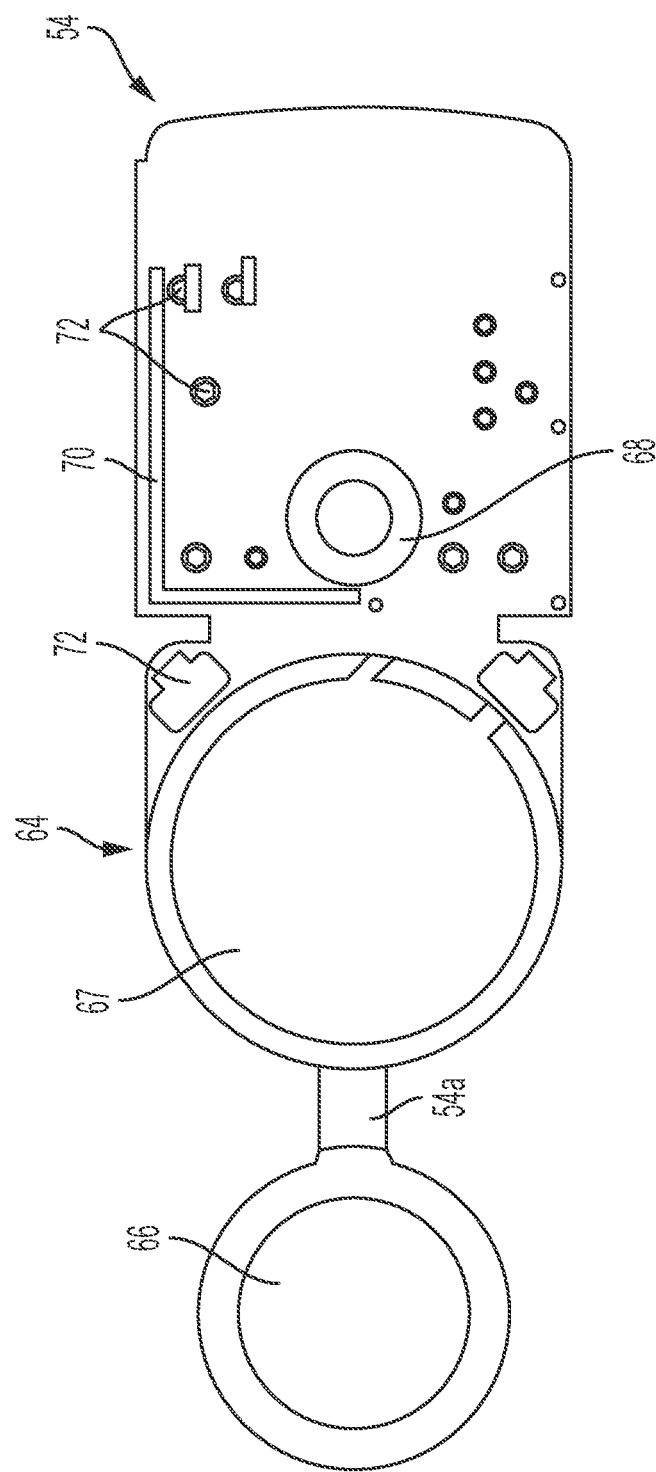
FIG. 4 is a top view of a flexible printed circuit board for use with the physiological characteristic sensor assembly of FIG. 1.
Figure 5:
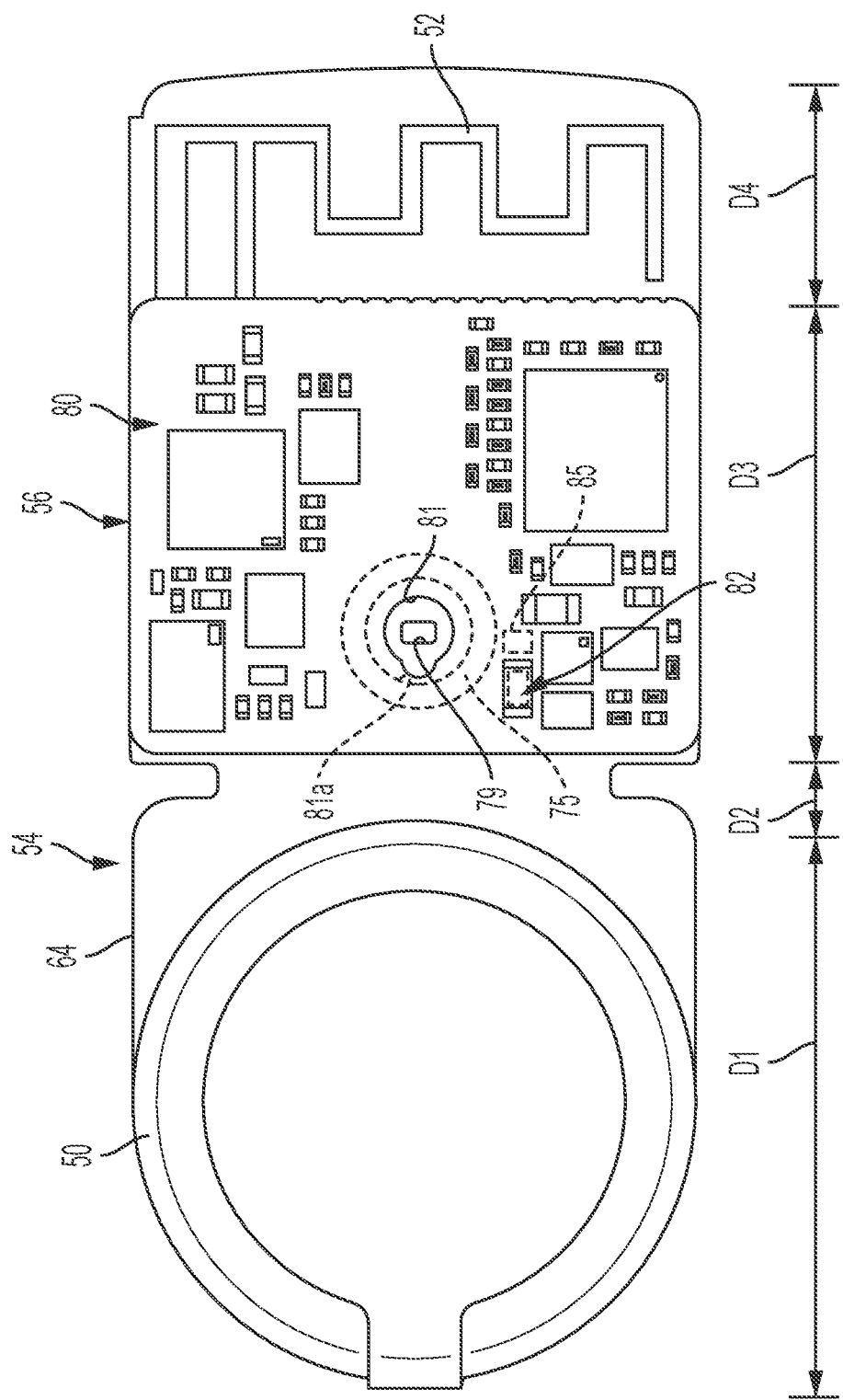
FIG. 5 is a top view of an electrical subsystem of the physiological characteristic sensor assembly of FIG. 1.

The flexible printed circuit board 54 electrically couples the battery 50 and the antenna 52 to the rigid printed circuit board 56 to enable communication between the battery 50, the antenna 52 and the electrical components 80. In one example, the flexible printed circuit board 54 is composed of a bio-compatible polymer, including, but not limited to polyimide. With reference to FIG. 4, a top surface 64 of the flexible printed circuit board 54 is shown. The top surface 64 includes a pair of battery contact pads 66, 67, a contact ring 68, a contact line 70 and one or more contact pads 72. The battery contact pad 66 is separated by the battery contact pad 67 by a thin portion 54a of the flexible printed circuit board 54, which enables the battery contact pad 66 to be folded over on top of the battery 50 so that the battery contact pad 66 is vertically aligned with the battery contact pad 67. One of the battery contact pads 66, 67 couples with a positive terminal of the battery 50, and the other of the battery contact pads 66, 67 couples with a negative terminal of the battery 50. The contact ring 68 is a circular contact pad that cooperates with a circular contact pad on the rigid printed circuit board 56 during a solder reflow process to form a solder ring 75 as shown in FIG. 5. The solder ring 75 provides a waterproof seal between the flexible printed circuit board 54 and the rigid printed circuit board 56. Generally, during a solder reflow process, the solder ring 75 is formed about the contact ring 68 and the circular contact pad on the rigid printed circuit board 56 to create a waterproof seal. Alternatively, a double sided adhesive ring may be used to create a waterproof seal between the flexible printed circuit board 54 and the rigid printed circuit board 56. The contact line 70 and the one or more contact pads 72 cooperate with a corresponding contact line and one or more contact pads on the rigid printed circuit board 56 to electrically couple the rigid printed circuit board 56 to the flexible printed circuit board 54. Generally, the contact ring 68 and the contact line 70 (FIG. 4) cooperate with the solder ring 75 to enable under-filling between the flexible printed circuit board 54 and the rigid printed circuit board 56, which enables the solder ring 75 to provide waterproofing between the flexible printed circuit board 54 and the rigid printed circuit board 56.

Figure 6:
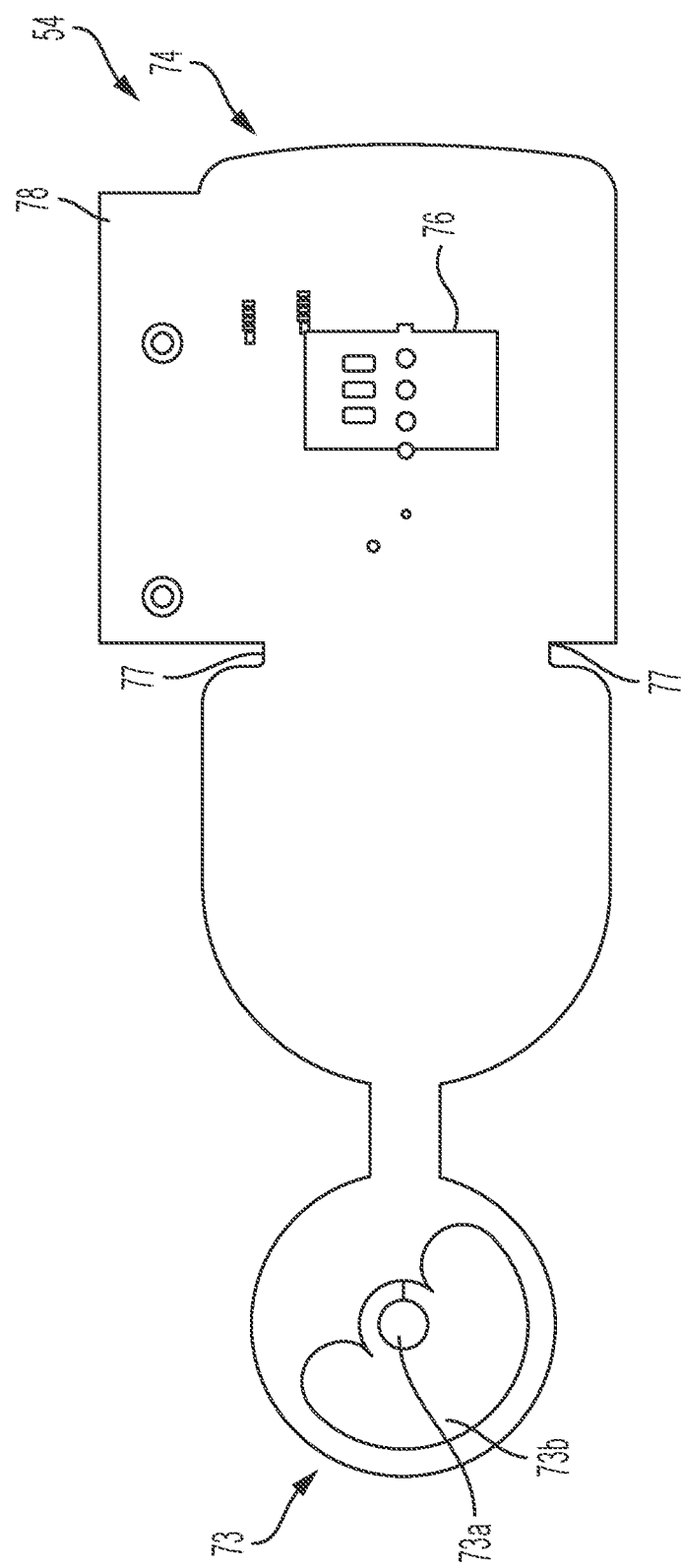
FIG. 6 is a bottom view of the flexible printed circuit board for use with the physiological characteristic sensor assembly of FIG. 1.

With reference to FIG. 6, a bottom surface 74 of the flexible printed circuit board 54 is shown. The bottom surface 74 includes a push button switch pad 73 and a sensor contact pad 76. The sensor contact pad 76 electrically couples the sensor 38 to the flexible printed circuit board 54, and thus, to the rigid printed circuit board 56. The push button switch pad 73 is contacted by a push button 83 (FIG. 2), which closes a switch defined between a center contact pad 73a and an outer contact pad 73b. When the switch is closed by contact with the push button 83, a controller associated with the electrical components 80 supplies power to the electrical subsystem 14. Thus, the push button switch pad 73 cooperates with the push button 83 to power on the electrical subsystem 14.

In this example, the bottom surface 74 is also shown with a portion 78. The portion 78 includes electrical contact pads for the testing and programming of the flexible printed circuit board 54. The portion 78 is removed once testing and programming is complete, via cutting for example, during the assembly of the physiological characteristic sensor assembly 10. In this example, the flexible printed circuit board 54 also includes a pair of cut-outs 77 defined through the top surface 64 and the bottom surface 74. The cut-outs 77 cooperate to provide flexibility between the battery 50 and the rigid printed circuit board 56 when the battery 50 and the rigid printed circuit board 56 are coupled to the flexible printed circuit board 54.

The flexible printed circuit board 54 also includes a sensor bore 79 defined through the top surface 64 and the bottom surface 74. The sensor bore 79 enables the needle of the sensor introducer 110 (FIG. 10) to pass through the flexible printed circuit board 54 and into the cannulated portion 42 of the sensor 38. The rigid printed circuit board 56 also includes a sensor bore 81, which is concentric with the sensor bore 79. The sensor bore 81 of the rigid printed circuit board 56 may be larger than the sensor bore 79, and may include a keyed notch 81a. The keyed notch 81a aligns the sensor bore 79 with the sensor bore 81 during assembly of the electrical subsystem 14. The solder ring 75 is defined about at least a portion of or an entirety of the perimeter of the sensor bore 81 to provide a waterproof seal between the rigid printed circuit board 56 and the flexible printed circuit board 54. In this regard, the solder ring 75 is defined such that solder is present along the perimeter of the sensor bore 81 on the flexible printed circuit board 54 and the rigid printed circuit board 56. Since the solder ring 75 is a solid piece of solder it does not allow for liquid transfer from inside the solder ring 75 to the outside of the solder ring 75.

With reference to FIG. 5, the rigid printed circuit board 56 is shown electrically and physically coupled to the flexible printed circuit board 54. The flexible printed circuit board 54 and the rigid printed circuit board 56 may also include alignment pins or holes for co-registration. In this example, the rigid printed circuit board 56 is physically and electrically coupled to the top surface 64 of the flexible printed circuit board 54. It should be noted that in other embodiments, the rigid printed circuit board 56 may be physically and electrically coupled to the bottom surface 74 (FIG. 6) of the flexible printed circuit board 54. The rigid printed circuit board 56 is electrically and physically coupled to electrical components 80 associated with the physiological characteristic sensor assembly 10, and the electrical components 80 are in communication with the battery 50, the sensor 38 and the antenna 52 coupled to the flexible printed circuit board 54 via the rigid printed circuit board 56. Generally, as the electrical components 80 associated with the physiological characteristic sensor assembly 10 are conventional, the electrical components 80 will not be described in detail herein.

Briefly, the electrical components 80 include at least a controller having a processor and a computer readable media or memory. The processor can be any custom made or commercially available processor, a central processing unit (CPU), a graphics processing unit (GPU), an auxiliary processor among several processors associated with the controller, a semiconductor based microprocessor (in the form of a microchip or chip set), a macroprocessor, any combination thereof, or generally any device for executing instructions. The processor may also include digital signal processors (DSPs), general purpose microprocessors, application specific integrated circuits (ASICs), field programmable logic arrays (FPGAs), or other equivalent integrated or discrete logic circuitry. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller in controlling components associated with the physiological characteristic sensor assembly 10. For example, the processor receives the sensor signals from the sensor 38 as input, and transmits these sensor signals, via the antenna 52, to a remote device, including, but not limited to, an infusion pump, handheld device (tablet, smart phone, etc.) or other monitoring device.

The electrical components 80 may also include an additional communication system, including, but not limited to, a wireless communication system configured to communicate via a wireless local area network (WLAN) using IEEE 802.11 standards or by using cellular data communication, a Bluetooth antenna, etc.

In this example, the physiological characteristic sensor assembly 10 also includes, in addition to the electrical components 80, one or more of a light sensor 82, the push button 83 and a magnet sensor 85. In one embodiment, the light sensor 82 observes a light beam, including, but not limited to ambient light in the example of the top housing 12 being transparent, and generates one or more sensor signals based on the observation of the ambient light. In one example, the processor receives the sensor signals from the light sensor 82 and outputs one or more control signals to the sensor 38 and electrical components 80 to initiate the physiological characteristic sensor assembly 10 for the monitoring of the BG levels of the user. Stated another way, based on the observation of ambient light, the physiological characteristic sensor assembly 10 is activated to monitor the BG levels of the user.

The push button 83 is a tactile dome button, which in one embodiment, enables a user to activate the physiological characteristic sensor assembly 100. In one example, with reference to FIG. 2, the push button 83 is coupled to the flexible printed circuit board 54 so as to be disposed over the battery 50. The push button 83 is coupled to the flexible printed circuit board 54 over the battery 50 as the battery 50 provides sufficient rigidity for the user to depress the push button 83. In one example, the push button 83 is composed of a conductive material, including, but not limited to, aluminum. The user depressing the push button 83, or the application of a force to the push button 83 closes the push button switch pad 73 and causes a signal to be transmitted through the flexible printed circuit board 54 to the controller of the physiological characteristic sensor assembly 100 for initiating the sensor 38 to monitor the BG levels of the user. Stated another way, the depression of the push button 83 generates a signal that, when received by the controller, initiates the monitoring of the BG levels of the user.

The magnet sensor 85 observes a magnetic field, including, but not limited to a magnetic field generated by a magnet 124 associated with a sensor introducer 110 (FIG. 10), and generates one or more sensor signals based on the observation of the magnetic field. In one example, the processor receives the sensor signals from the magnet sensor 85 and outputs one or more control signals to the sensor 38 and electrical components 80 to initiate the physiological characteristic sensor assembly 10 for the monitoring of the user's BG levels. Stated another way, based on the observation of a change in a magnetic field, such as due to a separation of the magnet 124 (and the sensor introducer 110) from the physiological characteristic sensor assembly 10, the physiological characteristic sensor assembly 10 is activated to monitor the user's BG levels. It should be noted that while the physiological characteristic sensor assembly 10 is described as including the light sensor 82, the push button 83 and optionally, the magnet sensor 85 to activate or initiate the physiological characteristic sensor assembly 10, the physiological characteristic sensor assembly 10 may include a single one of the light sensor 82, the push button 83 and the magnet sensor 85.

With reference back to FIG. 2, the sensor 38 includes the distal segment end 36, a proximal end 84 and the cannulated portion 42 that extends from the distal segment end 36 toward the proximal end 84. In this example, the sensor 38 is substantially L-shaped, with the proximal end 84 extending outwardly from the cannulated portion 42 at about a 90 degree angle. The proximal end 84 includes one or more sensor contacts 86. The sensor contacts 86 electrically couple the sensor 38 to the sensor contact pad 76 on the flexible printed circuit board 54 via one of the conductive adhesive patches 62, as will be discussed further herein. In this example, the sensor 38 is an electrochemical sensor that includes the glucose oxidase enzyme, as is well understood by those familiar with glucose sensor technology. The glucose oxidase enzyme enables the sensor 38 to monitor blood glucose levels in a diabetic patient or user by effecting a reaction of glucose and oxygen. Again, although certain embodiments pertain to glucose sensors, the sensor assemblies described herein can be adapted for use with any one of the wide variety of sensors known in the art. Generally, the sensor 38 is positionable in subcutaneous tissue of the user by the needle 256 of the sensor introducer 110 to measure the glucose oxidase enzyme.

Figure 7:
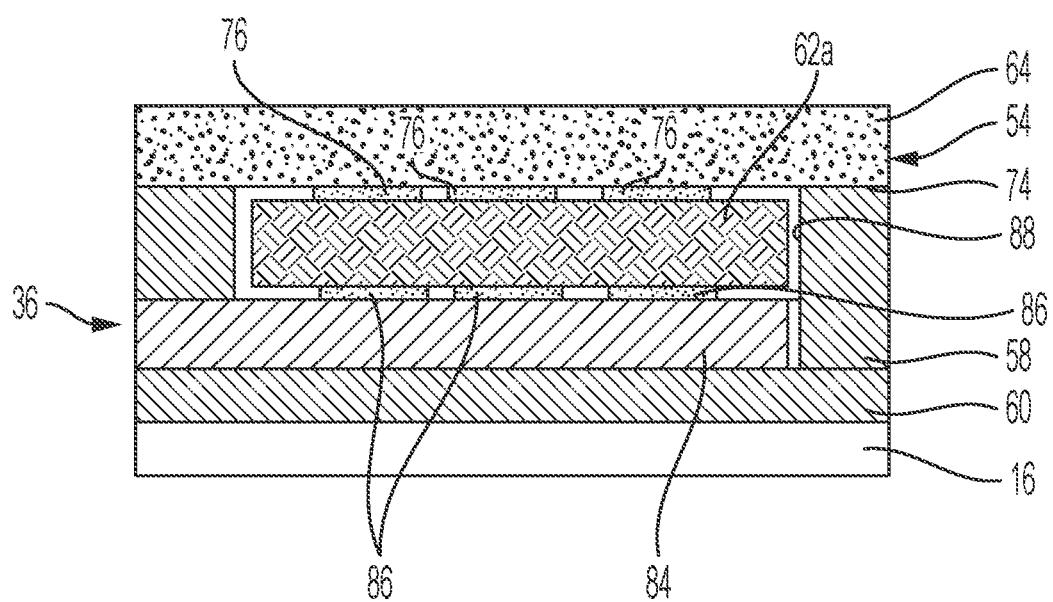
FIG. 7 is a cross-sectional view of a portion of the electrical subsystem, taken along line 3-3 of FIG. 3.

The first double sided adhesive layer 58 cooperates with the second double sided adhesive layer 60 to surround or sandwich the proximal end 84 of the sensor 38 between the double sided adhesive layers 58, 60. By sandwiching the sensor 38 between the double sided adhesive layers 58, 60, the double sided adhesive layers 58, 60 provide waterproofing around the sensor bores 79, 81 (FIG. 5) and the connection of the sensor 38 to the flexible printed circuit board 54 (via the contacts 76, 86). In this regard, with reference to FIG. 3 the double sided adhesive layers 58, 60 cooperate to seal around the central port 34, thereby inhibiting fluids from contacting the electrical subsystem 14. Thus, it should be understood that "waterproofing" is not limited to inhibiting water from entering the electrical subsystem 14, but "waterproofing" is used to denote the inhibiting of all fluids from entering a particular portion of the physiological characteristic sensor assembly 10. In addition, as used herein a "double sided adhesive layer" is a layer of polymer-based material, which is coated on each side with an adhesive, including, but not limited to synthetic rubber based adhesives, acrylic, etc. As shown in FIG. 3, the double sided adhesive layers 58, 60 surround the proximal end 84 of the sensor 38 to inhibit fluids that may flow through the cannulated portion 42 from contacting the connection of the sensor 38 to the flexible printed circuit board 54 and the other portions of the electrical subsystem 14. In this example, the first double sided adhesive layer 58 defines an opening 88, which is substantially rectangular to enable the proximal end 84 of the sensor 38 to be at least partially received within the opening 88 to enable the sensor 38 to be electrically coupled to the flexible printed circuit board 54, as shown in FIG. 7. In this example, the opening 88 receives one of the conductive adhesive patches 62 and the proximal end 84 of the sensor 38 to enable the sensor 38 to be electrically coupled to the flexible printed circuit board 54. With reference to FIG. 2, of the double sided adhesive layers 58, 60 also include a respective sensor bore 58a, 60a. The sensor bore 58a is defined through the double sided adhesive layer 58 to enable a needle associated with the sensor introducer 110 (FIG. 10) to pass through the double sided adhesive layer 58. The sensor bore 60a is defined through the double sided adhesive layer 60 to enable the distal segment end 36 of the sensor 38 to pass through the double sided adhesive layer 60.

With reference to FIG. 2, the conductive adhesive patches 62 electrically couple various portions of the physiological characteristic sensor assembly 10 together. In one example, each of the conductive adhesive patches 62 comprises a Z-axis conductive adhesive, which conducts current in along the Z-axis and is generally non-conductive along the X-axis and the Y-axis. In one example, the conductive adhesive patches 62 are composed of a pressure sensitive adhesive (PSA) transfer tape that is anisotropically electrically conductive. In this example, the conductive adhesive patches 62 are composed of 3M Electrically Conductive Transfer Tape 9703, which is commercially available from 3M Company of St. Paul, Minn.; however, it will be understood that other PSA transfer tape that is anisotropically electrically conductive may be employed. The physiological characteristic sensor assembly 10 includes three conductive adhesive patches 62a, 62b, 62c. The conductive adhesive patch 62a is substantially rectangular, and electrically connects the sensor contact pad 76 with the sensor contacts 86 on the sensor 38, as shown in FIG. 7. FIG. 7 is a detail cross-sectional view that illustrates the connection of the sensor 38 to the flexible printed circuit board 54. As shown, the conductive adhesive patch 62a electrically couples the sensor contact pad 76 of the flexible printed circuit board 54 to the sensor contacts 86 of the sensor 38. The use of the conductive adhesive patch 62a enables an electrical connection between the sensor 38 and the flexible printed circuit board 54 even in instances where the sensor contact pad 76 are slightly misaligned with the sensor contacts 86 of the sensor 38 during assembly. This ensures that the sensor 38 is in electrical communication with the flexible printed circuit board 54 even with variances in manufacturing and/or assembly. The conductive adhesive patch 62b is circular, and electrically couples the battery 50 to the battery contact pad 66 (FIG. 4) on the flexible printed circuit board 54. The conductive adhesive patch 62c is circular, and electrically couples the battery 50 to the battery contact pad 67 (FIG. 4) on the flexible printed circuit board 54. Similarly, the use of the conductive adhesive patches 62b, 62c enable an electrical connection between the battery 50 and the flexible printed circuit board 54 even in instances where the terminal ends of the battery 50 are slightly misaligned with the battery contact pads 66, 67 of the flexible printed circuit board 54 during assembly. This ensures that the battery 50 is in electrical communication with the flexible printed circuit board 54 even with variances in manufacturing and/or assembly.

Figure 8A:
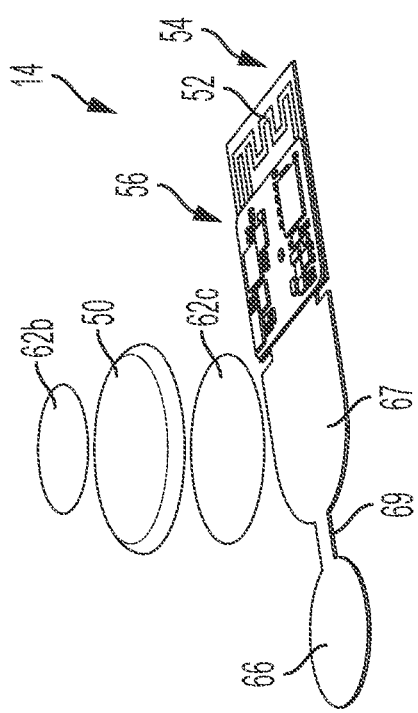
FIG. 8A is a partially exploded view of the electrical subsystem, which illustrates a first action to assemble the electrical subsystem.
Figure 8B:
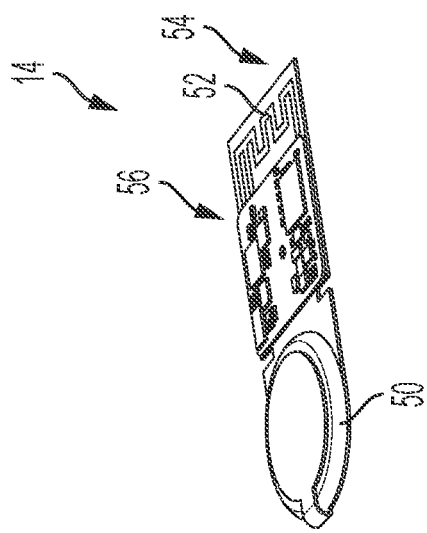
FIG. 8B is a partially exploded view of the electrical subsystem, which illustrates a second action to assemble the electrical subsystem.
Figure 8C:
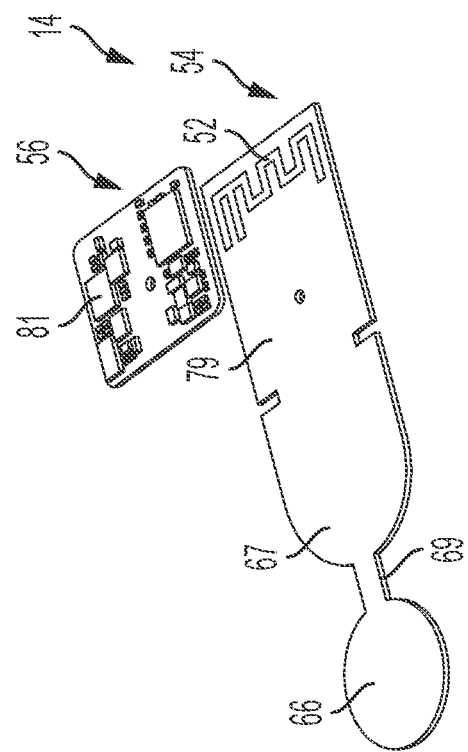
FIG. 8C is a partially exploded view of the electrical subsystem, which illustrates a third action to assemble the electrical subsystem.
Figure 8D:
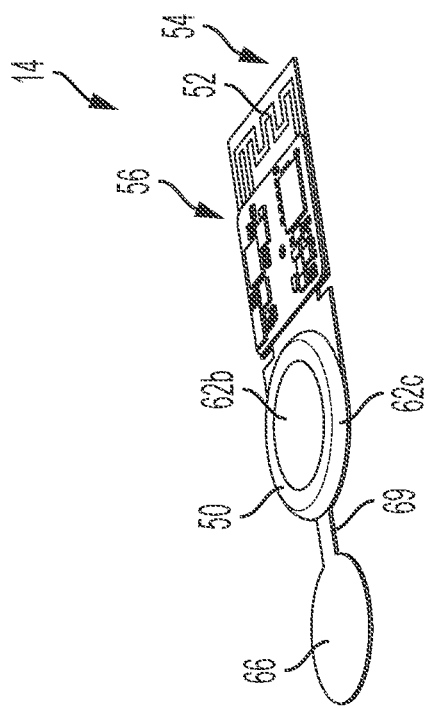
FIG. 8D is a perspective view of the assembled electrical subsystem for the physiological characteristic sensor assembly of FIG. 1.

In one example, with reference to FIGS. 8A-8D, a portion of the assembly of the electrical subsystem 14 is shown. In FIG. 8A, the flexible printed circuit board 54 is shown exploded from the rigid printed circuit board 56, with the sensor bore 79 aligned with the sensor bore 81. Initially, the electrical components 80, the light sensor 82, the push button 83 and the magnet sensor 85 are electrically and physically coupled to the rigid printed circuit board 56 by a high temperature reflow soldering. In one example, the high temperature reflow soldering takes place at a temperature greater than about 200 degrees Celsius, and in one example, from about 210 to about 260 degrees Celsius. In FIG. 8B, with the sensor bore 79 coaxially aligned with the sensor bore 81, low temperature reflow soldering is used to physically and electrically couple the rigid printed circuit board 56 to the flexible printed circuit board 54. In one example, the low temperature reflow soldering takes place at a temperature less than about 200 degrees Celsius, and in one example, from about 90 to about 180 degrees Celsius. Generally, a difference in temperatures between the high temperature reflow soldering and the low temperature reflow soldering is at least about 10%. The conductive adhesive patch 62c is coupled to the battery contact pad 67, and the battery 50 is coupled to the conductive adhesive patch 62c as shown in FIG. 8C. The conductive adhesive patch 62b is coupled to the battery 50, so as to be coupled to a side of the battery 50 opposite a side of the battery 50 coupled to the conductive adhesive patch 62c. The battery contact pad 66 of the flexible printed circuit board 54 is folded over the battery 50 and coupled to the conductive adhesive patch 62b. This electrically couples the battery 50 to the flexible printed circuit board 54.

With brief reference to FIG. 5, the arrangement of the electrical subsystem 14 provides rigid portions interconnected by flexible portions to improve user comfort. In this regard, distances D1 and D3 comprise more rigid or less flexible portions of the electrical subsystem 14, while distances D2 and D4 comprise flexible portions of the electrical subsystem 14. By providing the flexible portion defined by the distance D2 between the more rigid portions defined by distances D1 and D3 associated with the battery 50 and the rigid printed circuit board 56, the physiological characteristic sensor assembly 10 remains flexible to adapt to the contours of the body of the user. In one example, the distance D1 is about 10 millimeters (mm) to about 20 mm, and is about 14 mm to about 17 mm. The distance D2 is about 1 mm to about 5 mm, and is about 1 mm to about 3 mm. The distance D3 is about 10 mm to about 20 mm, and is about 11 mm to about 14 mm. The distance D4 is about 1 mm to about 10 mm, and is about 5 mm to about 7 mm. Thus, within the region defined by D2, the physiological characteristic sensor assembly 10 has a first axis of inflection; within the region defined by D4, the physiological characteristic sensor assembly 10 has a second axis of inflection. These axes enable the physiological characteristic sensor assembly 10 to conform to the body of the user.

Figure 9:
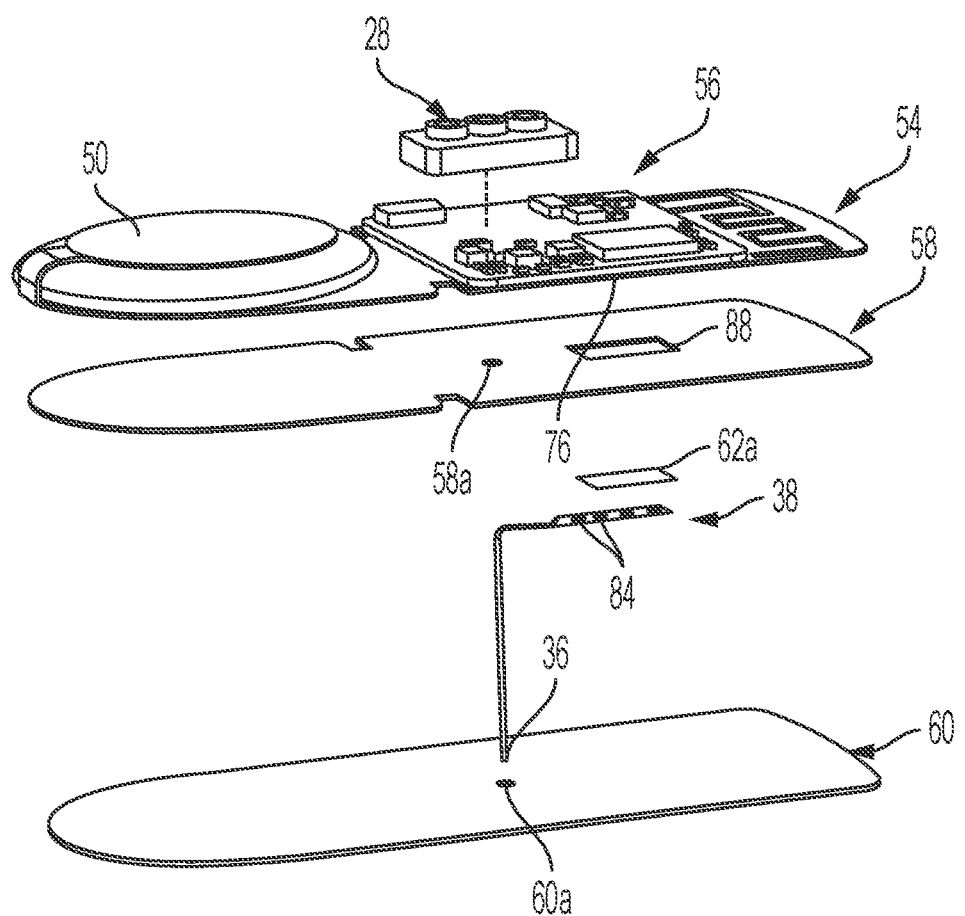
FIG. 9 is a partially exploded view of a portion of the physiological characteristic sensor assembly of FIG. 1.

Once the rigid printed circuit board 56 and the battery 50 are each coupled to the flexible printed circuit board 54, with reference to FIG. 9, the first double sided adhesive layer 58 is coupled or adhered to the bottom surface 74 of the flexible printed circuit board 54 such that the sensor bore 58a is coaxially aligned with the sensor bores 79, 81. Generally, the needle port 28 of the top housing 12 is coupled to the rigid printed circuit board 56 such that the central port 34 is coaxially aligned with the sensor bore 79, 81. The first double sided adhesive layer 58 is also coupled to the flexible printed circuit board 54 such that the opening 88 surrounds the sensor contact pad 76 on the flexible printed circuit board 54. The conductive adhesive patch 62a is coupled to the sensor contact pad 76. The proximal end 84 of the sensor 38 is coupled to the conductive adhesive patch 62a such that the sensor contacts 86 are coupled to the conductive adhesive patch 62a. The second double sided adhesive layer 60 is positioned such that the distal segment end 36 is received through the sensor bore 60a. The second double sided adhesive layer 60 is coupled or adhered to the first double sided adhesive layer 58 to form a seal about the bores 79, 81, 58a, 60a.

With reference back to FIG. 2, the lower housing 16 is substantially planar, and is flexible. In one example is composed of a biocompatible polymer, including, but not limited to, polyethylene terephthalate. The lower housing 16 may be molded, three-dimensionally printed, cast, etc. The lower housing 16 cooperates with the top housing 12 to encase, surround or enclose the electrical subsystem 14. In one example, the lower housing 16 is coupled to the top housing 12 by thermal welding, however, the lower housing 16 may be coupled to the top housing 12 through any suitable technique, including, but not limited to RF welding, laser welding, ultrasonic welding, epoxy, double sided adhesives, etc. The lower housing 16 includes a first housing end 90 opposite a second housing end 92, a first housing side 94 opposite a second housing side 96 and a sensor bore 98 defined through the lower housing 16 from the first housing side 94 to the second housing side 96. In one example, the first housing end 90 is curved or arcuate in shape, to provide a rounded edge for the user's comfort and conforms with the shape of the first end 20 of the top housing 12. The first housing end 90 also conforms to the battery 50 of the electrical subsystem 14. The second housing end 92 is substantially rectangular in shape, to conform to the shape of the antenna 52 of the electrical subsystem 14. The first housing side 94 is coupled or adhered to the second double sided adhesive layer 60 such that the sensor bore 98 is coaxially aligned with the sensor bore 60a to receive the distal segment end 36 of the sensor 38 therethrough. The second housing side 96 is coupled to the adhesive patch 18.

The adhesive patch 18 is coupled to the lower housing 16 and affixes the lower housing 16, and thus, the sensor 38, to the skin of the user. The adhesive patch 18 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

The adhesive patch 18 is substantially oval in shape, and has a first patch side 100 opposite a second patch side 102. The first patch side 100 includes an adhesive layer 100a and a non-adhesive offset portion 100b. The adhesive layer 100a couples the lower housing 16 to the adhesive patch 18 to couple the top housing 12, the electrical subsystem 14 and the lower housing 16 to the adhesive patch 18. The offset portion 100b surrounds a perimeter of the adhesive layer 100a, and thus, a perimeter of the lower housing 16. The second patch side 102 includes a second adhesive layer 102a that couples the adhesive patch 18 and the physiological characteristic sensor assembly 10 to the skin of the user. In certain instances, the second adhesive layer 102a may be coupled with a second backing liner, which is removable by the user prior to the deployment of the sensor 38 at the sensor site.

The adhesive patch 18 also defines a sensor bore 104 that extends through the adhesive patch 18 from the first patch side 100 to the second patch side 102. The sensor bore 104 enables the distal segment end 36 of the sensor 38 to pass through the adhesive patch 18 for subcutaneous placement into the body of the user.

In one example, with reference to FIG. 2, with the electrical subsystem 14 assembled as discussed above and the lower housing 16 formed, the lower housing 16 is coupled or adhered to the second double sided adhesive layer 60 such that the distal segment end 36 passes through the sensor bore 98. The top housing 12 formed with the needle port 28 co-molded with the top housing 12. The top housing 12 is positioned over the electrical subsystem 14 such that the central port 34 of the needle port 28 is coaxially aligned with the sensor bore 79, 81. The top housing 12 is coupled to the lower housing 16, via thermal welding, for example. With the adhesive patch 18 formed, the adhesive layer 100a of the adhesive patch 18 is coupled to the lower housing 16 such that the distal segment end 36 extends through the sensor bore 104.

Figure 11:
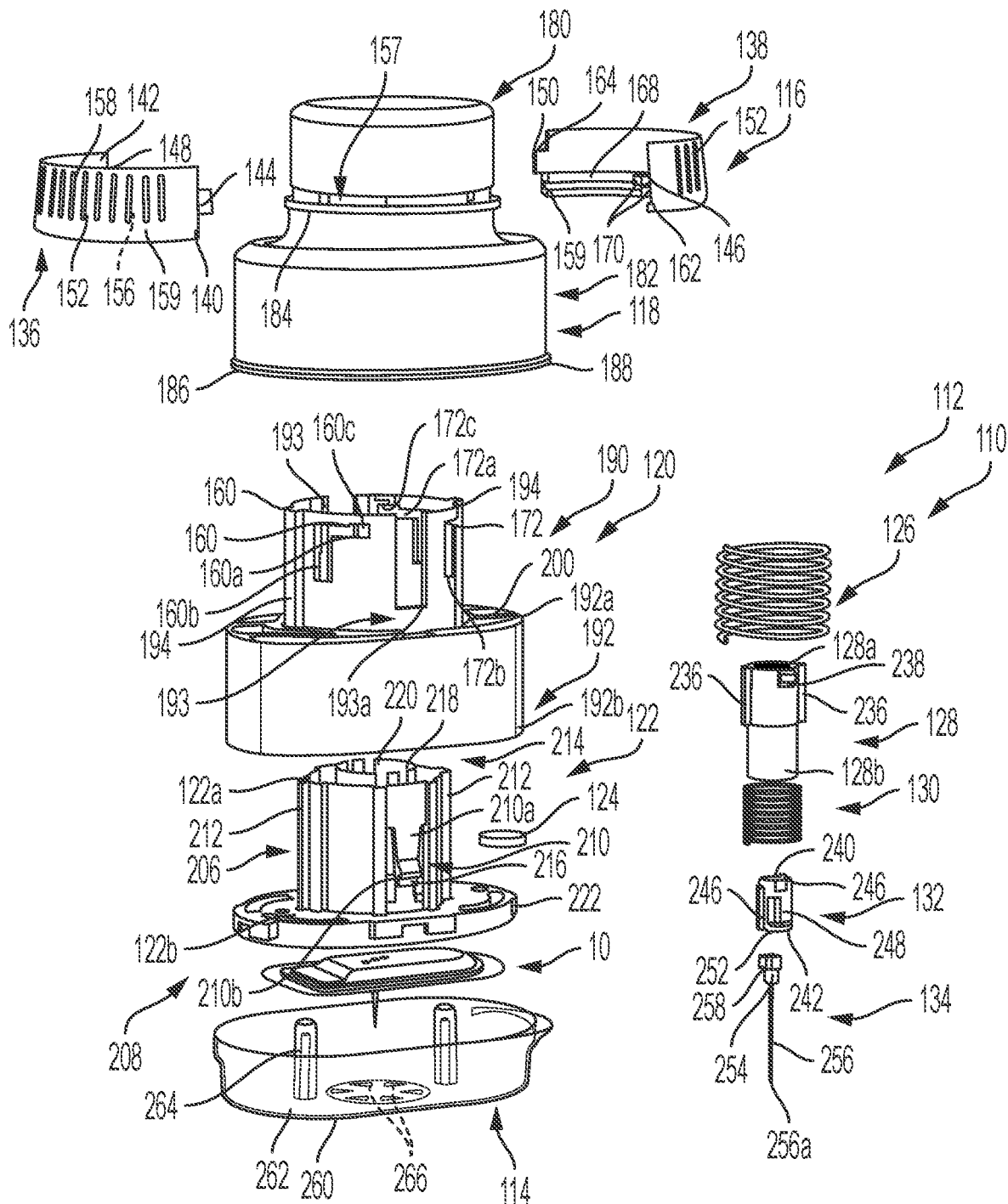
FIG. 11 is an exploded view of the sensor introducer of FIG. 10.

With the physiological characteristic sensor assembly 10 assembled, the physiological characteristic sensor assembly 10 may be coupled to a user. In one example, with reference to FIG. 10, the physiological characteristic sensor assembly 10 is coupled to the skin of a user with the sensor introducer 110. The sensor introducer 110 includes an introducer body 112 and a cover or lid 114. As the physiological characteristic sensor assembly 10 may be received wholly within the sensor introducer 110, the sensor introducer 110 may also be used to package and ship the physiological characteristic sensor assembly 10 to a user. Thus, the physiological characteristic sensor assembly 10 in combination with the sensor introducer 110 may be considered a physiological characteristic sensor system 109. With reference to FIG. 11, in one example, the introducer body 112 includes a collar assembly 116, an outer housing 118, an inner housing 120, a cradle 122, a coupling feature or the magnet 124, a deployment member or deployment spring 126, a needle shuttle 128, a retraction spring 130, a needle cradle 132 and a needle assembly 134. As will be discussed, the sensor introducer 110 is movable from a first, retracted position in which the physiological characteristic sensor assembly 10 is coupled to the sensor introducer 110, to a second, deployed position in which the physiological characteristic sensor assembly 10 is coupled to the body of the user, and a third, disposal position in which the sensor introducer 110 may be safely discarded by the user.

Figure 11A:
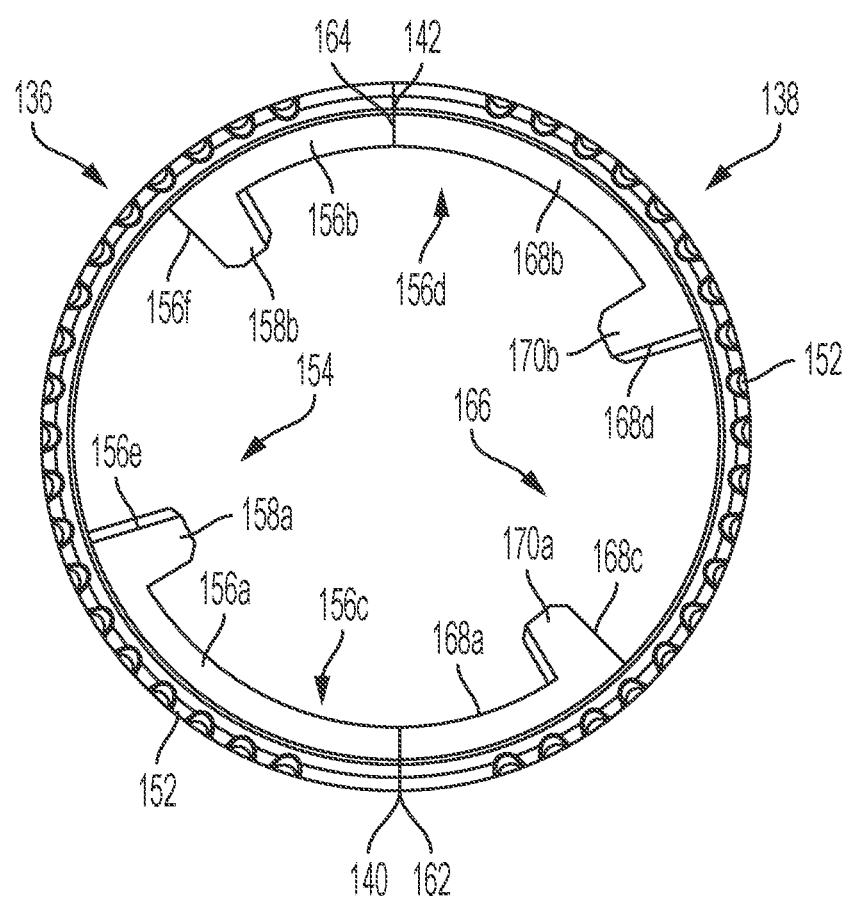
FIG. 11A is a top view of a collar assembly of the sensor introducer of FIG. 10.

The collar assembly 116 is coupled to the outer housing 118, and is movable or rotatable to unlock the inner housing 120 from the outer housing 118. In one example, the collar assembly 116 is rotatable clockwise to unlock or release the inner housing 120. In this example, with reference to FIG. 11A, a top view of the collar assembly 116 is shown. The collar assembly 116 includes a first collar ring 136 and a second collar ring 138. The first collar ring 136 is substantially semi-circular, and has a first end 140 opposite a second end 142. With reference back to FIG. 11, the first end 140 includes a tab 144 that extends outwardly away from the first end 140. The tab 144 is received within a slot 146 defined in the second collar ring 138 to couple the first collar ring 136 to the second collar ring 138. The second end 142 includes a slot 148, which receives a tab 150 of the second collar ring 138 to couple the second collar ring 138 to the first collar ring 136. The first collar ring 136 also includes an outer surface 152 opposite an inner surface 154. In one example, the outer surface 152 includes a plurality of ribs to define a graspable portion for a user. With reference to FIG. 11A, the inner surface 154 includes a pair of rails 156, a pair of rail tabs 158 and a housing slot 159. A first rail 156a of the pair of rails 156 extends radially inward from the inner surface 154, and extends along the inner surface 154 from the first end 140 toward the second end 142. A second rail 156b of the pair of rails 156 extends radially inward from the inner surface 154, and extends along the inner surface 154 from the second end 142 toward the first end 140. Generally, the first rail 156a and the second rail 156b are spaced apart along the perimeter of the first collar ring 136. The rails 156a, 156b slidably engages with a collar slot 157 defined in the outer housing 118. In one example, the first rail 156a extends for a greater arc length than the second rail 156b, however, the rails 156a, 156b may extend for the same arc length. The rails 156a, 156b cooperate with corresponding rails 168a, 168b defined on the second collar ring 138 to define a substantially continuous rail surface 156c, 156d, respectively.

A first rail tab 158a of the pair of rail tabs 158 extends radially inward from the first rail 156a at a terminal end 156e of the first rail 156a. A second rail tab 158b of the pair of rail tabs 158 extends radially inward from the second rail 156b at a terminal end 156f of the second rail 156b. Each of the rail tabs 158 engages with a respective tab slot 160 defined in the inner housing 120 to couple the inner housing 120 to the outer housing 118 in the locked position. With reference to FIG. 11, the housing slot 159 receives a portion of the outer housing 118 to slidably couple the first collar ring 136 to the outer housing 118. In one example, the housing slot 159 is substantially U-shaped, and is defined within the inner surface 154 from the first end 140 to the second end 142.

The second collar ring 138 is substantially semi-circular, and has a first end 162 opposite a second end 164. The first end 162 includes the slot 146, which receives the tab 144 of the first collar ring 136 to couple the second collar ring 138 to the first collar ring 136. The second end 164 includes the tab 150 that extends outwardly away from the second end 164. The tab 150 is received within the slot 148. The second collar ring 138 also includes the outer surface 152 opposite an inner surface 166. With reference to FIG. 11A, the inner surface 166 includes a pair of rails 168, a pair of rail tabs 170 and the housing slot 159. A first rail 168a of the pair of rails 168 extends radially inward from the inner surface 166, and extends along the inner surface 166 from the first end 162 toward the second end 164. A second rail 168b of the pair of rails 168 extends radially inward from the inner surface 166, and extends along the inner surface 166 from the second end 164 toward the first end 162. Generally, the first rail 168a and the second rail 168b are spaced apart along the perimeter of the second collar ring 138. The rails 168a, 168b slidably engages with the collar slot 157 defined in the outer housing 118. In one example, the second rail 168b extends for a greater arc length than the first rail 168a, however, the rails 168a, 168b may extend for the same arc length.

A first rail tab 170a of the pair of rail tabs 170 extends radially inward from the first rail 168a at a terminal end 168c of the first rail 168a. A second rail tab 170b of the pair of rail tabs 170 extends radially inward from the second rail 168b at a terminal end 168d of the second rail 168b. Each of the rail tabs 170 engages with a respective tab slot 172 defined in the inner housing 120 to couple the inner housing 120 to the outer housing 118 in the locked position.

With reference to FIG. 11, the collar assembly 116 is coupled to the outer housing 118, and the outer housing 118 surrounds the inner housing 120. The outer housing 118 is composed of a suitable polymer-based material, and may be cast, molded, printed, etc. The outer housing 118 includes a top housing portion 180 and a bottom housing portion 182. The top housing portion 180 extends outwardly from the bottom housing portion 182. The top housing portion 180 is substantially cylindrical, however, the top housing portion 180 may have any desired shape. The top housing portion 180 defines the collar slot 157 about a portion of a perimeter of the top housing portion 180. The top housing portion 180 also includes a lip 184, which extends about the perimeter of the top housing portion 180. The lip 184 projects outwardly from a surface of the top housing portion 180 and is received within the housing slot 159 of the respective one of the first collar ring 136 and the second collar ring 138.

Figure 12:
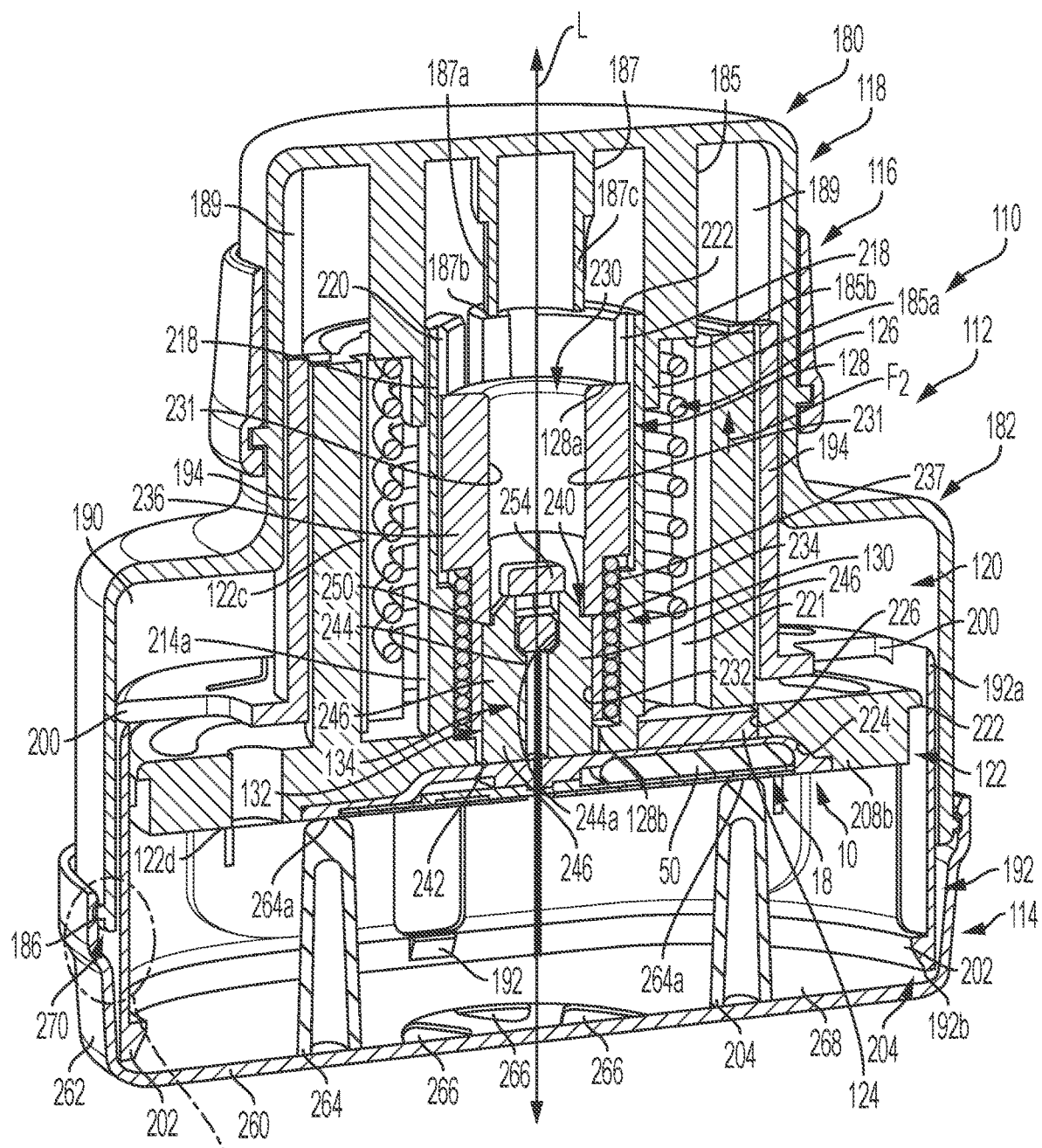
FIG. 12 is a cross-section of the sensor introducer of FIG. 10, with the physiological characteristic sensor assembly of FIG. 1 coupled to the sensor introducer, the sensor introducer in a first, retracted position, taken along line 12-12 of FIG. 10.
Figure 12A:
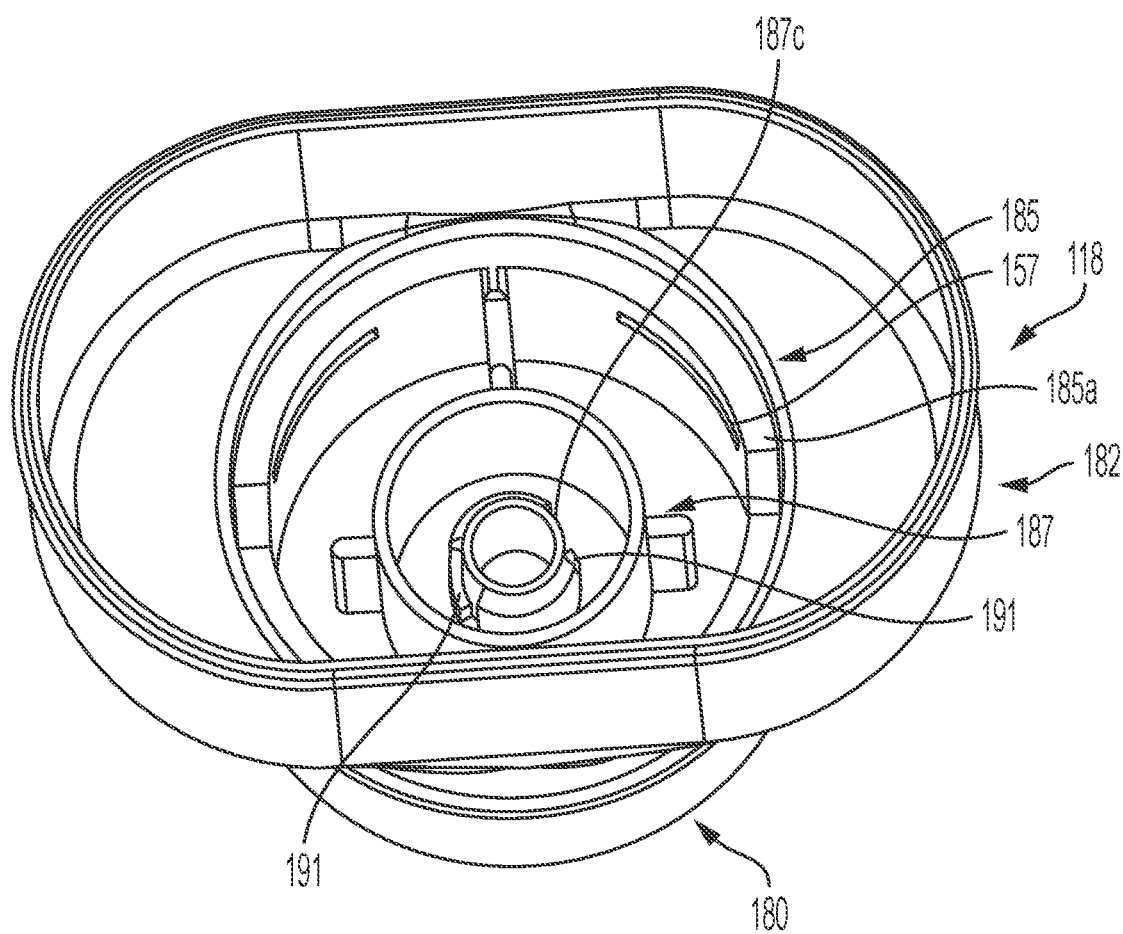
FIG. 12A is a bottom view of an outer housing of the sensor introducer of FIG. 10.

With reference to FIG. 12, the top housing portion 180 includes a first projection 185 and a second projection 187 that are each defined within the top housing portion 180. In FIG. 12, the sensor introducer 110 is in the first, retracted position. The first projection 185 and the second projection 187 are each substantially cylindrical, and the second projection 187 is concentric with the first projection 185. The first projection 185 extends inwardly from a first end of the top housing portion 180 toward the bottom housing portion 182. An end 185a of the first projection 185 has a reduced wall thickness to provide a stop 185b for the deployment spring 126. The reduced wall thickness of the end 185a also provides a guide for the movement of the deployment spring 126. The second projection 187 extends inwardly from a first end of the top housing portion 180 toward the bottom housing portion 182. In this example, the second projection 187 extends for a distance along a longitudinal axis L, which is different and less than a distance the first projection 185 extends. The second projection 187 has a reduced wall thickness 187a from an end 187b that extends toward the first end of the top housing portion 180 to receive the needle shuttle 128. Generally, with reference to FIG. 12A, an outer surface 187c of the second projection 187 is configured to correspond with a first shuttle end 128a of the needle shuttle 128 to couple the needle shuttle 128 to the top housing portion 180 in a third, disposal position of the introducer body 112. In this regard, in one example, the outer surface 187c of the second projection 187 includes a pair of curved surfaces 191. Each of the pair of curved surfaces 191 cooperates with the first shuttle end 128a to cause a movement or rotation of the needle shuttle 128 as the sensor introducer 110 moves from the second, deployed position to the third, disposal position.

Figure 12B:
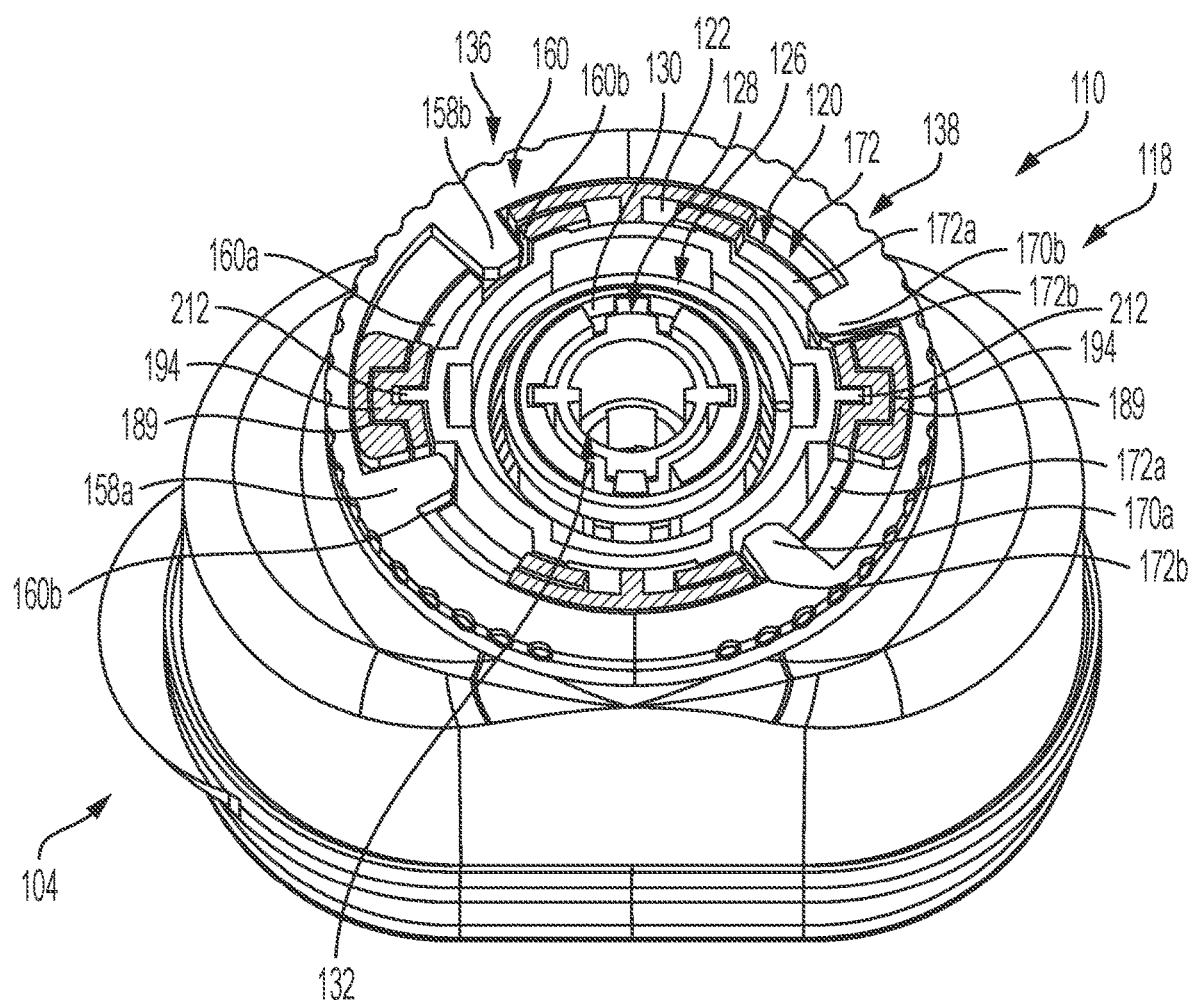
FIG. 12B is a cross-section of the sensor introducer of FIG. 10, with the physiological characteristic sensor assembly of FIG. 1 coupled to the sensor introducer, the sensor introducer in a second, deployed position, taken along line 12B-12B of FIG. 10.

With reference to FIG. 12B, the top housing portion 180 also includes a pair of guide slots 189. The guide slots 189 are defined along an inner surface of the top housing portion 180 and extend along an axis substantially parallel to the longitudinal axis L. The guide slots 189 are substantially U-shaped, and are opposite each other to receive corresponding guides 194 of the inner housing 120 to direct the movement of the inner housing 120 relative to the outer housing 118.

With reference back to FIG. 11, the bottom housing portion 182 is shaped to correspond to the physiological characteristic sensor assembly 10. In this example, the bottom housing portion 182 is substantially oval in shape. The bottom housing portion 182 includes a retaining lip 186, which extends about a perimeter of the bottom housing portion 182. The retaining lip 186 couples the lid 114 to the introducer body 112. The bottom housing portion 182 also defines an opening 188, which enables the inner housing 120 to be received within the outer housing 118.

The inner housing 120 is received within the outer housing 118. In one example, the inner housing 120 has a shape that corresponds to the shape of the outer housing 118. The inner housing 120 is composed of a suitable polymer-based material, and may be cast, molded, printed, etc. The inner housing 120 includes a top portion 190 and a bottom portion 192.

The top portion 190 defines the pair of tab slots 160 and the pair of tab slots 172. The top portion 190 also includes two guides 194 and defines a pair of cradle slots 193. Each of the tab slots 160 are defined opposite the tab slots 172 and are separated by the pair of cradle slots 193. The tab slots 160 are spaced apart between the cradle slots 193 by one of the guides 194. The tab slots 160, 172 are each substantially L-shaped, with a first leg 160a, 172a defined along a perimeter of the top portion 190, and a second leg 160b, 172b that is substantially perpendicular to the first leg 160a, 172a and defined to extend from a first end of the top portion 190 toward the bottom portion 192. With reference to FIG. 12B, the tab slots 160, 172 receive a respective one of the rail tabs 158, 170 of the first collar ring 136 and the second collar ring 138. In FIG. 12B, the sensor introducer 110 is in the second, deployed position. As shown in FIG. 12B, in the second, deployed positions, the rail tabs 158, 170 are moved or rotated (through the movement or rotation of the collar assembly 116) such that the rail tabs 158, 170 are aligned and received within the second leg 160b, 172b of the tab slots 160, 172 to enable the movement of the inner housing 120 relative to the outer housing 118. In one example, with reference back to FIG. 12, each first leg 160a, 172a includes a notched end 160c, 172c. The notched end 160c, 172c requires a user to apply a force to rotate the collar assembly 116 to unlock the introducer body 112. This also ensures that vibrations, such as bumps, do not inadvertently unlock the collar assembly 116 and move the introducer body 112 toward a second, deployed position.

The guides 194 are defined on opposite sides of the top portion 190, and extend from the first end of the top portion 190 to the bottom portion 192. The guides 194 extend along an axis substantially parallel to the longitudinal axis L, and are received in a respective one of the guide slots 189 of the outer housing 118. The guides 194 direct the movement of the inner housing 120 along the longitudinal axis L, and relative to the outer housing 118. The cradle slots 193 receive a portion of the cradle 122 and direct a movement of the cradle 122 relative to the inner housing 120. Generally, the cradle slots 193 are defined through the first end of the top portion 190 toward the bottom portion 192. The cradle slots 193 define a range of travel for the cradle 122.

The bottom portion 192 includes a plurality of relief openings 200 defined through a top side 192a, and at least one cradle tab 202 (FIG. 12). The plurality of relief openings 200 provides a mass savings for the inner housing 120 and may also provide for a lower cost associated with the manufacture of the inner housing 120. In one example, with reference to FIG. 12, the bottom portion 192 defines a plurality of cradle tabs 202, which are spaced apart about a perimeter of the bottom portion 192 proximate a second side 192b of the bottom portion 192. The cradle tabs 202 contact a portion of the cradle 122 to limit a motion of the cradle 122 and to retain the cradle 122 within the inner housing 120. The second side 192b also has an open perimeter or defines an opening 204 to enable the physiological characteristic sensor assembly 10 to be received within and surrounded by the inner housing 120.

With reference back to FIG. 11, the cradle 122 guides the movement of the needle shuttle 128 relative to the inner housing 120 and into the anatomy. The cradle 122 is composed of a suitable polymer-based material, and may be cast, molded, printed, etc. In one example, the cradle 122 includes a cradle body 206 and a cradle flange 208. The cradle body 206 includes a pair of locking tabs 210, a pair of cradle guides 212 and a needle shuttle receptacle 214.

The pair of locking tabs 210 are movable to lock the cradle 122 to the cradle slots 193 of the inner housing 120. In one example, the locking tabs 210 each have a first end 210a coupled to the cradle 122 proximate a first end 122a of the cradle 122. The locking tabs 210 also have a second end 210b, opposite the first end 210a, which includes a hook 216. The locking tabs 210 are biased against the top portion 190 of the inner housing 120 when the introducer body 112 is in the first, retracted position. In this regard, with reference to FIG. 11B, the locking tabs 210 are shown engaged with the inner housing 120 in the first, retracted position. In the first, retracted position, the hook 216 of the locking tabs 210 is coupled to or rests on an edge 193a of the cradle slot 193. In order to move the cradle 122 relative to the inner housing 120, an internal flange 195 of the outer housing 118 contacts the locking tabs 210 and moves the locking tabs 210 out of engagement with the cradle slot 193.

The cradle guides 212 are defined on opposite sides of the cradle 122, and extend from the first end 122a to the cradle flange 208. The cradle guides 212 extend along an axis substantially parallel to the longitudinal axis L, and are received in a respective one of the cradle slots 193 of the inner housing 120. The cradle guides 212 direct the movement of the cradle 122 along the longitudinal axis L, and relative to the inner housing 120.

Figure 12C:
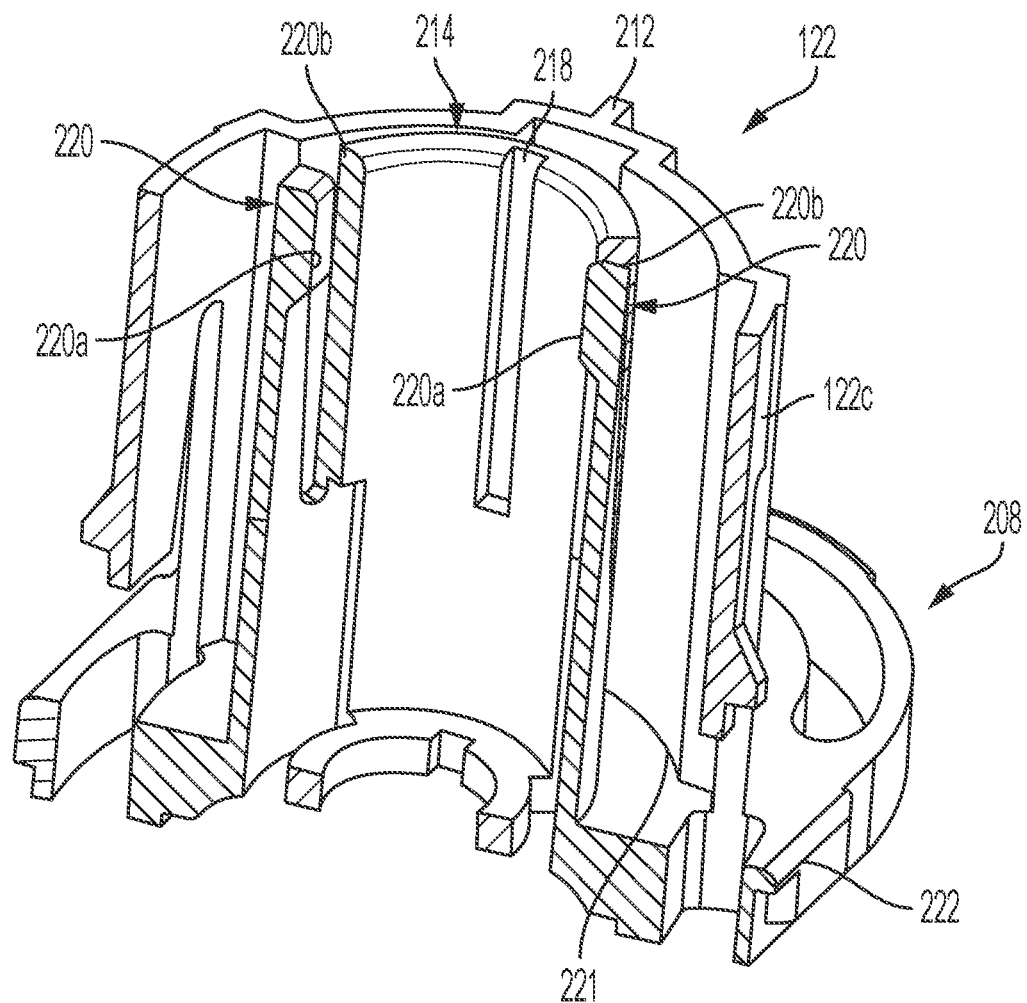
FIG. 12C is a cross-section of a cradle of the sensor introducer of FIG. 10, taken along line 12C-12C of FIG. 11.

With reference to FIG. 12, the needle shuttle receptacle 214 receives the needle shuttle 128. The needle shuttle receptacle 214 includes at least one needle guide slot 218. In one example, the needle shuttle receptacle 214 includes two needle guide slots 218, which each receive a portion of the needle shuttle 128 to direct the movement of the needle shuttle 128 relative to the cradle 122. The needle shuttle receptacle 214 also includes at least one needle shuttle stop 220. In one example, the needle shuttle receptacle 214 includes two needle guide stops 220, which contact a portion of the needle shuttle 128 in the first, retracted position to prevent the further movement of the needle shuttle 128 relative to the cradle 122. In this example, with reference to FIG. 12C, the needle guide stops 220 comprise a pair of opposed cantilevered beams having a projection 220a that extends radially inward from a sidewall of the needle shuttle receptacle 214 and contacts a surface of the needle shuttle 128 to inhibit the motion of the needle shuttle 128. In this example, a pair of slots 220b (FIG. 11) are defined through the needle shuttle receptacle 214 on either side of the needle guide stops 220 to enable the needle guide stops 220 to move or flex relative to the cradle 122. Each of the needle guide stops 220 may also include an area of reduced thickness near a base of the needle guide stops 220 that forms a living hinge, thereby enabling the movement of the needle guide stops 220 relative to the cradle 122.

Figure 16:
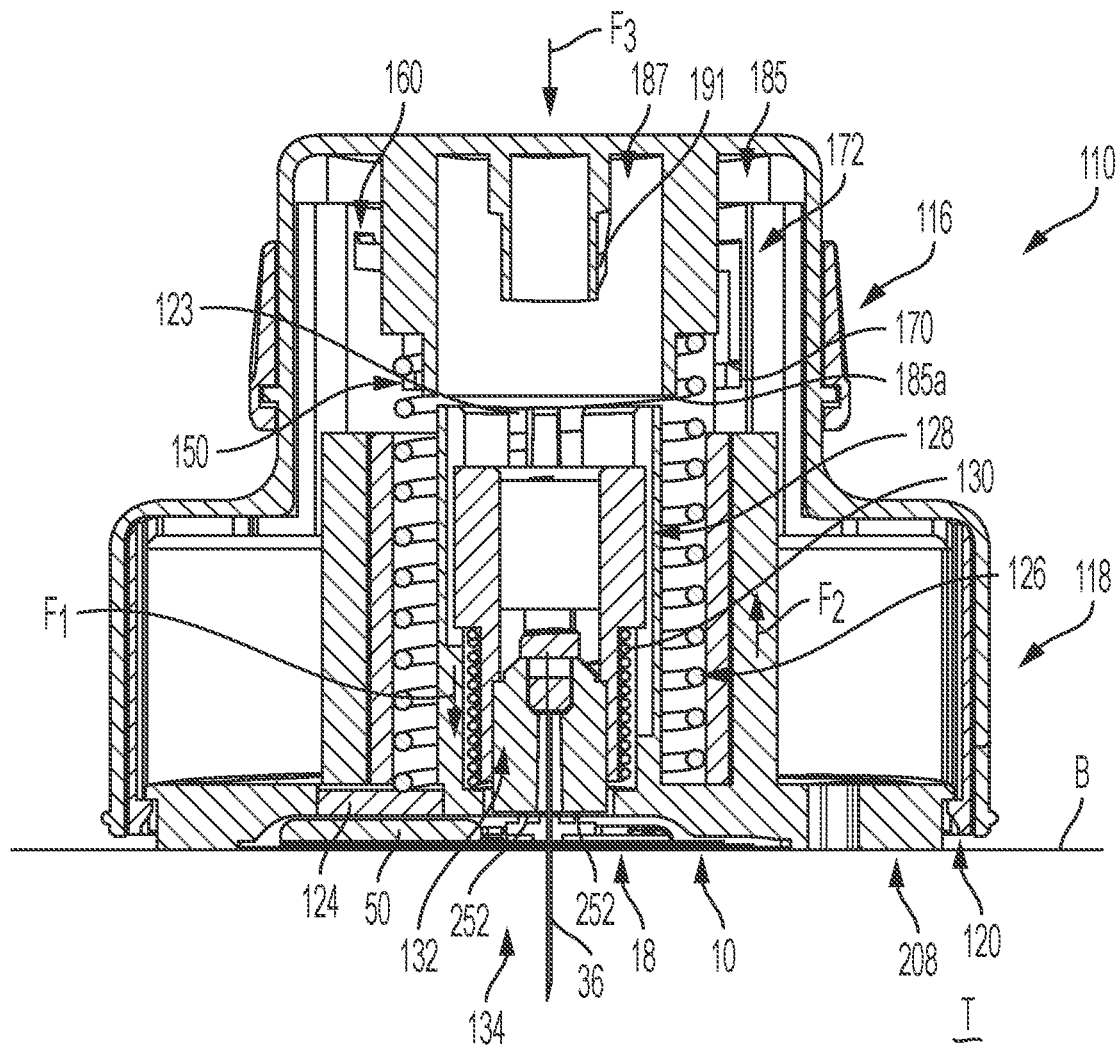
FIG. 16 is a cross-sectional view of the sensor introducer in the second, deployed position for coupling the physiological characteristic sensor assembly to a body of a user.

In this regard, with reference to FIG. 12, the needle guide stops 220 are constrained by a sidewall of the first projection 185 of the outer housing 118 in the first, retracted position. As the sensor introducer 110 moves from the first, retracted position towards the second, deployed position, the needle guide stops 220 are no longer constrained by the first projection 185 (FIG. 16). Once unconstrained, the needle guide stops 220 deflect radially outward toward the inner housing 120 due to the force of the retraction spring 130, which releases the needle shuttle 128 and enables the retraction spring 130 to drive the needle shuttle 128 into contact with the second projection 187 of the outer housing 118.

In this example, the needle shuttle receptacle 214 is defined so as to be radially inward from a sidewall 122c of the cradle 122 to define a chamber 221. The chamber 221 is defined about a perimeter of an outer surface 214a of the needle shuttle receptacle 214 and between the sidewall 122c. The chamber 221 receives the deployment spring 126.

The cradle flange 208 surrounds a second end 122b of the cradle 122, with the second end 122b opposite the first end 122a. The cradle flange 208 includes a flange lip 222 and defines a sensor recess 224 and a magnet bore 226. The flange lip 222 includes a plurality of flange lips 222 spaced apart about a perimeter of the cradle flange 208 (FIG. 12C), and each flange lip 222 extends outwardly away from the cradle flange 208 to contact the cradle tab 202 of the inner housing 120 in the second, deployed position (FIG. 16). It should be noted that the flange lip 222 may be continuous, if desired. The sensor recess 224 is defined through a bottom surface 208b of the cradle flange 208 and is sized and shaped to receive the physiological characteristic sensor assembly 10. Generally, the sensor recess 224 is sized such that the physiological characteristic sensor assembly 10 is received within the cradle 122 so that the adhesive patch 18 is flush with a surface 122d of the cradle 122. The magnet bore 226 is in communication with the sensor recess 224, and is defined through a top surface 208a of the cradle flange 208.

In one example, the magnet bore 226 is substantially annular and is sized to receive the magnet 124. Generally, the magnet bore 226 is defined through the cradle flange 208 such that when the physiological characteristic sensor assembly 10 is received within the sensor recess 224, the battery 50 of the physiological characteristic sensor assembly 10 is attracted to the magnet 124.

The magnet 124 is coupled to the magnet bore 226, via press-fit, ultrasonic welding, adhesives, etc. The magnet 124 couples or magnetically attracts the battery 50 of the physiological characteristic sensor assembly 10 to the cradle 122, which assists in coupling and retaining the physiological characteristic sensor assembly 10 within the sensor recess 224. The magnet 124 is any suitable permanent magnet, which is capable of attracting the battery 50 of the physiological characteristic sensor assembly 10 to couple the physiological characteristic sensor assembly 10 to the cradle 122 prior to the deployment of the physiological characteristic sensor assembly 10. In this example, the magnet 124 is cylindrical; however, the magnet 124 may have any desired shape.

In one embodiment, the magnet 124 cooperates with the magnet sensor 85 (FIG. 5) to initiate or activate the physiological characteristic sensor assembly 10. In this regard, as discussed, the magnet sensor 85 observes a magnetic field, such as that produced by the magnet 124. When the physiological characteristic sensor assembly 10 (which contains the magnet sensor 85) is placed inside the sensor introducer 110, the magnet 124 is in close proximity to the magnet sensor 85 and the presence of the magnetic field (provided by the magnet 124) is observed by the magnet sensor 85. The processor, which is in communication with the magnet sensor 85, processes the sensor signals and determines a magnetic field is present. Based on the determination of a magnetic field, the processor inhibits the physiological characteristic sensor assembly 10 from initiating the monitoring of BG levels with the sensor 38. Once the physiological characteristic sensor assembly 10 is placed or coupled onto the user's body and removed from the sensor introducer 110, the magnet field is removed from the proximity of the magnet sensor 85, which is observed by the magnet sensor 85. The processor, which is in communication with the magnet sensor 85, processes the sensor signals and determines the magnetic field is no longer present. Based on the determination of a lack of a magnetic field, the processor activates or initiates the physiological characteristic sensor assembly 10 to monitor the BG levels with the sensor 38.

The deployment spring 126 is a helical coil spring, which is composed of a suitable biocompatible material, such as a spring steel that is wound to form the deployment spring 126. In one example, the deployment spring 126 is a tension spring, which is received between the end 185a of the outer housing 118 and the top surface 208a of the cradle flange 208. In the first, retracted position, the deployment spring 126 is positioned between the outer housing 118 and the cradle 122, and as the sensor introducer 110 moves from the first, retracted position to the second, deployed position, the deployment spring 126 expands as the cradle 122 moves toward the second end 192b of the inner housing 120 to couple the physiological characteristic sensor assembly 10 to the user. Upon deployment of the physiological characteristic sensor assembly 10, the deployment spring 126 exerts a spring force F1 along the longitudinal axis L to move the cradle 122 toward the second end 192b of the inner housing 120 to move the sensor introducer 110 from the first, retracted position to the second, deployed position.

The needle shuttle 128 guides the needle assembly 134 into the subcutaneous tissue of the user. The needle shuttle 128 is received within the needle shuttle receptacle 214, and is substantially cylindrical. The needle shuttle 128 defines a bore 230 that extends from a first shuttle end 128*a* to a second shuttle end 128*b*. The bore 230 receives the needle cradle 132 and the needle assembly 134. The bore 230 includes a counterbore 232 that extends axially from the second shuttle end 128*b*. The counterbore 232 defines a needle cradle stop 234. The needle cradle stop 234 constrains the motion of the needle cradle 132. The bore 230 also includes a pair of guide tabs 231. The guide tabs 231 extend radially inward along an inner surface of the bore 230, which extends form the counterbore 232 to the first shuttle end 128*a*. The guide tabs 231 cooperate with the outer surface 187*c* of the second projection 187 of the outer housing 118 to rotate the needle shuttle 128 as the needle shuttle 128 moves or translates upward. In this regard, the guide tabs 231 follow with the curved surfaces 191 of the outer surface 187*c* of the outer housing 118, which results in a rotation of the needle shuttle 128.

Figure 11B:
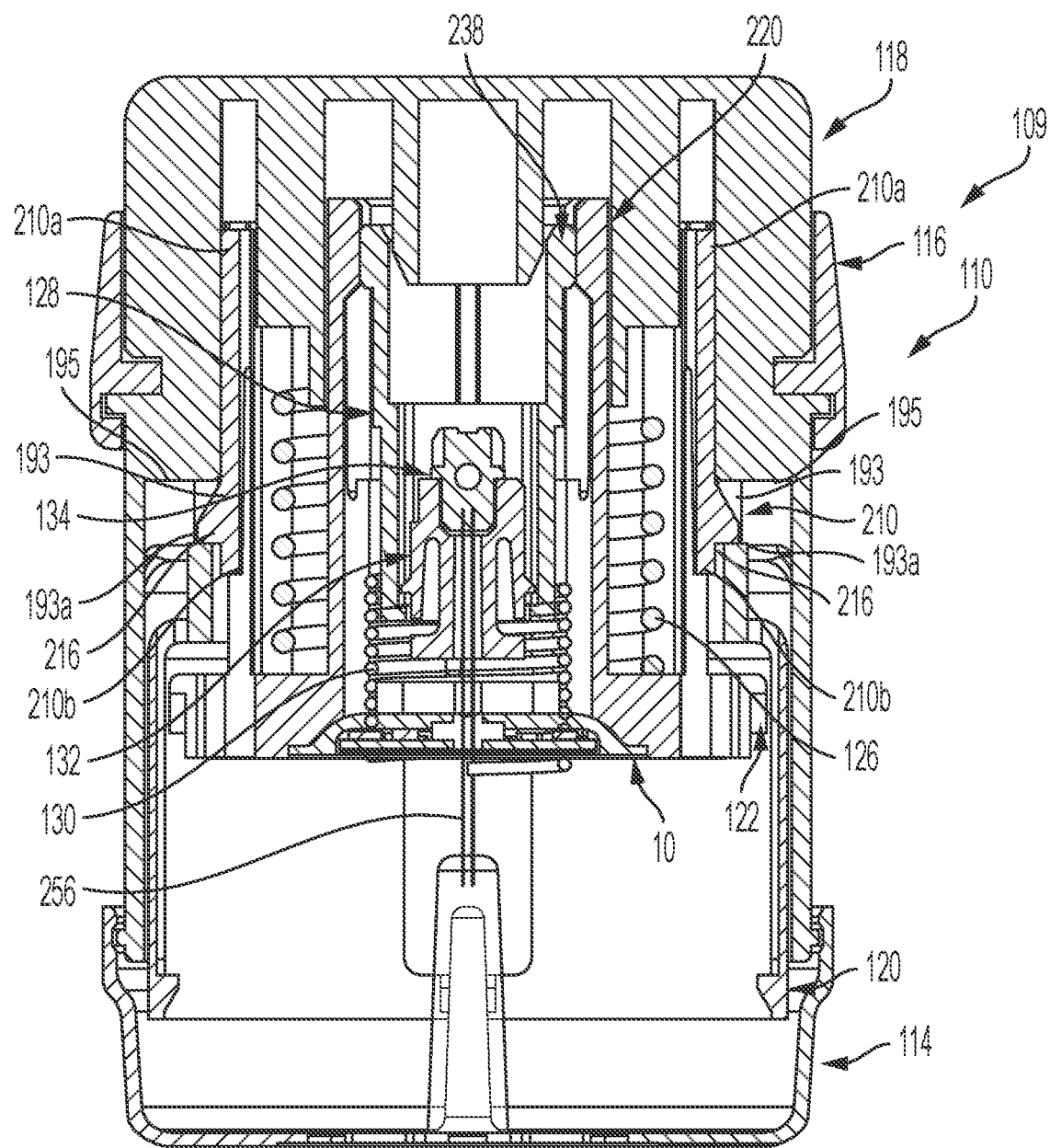
FIG. 11B is a cross-sectional view of the sensor introducer of FIG. 10, taken along line 11B-11B of FIG. 10.
Figure 18:
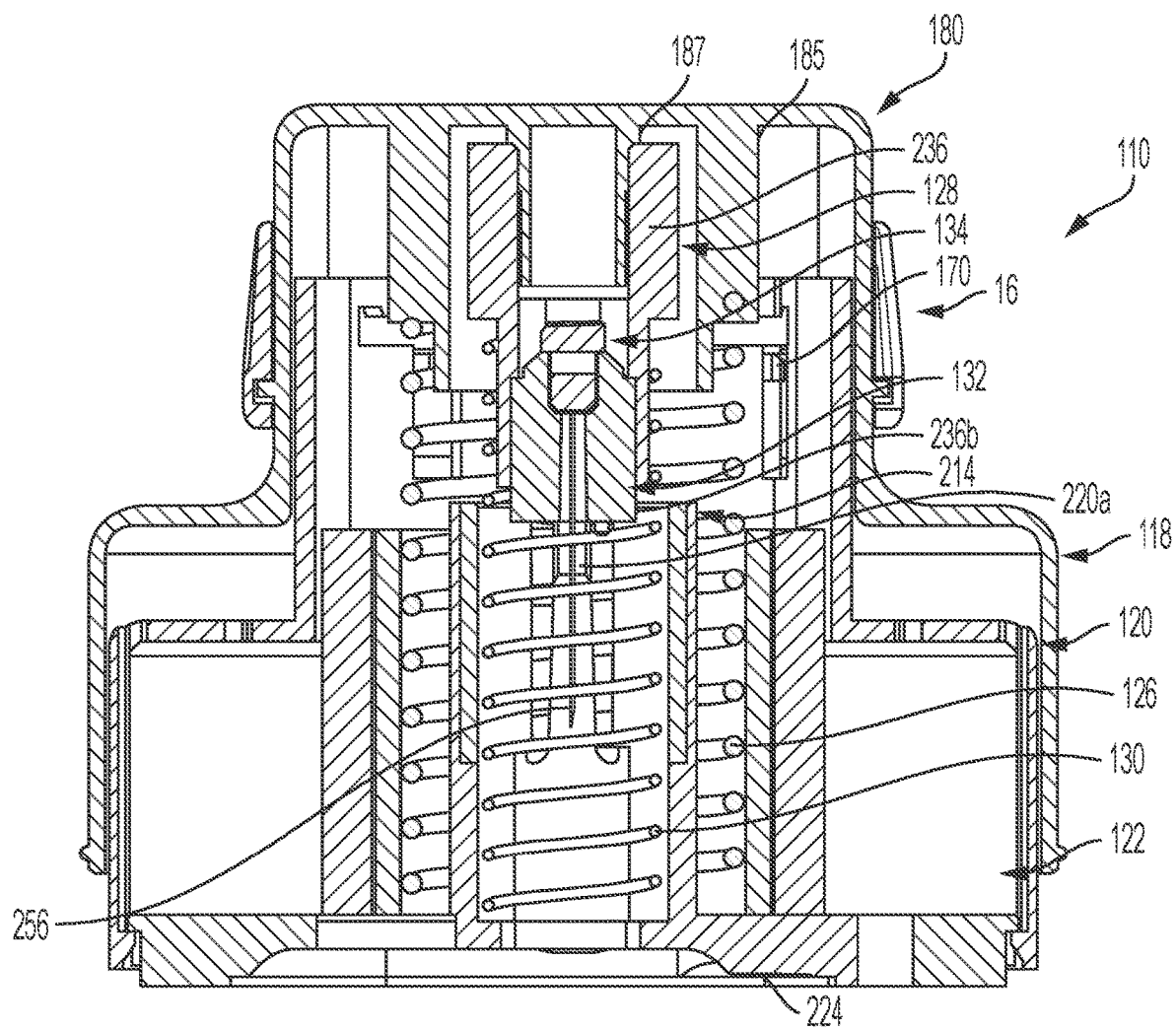
FIG. 18 is a cross-sectional view of the sensor introducer in the third, disposal position for disposing of the sensor introducer after coupling the physiological characteristic sensor assembly to a body of a user.

With reference to FIG. 11, the needle shuttle 128 also includes a pair of needle guides 236 and a pair of needle tabs 238. The needle guides 236 are slidably received within the needle guide slots 218 of the cradle 122 and cooperate with the needle guide slots 218 to direct the movement of the needle cradle 132. The needle guides 236 also cooperate to retain the retraction spring 130 within a chamber 237 defined between the needle shuttle 128 and the needle shuttle receptacle 214 of the cradle 122. The needle tabs 238 are received and restrained from liner rotation by the needle shuttle stops 220 of the cradle 122 when the introducer body 112 is in the first, retracted position (FIG. 11B). In the third, disposal position, the needle guides 236 are in contact with or rest on the cradle 122 to secure the needle assembly 134 within the cradle 122 (FIG. 18).

With reference to FIG. 12, the retraction spring 130 is a helical coil spring, which is composed of a suitable biocompatible material, such as a spring steel that is wound to form the retraction spring 130. In one example, the retraction spring 130 is a compression spring, which is received between the needle guides 236 of the needle shuttle 128 and the top surface 208*a* of the cradle flange 208. In the first, retracted position, the needle shuttle receptacle 214 is compressed between the needle shuttle 128 and the cradle 122, and as the sensor introducer 110 moves from the second, deployed position to the third, disposal position, the retraction spring 130 expands and exerts a spring force F2 along the longitudinal axis L to move the needle shuttle 128 toward the first end 122*a* of the cradle 122 to retain the needle assembly 134 within the inner housing 120.

Figure 13:
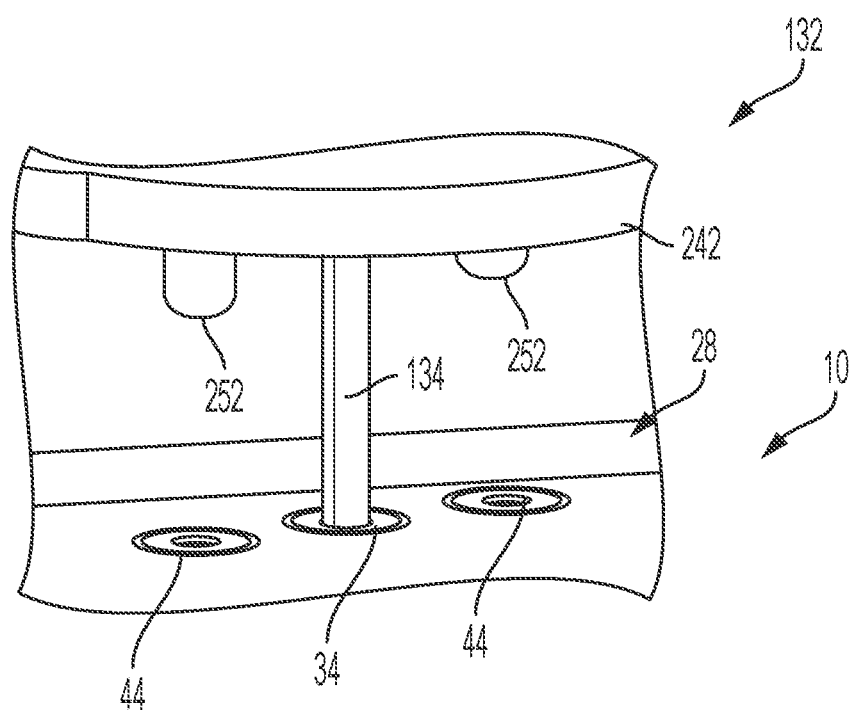
FIG. 13 is a detail perspective view of a portion of the sensor introducer for coupling with a portion of the physiological characteristic sensor assembly of FIG. 1.

The needle cradle 132 is cylindrical, and is composed of a suitable polymer-based material, and may be cast, molded, printed, etc. The needle cradle 132 includes a first cradle end 240 opposite a second cradle end 242, a bore 244 defined from the first cradle end 240 to the second cradle end 242, a pair of needle cradle guides 246 and an alignment tab 248 (FIG. 11). The first cradle end 240 includes a conical surface positioned about the bore 244 that tapers to define a top surface 250. The top surface 250 contacts the cradle stops 234 to constrain the movement of the needle cradle 132. The second cradle end 242 includes two sensor projections 252 that extend outwardly from the second cradle end 242. With reference to FIG. 13, the sensor projections 252 are sized and shaped to be received within the alignment recesses 44 of the physiological characteristic sensor assembly 10 to ensure that the needle assembly 134 is coupled to the physiological characteristic sensor assembly 10 in the proper orientation to ensure alignment with the cannulated portion 42 of the sensor 38. In one example, the sensor projections 252 are cylindrical in shape, but the sensor projections 252 can have any shape that is configured to physically couple the physiological characteristic sensor assembly 10 to the needle cradle 132.

With reference to FIG. 12, the bore 244 is defined from the first cradle end 240 to the second cradle end 242 and receives the needle assembly 134 therethrough. The bore 244 has a counterbore 244*a* that extends through the first cradle end 240 toward the second cradle end 242 to receive a needle hub 254 of the needle assembly 134. The needle hub 254 may be coupled to the needle cradle 132 via adhesives, ultrasonic welding, press-fit, etc. The needle cradle guides 246 are received within the counterbore 232 to constrain the motion of the needle cradle 132 relative to the needle shuttle 128. With reference to FIG. 11, the alignment tab 248 extends outwardly from the needle cradle 132 and engages a corresponding slot defined in the needle shuttle 128 to couple the needle cradle 132 to the needle shuttle 128 to prevent linear and rotational movement of the needle cradle 132 relative to the needle shuttle 128.

The needle assembly 134 includes the needle hub 254 and a needle 256. The needle hub 254 couples the needle 256 to the needle cradle 132. The needle hub 254 may define a flange 258, and a portion of the conical surface of the first cradle end 240 may be received under the flange 258 to assist with coupling the needle hub 254 to the needle cradle 132 (FIG. 12). The needle 256 is composed of a biocompatible metal or metal alloy, and may be solid or cannulated. One end of the needle 256 is coupled to the needle hub 254 via ultrasonic welding, adhesives, overmolding, etc. An opposite end 256*a* of the needle 256 includes a point to assist with piercing a skin of the user to introduce the distal segment end 36 of the sensor 38 into the subcutaneous tissue of the user.

Figure 12D:
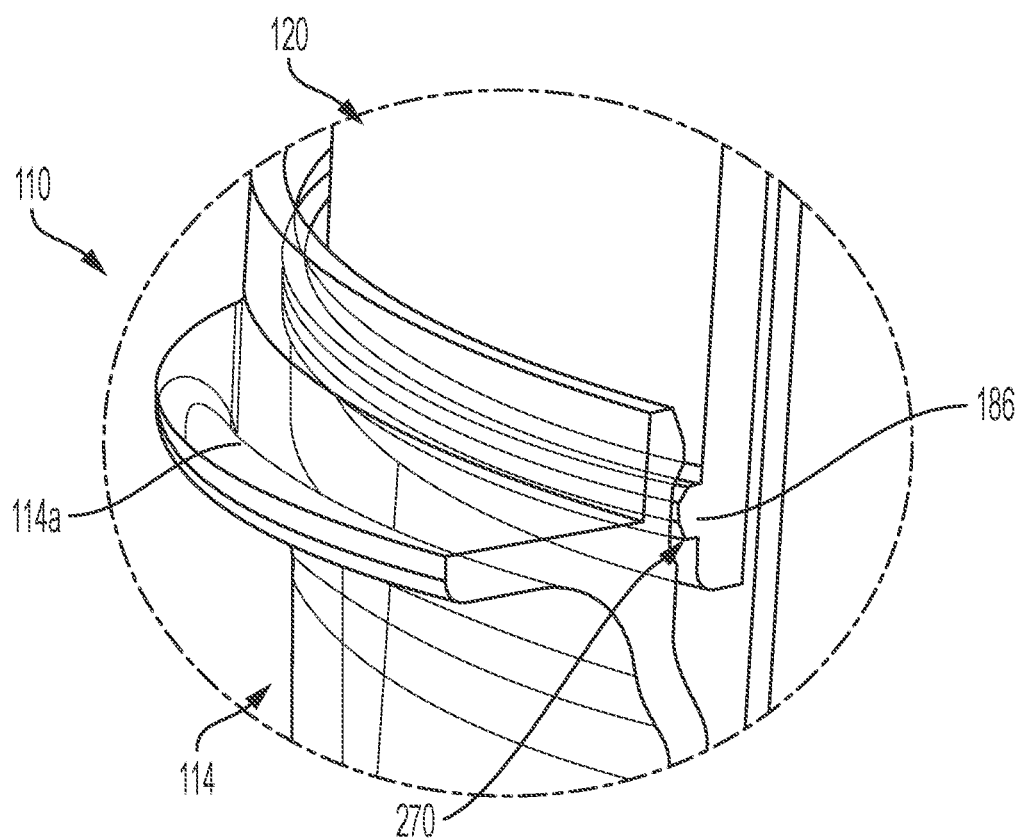
FIG. 12D is a detail view of a lid coupled to the outer housing taken at 12D on FIG. 12.

With reference to FIG. 12, the lid 114 is coupled to the lip 196 of the outer housing 118, and surrounds the first end 192*a* of the inner housing 120. The lid 114 is composed of a suitable polymer-based material, including, not limited to, silicon; and may be cast, molded, printed, etc. In one example, the lid 114 includes a base 260, a sidewall 262, a pair of posts 264 and a plurality of openings 266. The base 260 is substantially planar. The sidewall 262 extends axially about a perimeter of the base 260 to define a chamber 268. The chamber 268 receives a portion of the inner housing 120 such that the lid 114 surrounds the second end 192*b* of the inner housing 120 to enclose the opening 204 of the inner housing 120 and the opening 188 of the outer housing 118. The sidewall 262 defines a coupling flange 270. The coupling flange 270 is defined about the perimeter of the sidewall 262 and is sized to be received over the retaining lip 186 of the outer housing 118 to couple the lid 114 to the outer housing 118. With reference to FIG. 12D, a detail view of the coupling flange 270 of the lid 114 coupled to retaining lip 186 of the outer housing 118 is shown. This interface between the lid 114 and the outer housing 118 seals the internal space of the sensor introducer 110 from the ambient environment. In this example, the lid 114 includes a graspable area 114*a*, which enables a user to easily uncouple the coupling flange 270 from the retaining lip 186 to remove the lid 114 from the outer housing 118.

With reference back to FIG. 12, the posts 264 extend axially from the base 260, and are spaced apart from each other along the base 260. The posts 264 generally taper from the base 260 to a terminal end 264*a*. The terminal end 264*a* contacts the adhesive patch 18 of the physiological characteristic sensor assembly 10 to further retain the physiological characteristic sensor assembly 10 during the shipping and transport of the physiological characteristic sensor assembly 10 and sensor introducer 110. In this regard, with the lid 114 coupled to the outer housing 118, and the physiological characteristic sensor assembly 10 positioned within the sensor recess 224 and coupled to the cradle 122, the sensor introducer 110 may be used as a shipping package for the physiological characteristic sensor assembly 10. Thus, the sensor introducer 110 reduces the need for additional or separate packaging in order to ship and transport the physiological characteristic sensor assembly 10. In addition, the posts 264 enable the physiological characteristic sensor assembly 10 to be assembled within the sensor introducer 110 without a backing layer coupled to the adhesive patch 18. This enables the physiological characteristic sensor assembly 10 to be coupled to the user without requiring the removal of a backing layer, which is more convenient for the user. The plurality of openings 266 are defined through the base 260 to provide for venting. In one example, each of the openings 266 are defined through the base 260 in a circular pattern, and are disposed between the posts 264; however, the openings 266 may have any desired configuration. The plurality of openings 266 may be sealed with a polymeric layer to enable sterilization of the sensor introducer 110 and the physiological characteristic sensor assembly 10, such as a Tyvek® layer manufactured by DuPont of Wilmington, Del.

With reference to FIG. 14, a bottom view of the sensor introducer 110 is shown with the physiological characteristic sensor assembly 10 removed. As shown, the sensor recess 224 is in communication with the magnet 124, and is positioned such that the physiological characteristic sensor assembly 10, when coupled to the cradle 122, is flush with the surface 122*d* of the cradle 122. With reference to FIG. 15, a bottom view shows the physiological characteristic sensor assembly 10 received within and coupled to the cradle 122 of the sensor introducer 110 with the adhesive layer 102 exposed and uncovered. The cradle 122 is in a first position when the sensor introducer 110 is in the first, retracted position. With reference to FIG. 16, the sensor introducer 110 is shown in the second, deployed position. In order to move the sensor introducer 110 from the first, retracted position to the second, deployed position, with the sensor introducer 110 positioned on the body of the user, the collar assembly 116 is rotated clockwise such that the rail tabs 158, 170 are each received within the respective second leg 160*b*, 172*b* of the tab slots 160, 172. With the rail tabs 158, 170 in the second leg 160*b*, 172*b* of the tab slots 160, 172, a force F3 is applied by the user to the outer housing 118 that moves the outer housing 118 such that the internal flange 195 contacts the locking tabs 210 to release the cradle 122 from the inner housing 120 (FIG. 11B). Once the locking tabs 210 are released from the cradle slots 193, the deployment spring 126 applies the force F1 to the cradle 122, which moves the cradle 122 relative to the inner housing 120 toward the body B of the user, as shown in FIG. 17. In FIG. 17, the sensor introducer 110 is shown positioned on the body B of the user, with the force F3 applied to move the locking tabs 210 from the cradle slots 193 and to release the cradle 122 such that the deployment spring 126 applies the force F1 to couple the physiological characteristic sensor assembly 10 to the body B of the user.

Figure 18A:
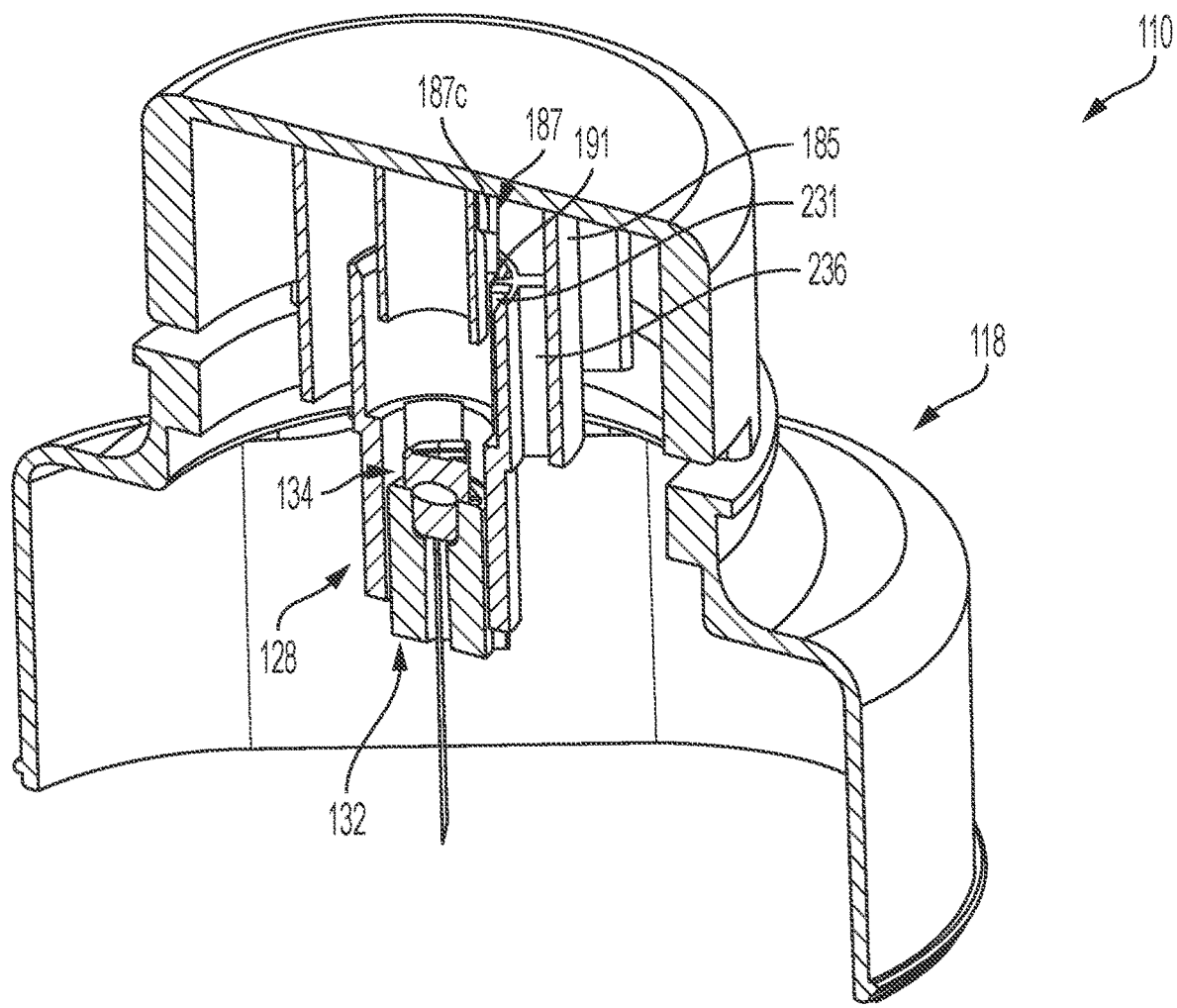
FIG. 18A is a detail view of a contact between a needle shuttle and a projection of the outer housing that causes a rotation of the needle shuttle as the sensor introducer moves from the second, deployed position to the third, disposal position, in which the cradle and an inner housing of the sensor introducer are removed for clarity.

With reference back to FIG. 16, the force F1 of the deployment spring 126 causes the cradle 122, and thus, the needle shuttle 128, the needle cradle 132 and the needle assembly 134 to move toward the body B of the user such that the end 256*a* of the needle 256 pierces the body B to insert the distal segment end 36 of the sensor 38 into subcutaneous tissue T. The cradle 122 is in a second position when the sensor introducer 110 is in the second, deployed position. After the coupling of the physiological characteristic sensor assembly 10 onto the body B of the user, with reference to FIG. 18, the sensor introducer 110 moves from the second, deployed position to the third, disposal position. Once the needle shuttle stops 220 of the cradle 122 clears a surface of the end 185*a* of the first projection 185, the spring force F2 of the retraction spring 130 causes the needle shuttle stops 220 to deflect outwardly, thereby releasing the needle shuttle 128 from the cradle 122 and the retraction spring 130 moves the needle shuttle 128, which includes the needle cradle 132 and the needle assembly 134, toward the top housing portion 180. The cradle 122 is in a third position when the sensor introducer 110 is in the third, disposal position. As the needle shuttle 128 translates toward the top housing portion 180, with reference to FIG. 18A, the curved surfaces 191 of the first projection 185 contact the guide tabs 231 of the needle shuttle 128, which causes the needle shuttle 128 to rotate slightly.

Figure 18B:
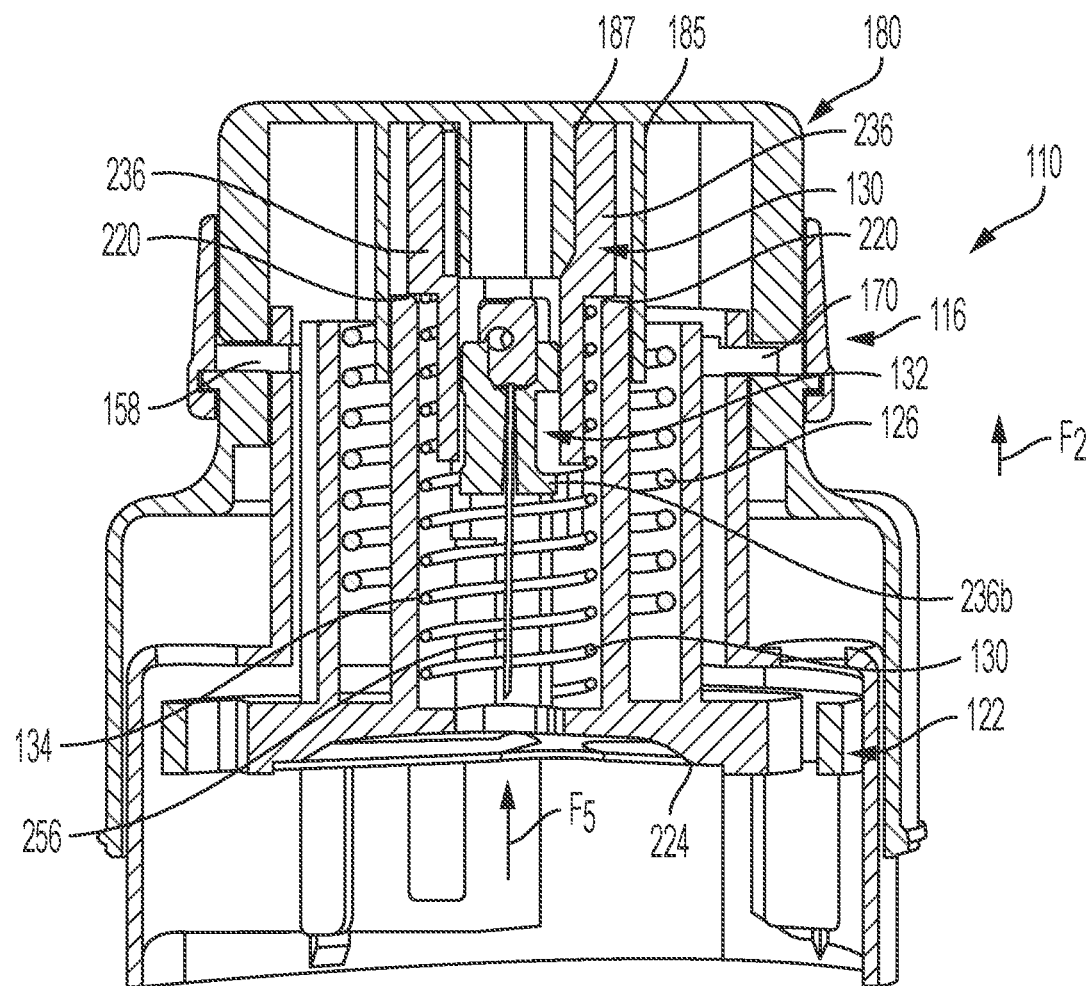
FIG. 18B is a cross-sectional view of the sensor introducer in the third, disposal position for disposing of the sensor introducer after coupling the physiological characteristic sensor assembly to a body of a user in which the cradle has been moved by the user toward the inner housing.

With reference back to FIG. 18, in the third, deployed position, the needle tabs 238 contact the cradle 122 and the needle shuttle 128 is received within the second projection 187. With the needle shuttle 128 received within the second projection 187, the needle assembly 134 is received wholly within the cradle 122 between the first end 122*a* and the cradle flange 208. This ensures that the end 256*a* of the needle 256 is disposed within the cradle 122 to ensure safe handling of the sensor introducer 110 after deployment of the physiological characteristic sensor assembly 10. In the third, disposal position, the first shuttle end 128*a* of the needle shuttle 128 is coupled to the outer housing 118. In addition, with reference to FIG. 18B, a bottom surface 236*b* of needle guide 236 inhibits motion of the needle shuttle 128, which in turn, inhibits the movement of the cradle 122 relative to the outer housing 118, and thus, prevents the distal tip or the end 256*a* of the needle 256 from being exposed when an upward force F5 (e.g. accidentally applied by the user) is applied on the cradle 122 as shown in FIG. 18B. In addition, after deployment of the physiological characteristic sensor assembly 10, with reference to FIG. 19, the sensor introducer 110 may be removed from the body B of the user leaving the physiological characteristic sensor assembly 10 coupled to the body B of the user such that the distal segment end 36 of the sensor 38 is positioned within the subcutaneous tissue.

In one embodiment, upon deployment of the physiological characteristic sensor assembly 10 onto the body B of the user, the user presses or applies a force to the push button 83. The application of the force to the push button 83 closes the push button switch pad 73, which transmits or communicates sensor signals to the processor of the controller of the physiological characteristic sensor assembly 10 for initiating the sensor 38 to monitor the BG levels of the user. The processor receives the sensor signals from the sensor 38 and transmits or communicates these sensor signals, via the antenna 52, to the remote device, including, but not limited to, an infusion pump, handheld device (tablet, smart phone, etc.) or other monitoring device.

In one embodiment, based on the observation of the ambient light, the light sensor 82 (FIG. 2) transmits or communicates sensor signals to the processor of the controller of the physiological characteristic sensor assembly 10 for initiating the sensor 38 to monitor the BG levels of the user. Upon initiation or activation, the controller receives the sensor signals from the sensor 38 and transmits or communicates these sensor signals, via the antenna 52, to the remote device, including, but not limited to, an infusion pump, handheld device (tablet, smart phone, etc.) or other monitoring device.

In one embodiment, based on the observation of the magnetic field from the magnet 124, the magnet sensor 85 (FIG. 5) transmits or communicates sensor signals to the processor of the controller of the physiological characteristic sensor assembly 10 for initiating the sensor 38 to monitor the BG levels of the user. In yet another embodiment, the physiological characteristic sensor assembly 10 be activated based on a signal or transmission received by the antenna 52 from another device, such as a signal transmitted by a near-field communication system associated with a remote device. Upon activation, the controller receives the sensor signals from the sensor 38 and transmits or communicates these sensor signals, via the antenna 52, to the remote device, including, but not limited to, an infusion pump, handheld device (tablet, smart phone, etc.) or other monitoring device.

Figure 20:
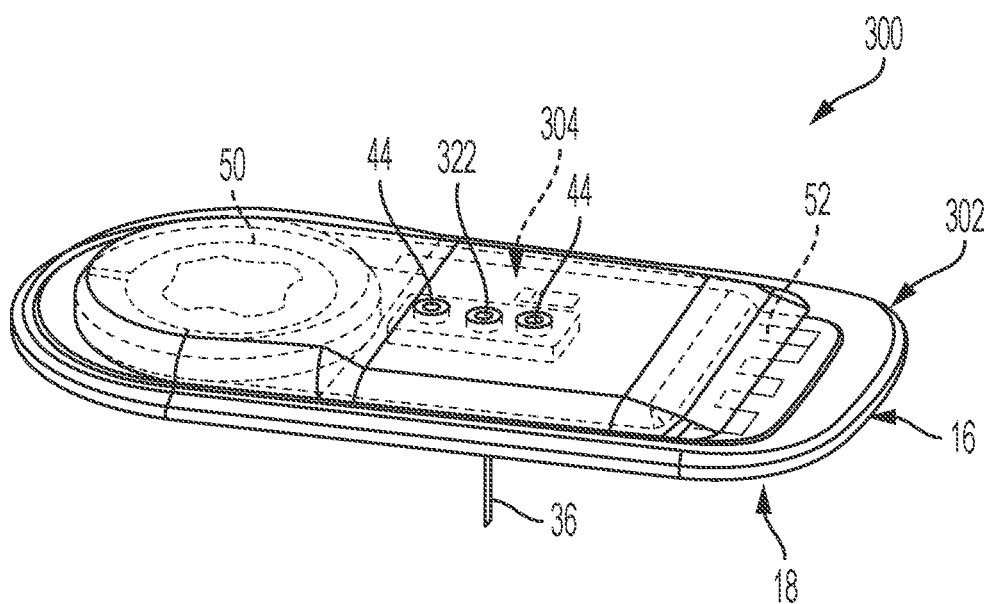
FIG. 20 is a perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 20, a physiological characteristic sensor assembly 300 is provided in accordance with various embodiments. The physiological characteristic sensor assembly 300 is flexible, and has a low profile. As the physiological characteristic sensor assembly 300 includes components that are similar or the same as the physiological characteristic sensor assembly 10 discussed with regard to FIGS. 1-9, the same reference numerals will be used to denote the same components. In one example, the physiological characteristic sensor assembly 300 includes a first or top housing 302, an electrical subsystem 304, the lower housing 16 and the coupling member or adhesive patch 18.

Figure 21:
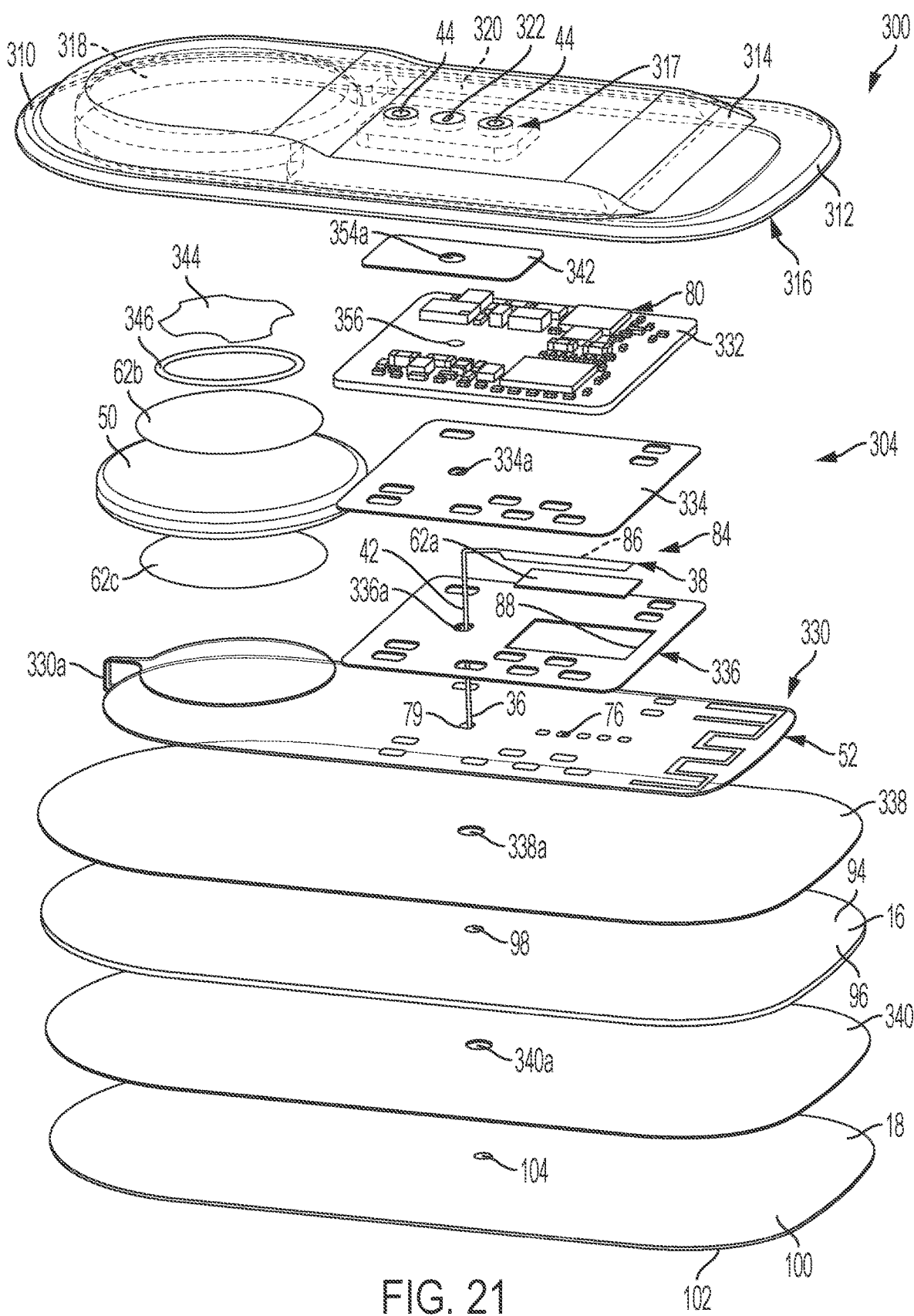
FIG. 21 is an exploded view of the physiological characteristic sensor assembly of FIG. 20.

With reference to FIG. 21, the top housing 302 is opposite the lower housing 16 and the adhesive patch 18. The top housing 302 forms a portion of an outermost surface of the physiological characteristic sensor assembly 300. The top housing 302 is flexible, and in one example is composed of a biocompatible polymer, including, but not limited to, a polyphenyl ether, thermoplastic polyurethane. The top housing 302 may be molded, three-dimensionally printed, cast, etc. The top housing 302 includes a first end 310 opposite a second end 312, a first side 314 opposite a second side 316 and a needle port 317 coupled to the top housing 302 to extend through the top housing 302 from the first side 314 to the second side 316. In one example, the first end 310 is curved or arcuate in shape, to provide a rounded edge for the user's comfort. The first end 310 also conforms to a portion of the electrical subsystem 304. The second end 312 is substantially rectangular in shape, to conform with a portion of the electrical subsystem 304. The first side 314 is substantially smooth to reduce the likelihood of catching on objects while being worn by the user. The second side 316 defines a cavity 318 and a recess 320. The cavity 318 and the recess 320 are each sized to receive a portion of the electrical subsystem 304. Generally, the cavity 318 is defined through the second side 316 proximate the first end 310 and extends towards the second end 312. The recess 320 is in communication with the cavity 318, and extends from the cavity 318 toward the second end 312.

Figure 22:
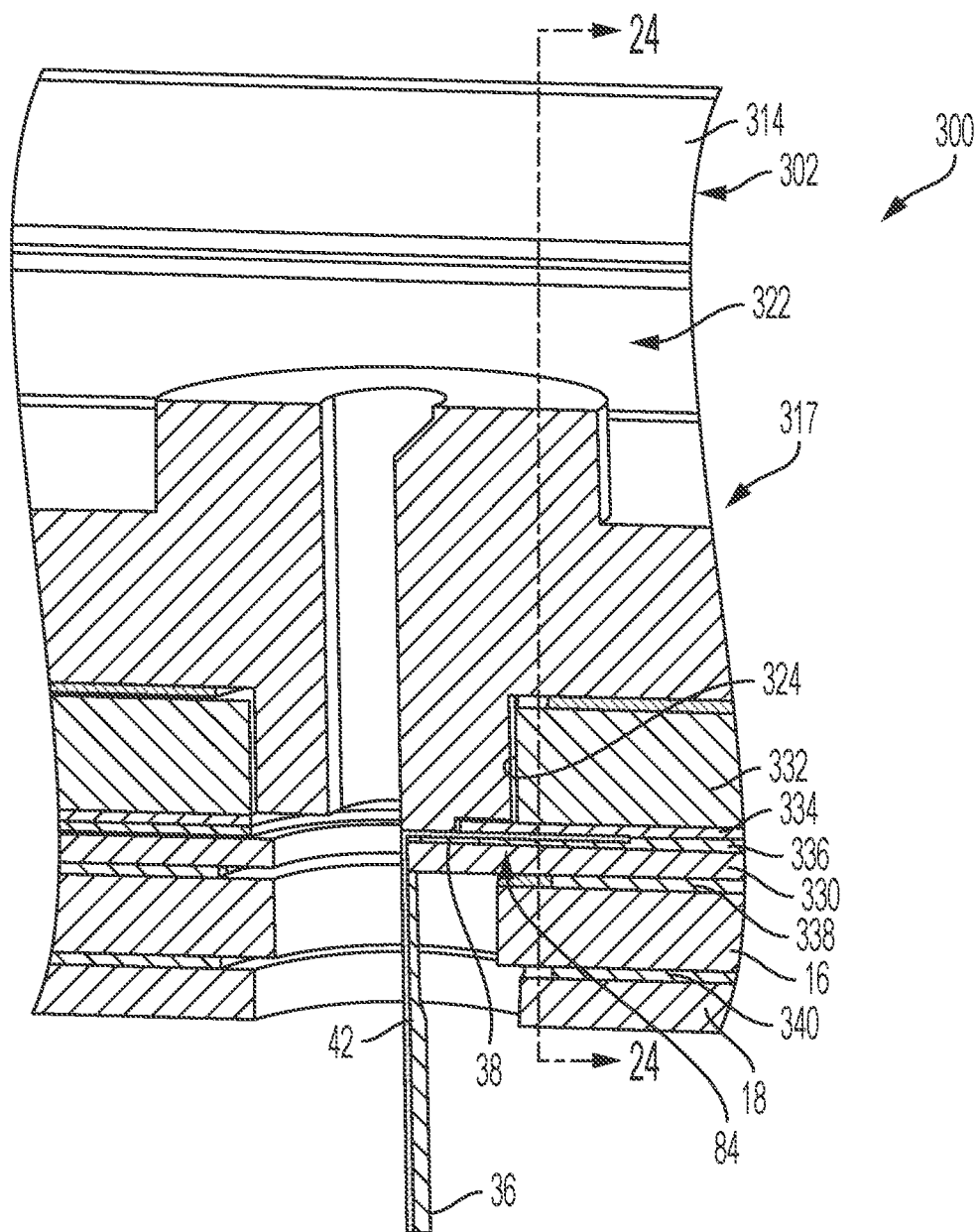
FIG. 22 is a cross-sectional view of a needle port of the physiological characteristic sensor assembly of FIG. 20, taken along line 22-22 of FIG. 20.

As will be discussed further herein, the needle port 317 cooperates with a sensor introducer, such as the sensor introducer 110 discussed with regard to FIGS. 10-19, to couple the physiological characteristic sensor assembly 300 to the body of the user. The needle port 317 is composed of a biocompatible polymer, including, but not limited to acrylonitrile butadiene styrene (ABS), polypropylene, etc. The needle port 317 is formed through molding, casting, three dimensional printing, etc., and in one example, the needle port 317 is co-molded with the top housing 302. The needle port 317 includes a central opening or port 322, which enables the needle 256 of the sensor introducer 110 (FIG. 10) to be inserted through the physiological characteristic sensor assembly 300 to insert the distal segment end 36 of the sensor 38 into subcutaneous tissue of the user. With reference to FIG. 22, a cross-section through the central port 322 is shown. The central port 322 extends from first surface 314 of the top housing 302 and into the recess 320. The central port 322 is in communication with a needle bore 324 defined through the electrical subsystem 304 and a cannulated portion 42 of the sensor 38 to insert the distal segment end 36 into the body of the user. With reference back to FIG. 21, the needle port 317 also includes the two alignment recesses 44, one on each side of the central port 322.

The electrical subsystem 304 is contained between the top housing 302 and the lower housing 16. In one example, the electrical subsystem 304 includes the battery 50, the antenna 52, a flexible printed circuit board 330, a rigid printed circuit board 332, the sensor 38, a first double sided adhesive layer 334, a second double sided adhesive layer 336, the plurality of conductive adhesive patches 62, a third double sided adhesive layer 338, a fourth double sided adhesive layer 340, a double sided adhesive tape 342, a push button 344 and a protection ring 346.

The battery 50 provides power to the various components of the electrical subsystem 304. As will be discussed, the battery 50 is electrically and physically coupled to the flexible printed circuit board 330. The antenna 52 enables wireless communication between the physiological characteristic sensor assembly 10 and another device, including, but not limited to, an infusion pump, handheld device (tablet, smart phone, etc.) or other monitoring device. In one example, the antenna 52 is a trace antenna formed on or coupled to the flexible printed circuit board 330, which is electrically coupled to the flexible printed circuit board 330. In other embodiments, the antenna 52 may be formed on and coupled to the rigid printed circuit board 332.

Figure 23:
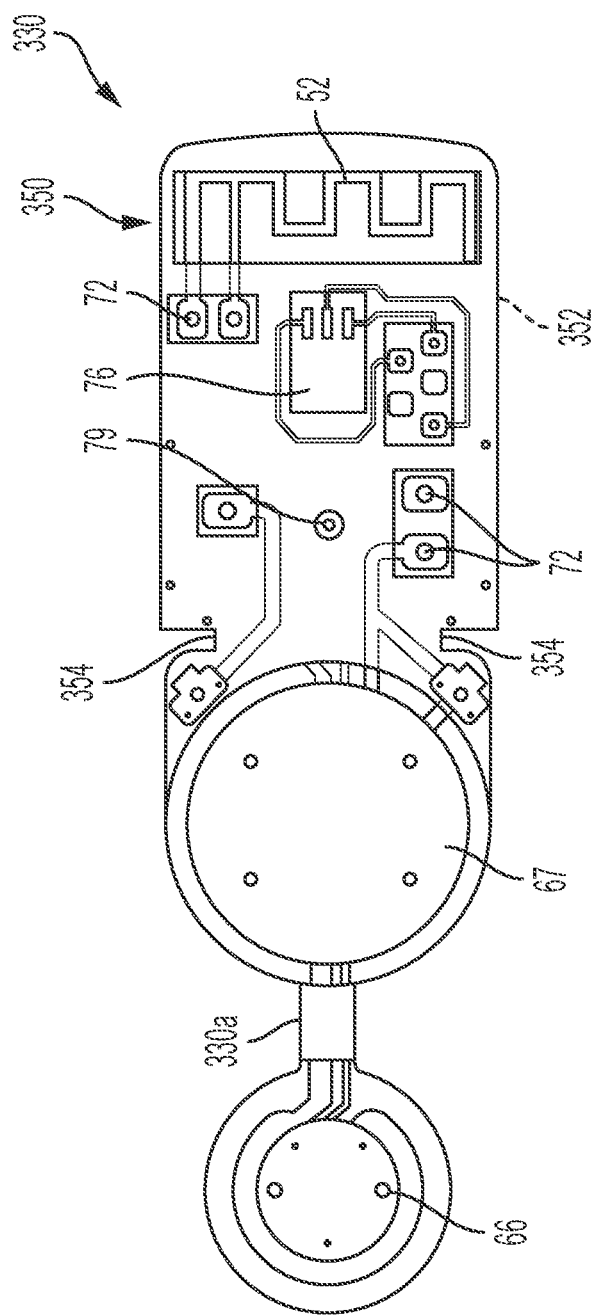
FIG. 23 is a top view of a flexible printed circuit board for use with the physiological characteristic sensor assembly of FIG. 20.

The flexible printed circuit board 330 electrically couples the battery 50 and the antenna 52 to the rigid printed circuit board 332 to enable communication between the battery 50, the antenna 52 and the electrical components 80. In one example, the flexible printed circuit board 330 is composed of a bio-compatible polymer, including, but not limited to polyimide. With reference to FIG. 23, a top surface 350 of the flexible printed circuit board 330 is shown. The top surface 350 includes the pair of battery contact pads 66, 67, the sensor contact pad 76 and the one or more contact pads 72. The battery contact pad 66 is separated by the battery contact pad 67 by a thin portion 330a of the flexible printed circuit board 330, which enables the battery contact pad 66 to be folded over on top of the battery 50. The battery contact pad 66 is sized to accommodate the push button 344. The sensor contact pad 76 electrically couples the sensor 38 to the flexible printed circuit board 330, and thus, to the rigid printed circuit board 332. The one or more contact pads 72 cooperate with a corresponding contact line and one or more contact pads on the rigid printed circuit board 332 to electrically couple the rigid printed circuit board 332 to the flexible printed circuit board 330. The flexible printed circuit board 330 also includes a bottom surface 352 opposite the top surface 350. The bottom surface 352 may include the push button switch pad 73, which accommodates the use of the push button 344. In this example, the flexible printed circuit board 54 also includes a pair of cut-outs 354 defined through the top surface 350. The cut-outs 354 cooperate to provide flexibility between the battery 50 and the rigid printed circuit board 332 when the battery 50 and the rigid printed circuit board 332 are coupled to the flexible printed circuit board 330. The flexible printed circuit board 330 also includes the sensor bore 79 defined through the top surface 350 and the bottom surface 352. The sensor bore 79 enables the needle 256 of the sensor introducer 110 (FIG. 12) to pass through the flexible printed circuit board 330 and into the cannulated portion 42 of the sensor 38.

With reference to FIG. 21, the rigid printed circuit board 332 is electrically and physically coupled to the flexible printed circuit board 54 via the first double sided adhesive layer 334 and the second double sided adhesive layer 336. The rigid printed circuit board 332 is electrically and physically coupled to the electrical components 80 associated with the physiological characteristic sensor assembly 300, and the electrical components 80 are in communication with the battery 50, the sensor 38 and the antenna 52 coupled to the flexible printed circuit board 330 via the rigid printed circuit board 332.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the flexible printed circuit board 330 via the conductive adhesive patches 62a.

Figure 24:
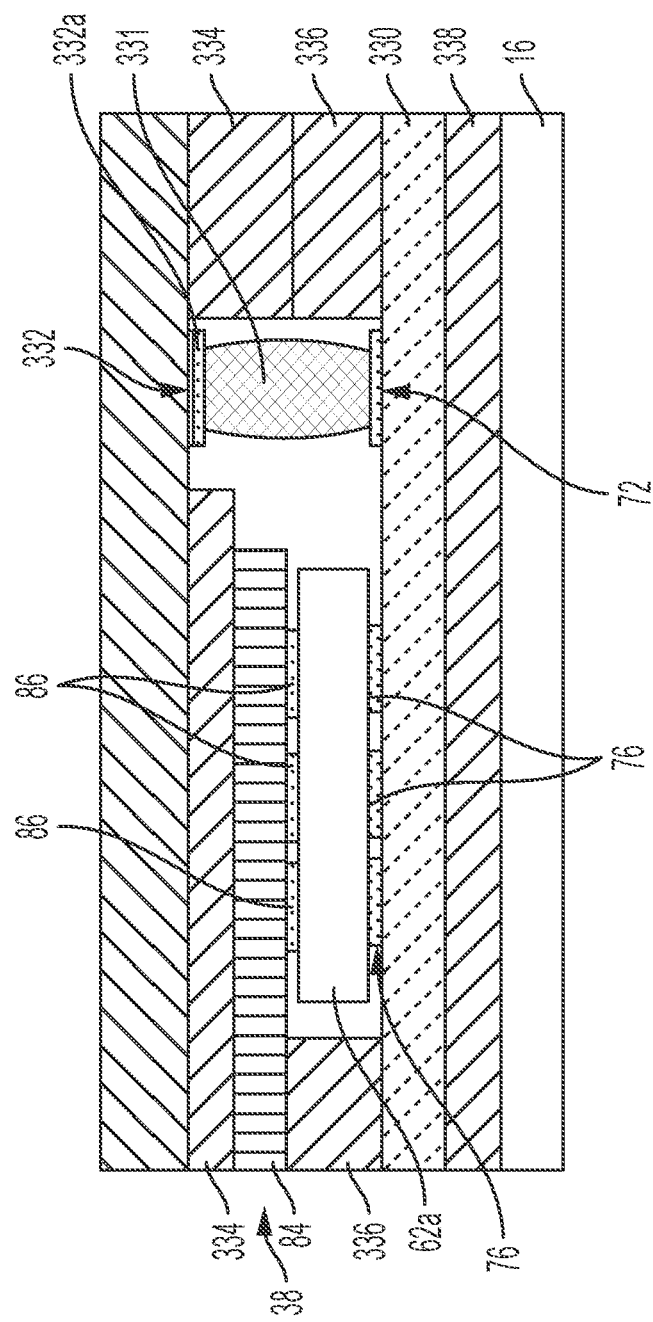
FIG. 24 is a cross-sectional view of a portion of the electrical subsystem, taken along line 24-24 of FIG. 22.

The first double sided adhesive layer 334 cooperates with the second double sided adhesive layer 336 to sandwich the sensor 38 between the double sided adhesive layers 334, 336. By sandwiching the sensor 38 between the double sided adhesive layers 334, 336, the double sided adhesive layers 334, 336 provide waterproofing around the sensor bores 79, 81 and the connection of the sensor 38 to the flexible printed circuit board 330 (via the contacts 76, 86). In this regard, with reference to FIG. 22, the double sided adhesive layers 334, 336 cooperate to seal around the central port 322, thereby inhibiting fluids from contacting the electrical subsystem 304. As shown in FIG. 22, the double sided adhesive layers 334, 336 surround the proximal end 84 of the sensor 38 to inhibit fluids that may flow through the cannulated portion 42 from contacting the connection of the sensor 38 to the flexible printed circuit board 330 and the other portions of the electrical subsystem 304. In this example, the second double sided adhesive layer 336 defines the opening 88, which is substantially rectangular to enable the proximal end 84 of the sensor 38 to be at least partially received within the opening 88 to enable the sensor 38 to be electrically coupled to the flexible printed circuit board 330, as shown in FIG. 24. FIG. 24 is a detail cross-sectional view that illustrates the connection of the sensor 38 to the flexible printed circuit board 330. In this example, the opening 88 receives the conductive adhesive patch 62a and the proximal end 84 of the sensor 38 to enable the sensor 38 to be electrically coupled to the flexible printed circuit board 330. In addition, as shown in FIG. 24, solder 331 may be used to electrically and physically couple one of the contact pads 72 of the flexible printed circuit board 330 to a contact pad 332a of the rigid printed circuit board 332.

With reference to FIG. 21, each of the double sided adhesive layers 334, 336 also includes a respective sensor bore 334a, 336a. The sensor bore 334a, 336a is defined through the double sided adhesive layers 334, 336 to enable the distal segment end 36 of the sensor 38 to pass through the double sided adhesive layers 334, 336.

The conductive adhesive patches 62a-62c electrically couple various portions of the physiological characteristic sensor assembly 300 together. As discussed, each of the conductive adhesive patches 62 comprises a Z-axis conductive adhesive, which conducts current in along the Z-axis and is generally non-conductive along the X-axis and the Y-axis. The conductive adhesive patch 62a electrically connects the sensor contact pad 76 with the sensor contacts 86 on the sensor 38. The conductive adhesive patch 62b electrically couples the battery 50 to the battery contact pad 66 (FIG. 23) on the flexible printed circuit board 330. The conductive adhesive patch 62c is circular, and electrically couples the battery 50 to the battery contact pad 67 (FIG. 23) on the flexible printed circuit board 330.

With reference to FIG. 21, the third double sided adhesive layer 338 couples the flexible printed circuit board 330 to the lower housing 16. The fourth double sided adhesive layer 340 couples the lower housing 16 to the adhesive patch 18. Each of the double sided adhesive layers 338, 340 also includes a respective sensor bore 338a, 340a. The sensor bore 338a, 340a is defined through the double sided adhesive layers 338, 340 to enable the distal segment end 36 of the sensor 38 to pass through the double sided adhesive layers 338, 340.

The double sided adhesive tape 342 waterproofs or provides a seal around the central port 322 of the needle port 317 and the sensor bore 356 of the rigid printed circuit board 332. In this example, the double sided adhesive tape 342 includes a bore 342a that is coaxially aligned with the central port 322 and the needle port 317 to provide a seal between the needle port 317 and the rigid printed circuit board 332.

Figure 25:
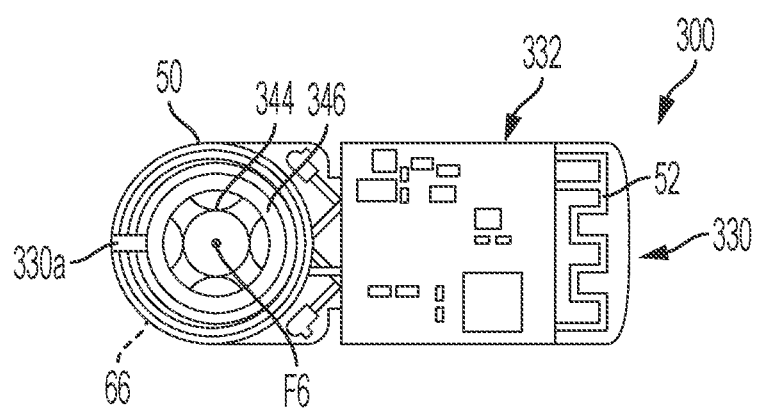
FIG. 25 is a top view of the electrical subsystem of physiological characteristic sensor assembly of FIG. 20.

The push button 344 is a tactile dome button, which enables a user to activate the physiological characteristic sensor assembly 300. In one example, with reference to FIG. 25, the push button 344 is coupled to the flexible printed circuit board 330 so as to be disposed over the battery 50. FIG. 25 is a top view of a portion of the physiological characteristic sensor assembly 300. The push button 344 is coupled to the flexible printed circuit board 330 over the battery 50 as the battery 50 provides sufficient rigidity for the user to depress the push button 344. The user depressing the push button 344, or the application of a force F6 to the push button 344 into the page on FIG. 25 causes a signal to be transmitted through the flexible printed circuit board 330 to the controller of the physiological characteristic sensor assembly 300 for initiating the sensor 38 to monitor the BG levels of the user. Stated another way, the depression of the push button 344 generates a signal that, when received by the controller, initiates the monitoring of the BG levels of the user. It should be noted, however, that the push button 344 is optional, and alternatively, a magnet sensor and a corresponding magnet on an insertion device may be used to activate the physiological characteristic sensor assembly 300, as discussed with regard to the physiological characteristic sensor assembly 10 of FIGS. 1-9.

The protection ring 346 is disposed about the push button 344, and is coupled to the flexible printed circuit board 330 so as to be disposed over the battery 50. In one example, the protection ring 346 is annular, and has a height that is slightly taller than the push button 344 to protect against accidental depression of the push button 344. Thus, the protection ring 346 ensures that the push button 344 is depressed intentionally by the user, and not inadvertently.

In one example, with reference to FIG. 21, in order to assemble the electrical subsystem 304, the electrical components 80 are electrically and physically coupled to the rigid printed circuit board 332 by a high temperature reflow soldering. With the bore 356a coaxially aligned with the sensor bore 356, the double sided adhesive tape 342 is coupled to the rigid printed circuit board 332. With the sensor bore 356 coaxially aligned with the sensor bore 334a, the first double sided adhesive layer 334 is coupled or adhered to the rigid printed circuit board 332. With the antenna 52 formed on the flexible printed circuit board 330, and the sensor bore 79 coaxially aligned with the sensor bore 336a, the second double sided adhesive layer 336 is coupled or adhered to the flexible printed circuit board 330. The conductive adhesive patch 62a is coupled to the sensor contact pad 76, and the sensor contacts 86 are coupled to the conductive adhesive patch 62a. The rigid printed circuit board 332 is positioned over the flexible printed circuit board 330 and low temperature reflow soldering is used to physically and electrically couple the rigid printed circuit board 56 to the flexible printed circuit board 54. The conductive adhesive patch 62c is coupled to the battery contact pad 67, and the battery 50 is coupled to the conductive adhesive patch 62c. The conductive adhesive patch 62b is coupled to the battery 50, so as to be coupled to a side of the battery 50 opposite a side of the battery 50 coupled to the conductive adhesive patch 62c. The battery contact pad 66 of the flexible printed circuit board 330 is folded over the battery 50. The protection ring 346 is coupled to the flexible printed circuit board 330, via adhesives, for example, so as to be disposed over the battery 50. The push button 344 is coupled to the flexible printed circuit board 330, via adhesives or ultrasonic welding, for example, so as to be received within a perimeter of the protection ring 346.

The lower housing 16 is substantially planar, and includes the sensor bore 98 defined through the lower housing 16 from the first housing side 94 to the second housing side 96. The adhesive patch 18 is coupled to the lower housing 16 and affixes the lower housing 16, and thus, the physiological characteristic sensor assembly 300, to the skin of the user. The adhesive patch 18 defines the sensor bore 104 that extends through the adhesive patch 18 from the first patch side 100 to the second patch side 102.

In one example, with continued reference to FIG. 21, with the electrical subsystem 304 assembled as discussed above and the sensor bore 79 coaxial with the sensor bore 338a, the third double sided adhesive layer 338 is coupled or adhered to the flexible printed circuit board 330. With the lower housing 16 formed and the sensor bore 98 coaxial with the sensor bore 338a, the lower housing 16 is coupled or adhered to the third double sided adhesive layer 338 such that the distal segment end 36 of the sensor 38 passes through the sensor bore 98. The top housing 302 formed with the needle port 317 co-molded with the top housing 302. The top housing 302 is positioned over the electrical subsystem 304 such that the central port 322 of the needle port 317 is coaxially aligned with the needle bore 354a. The top housing 302 is coupled to the lower housing 16, via thermal welding, for example. The sensor bore 340a of the fourth double sided adhesive layer 340 is coaxially aligned with the sensor bore 98, and the fourth double sided adhesive layer 340 is coupled or adhered to the lower housing 16. With the adhesive patch 18 formed, the adhesive layer 100a of the adhesive patch 18 is coupled or adhered to the fourth double sided adhesive layer 340 such that the distal segment end 36 extends through the sensor bore 104. The physiological characteristic sensor assembly 300 may then be deployed onto a body of the user, and the user may depress the push button 344 to initiate the monitoring of the BG levels with the sensor 38. Upon initiation or activation, the controller receives the sensor signals from the sensor 38 and transmits or communicates these sensor signals, via the antenna 52, to the remote device, including, but not limited to, an infusion pump, handheld device (tablet, smart phone, etc.) or other monitoring device.

It should be noted that in other embodiments, the sensor 38 of a physiological characteristic sensor assembly may be coupled differently to the flexible printed circuit board 54. With reference to FIG. 26, a cross-section of another exemplary mounting for the sensor 38 to the flexible printed circuit board 54 is shown. In this example, an adhesive conductive film 400 electrically and physically couples the sensor contacts 86 to the sensor contact pad 76 of the flexible printed circuit board 54. In one example, the adhesive conductive film 400 comprises a pressure sensitive adhesive with exposed conductive traces or contacts. The adhesive conductive film 400 includes a first side 402 opposite a second side 404. The first side 402 is adhesive, and with reference to FIG. 26A, the first side 402 includes a plurality of contacts 406. In this example, the first side 402 includes three rows of contacts 406, which are spaced apart from a first end 408 to a second end 410. With reference to FIG. 26B, the contacts 406 of the adhesive conductive film 400 electrically couple the sensor contacts 86 to the sensor contact pad 76 of the flexible printed circuit board 54. With reference to FIG. 26, the first side 402 is adhered to the flexible printed circuit board 54 and is coupled to the flexible printed circuit board 54 such that electrical communication is provided by the adhesive conductive film 400 between the sensor 38 and the flexible printed circuit board 54. The second side 404 is non-adhesive, and non-conductive.

In addition, it should be noted that in other embodiments, the sensor 38 of a physiological characteristic sensor assembly may be coupled differently to the flexible printed circuit board 54. With reference to FIG. 27, an exploded view provides another exemplary mounting for the sensor 38 to the flexible printed circuit board 54. In this example, the sensor 38 is mounted to the flexible printed circuit board 54 so as to be positioned between the flexible printed circuit board 54 with the rigid printed circuit board 56 positioned on top of the flexible printed circuit board 54. In this embodiment, the adhesive layer 100a of the adhesive patch 18 is shown exploded from the offset portion 100b. With reference to FIG. 27A, in this example, electrical contacts 56a on a bottom surface 56b of the rigid printed circuit board 56 are soldered to contact pads 72 on the top surface 64 of the flexible printed circuit board 54 (indicated by solder 450) to electrically and physically couple the rigid printed circuit board 56 to the flexible printed circuit board 54. The conductive adhesive patch 62a electrically and physically couples the sensor contact pad 76 to the sensor contacts 86 to enable electrical communication between the sensor 38 and the flexible printed circuit board 54.

In addition, it should be noted that in other embodiments, the sensor 38 of a physiological characteristic sensor assembly may be coupled differently to the flexible printed circuit board 330. With reference to FIG. 28, an exploded view provides another exemplary mounting for the sensor 38 to the flexible printed circuit board 330. In this example, the sensor 38 is mounted to the flexible printed circuit board 330 so as to be positioned under the rigid printed circuit board 332. In this embodiment, the battery 50 is coupled to the flexible printed circuit board 330 with contact clips 50a, 50b instead of the conductive adhesive patches 62b, 62c. In addition, the fourth double sided adhesive layer 340 has been removed, with the adhesive patch 18 directly coupled to the lower housing 16. In this embodiment, the first double sided adhesive layer 334 includes an opening 460, which corresponds with an opening 462 defined in the flexible printed circuit board 330.

With reference to FIG. 28A, in this example, the sensor contact pad 76 is disposed on the bottom surface 352 of the flexible printed circuit board 330. The sensor contact pad 76 is electrically and physically coupled to the sensor contacts 86 by the conductive adhesive patch 62a, which is positioned within the opening 462. The conductive adhesive patch 62a electrically and physically couples the sensor contact pad 76 to the sensor contacts 86 to enable electrical communication between the sensor 38 and the flexible printed circuit board 330.

It should be noted that in other embodiments, the sensor 38 of a physiological characteristic sensor assembly may be coupled differently to a printed circuit board. With reference to FIG. 29, a perspective view provides another exemplary physiological characteristic sensor assembly 500. As the physiological characteristic sensor assembly 500 includes components that are the same or similar to components of the physiological characteristic sensor assembly 10, 300, the same reference numerals will be used to denote the same or similar components. In this example, the physiological characteristic sensor assembly 500 does not include both a rigid printed circuit board and a flexible printed circuit board. Rather, the physiological characteristic sensor assembly 500 includes a flexible printed circuit board or a rigid printed circuit board 505. In this example, the sensor 38 is mounted to a top surface 505a of the printed circuit board 505. In this embodiment, the battery 50 is coupled to the printed circuit board 505 with contact clips 50a, 50b instead of the conductive adhesive patches 62b, 62c. With reference to FIG. 29A, in this example, the sensor contact pad 76 is disposed on the top surface 505a of the printed circuit board 505. The sensor contact pad 76 is electrically and physically coupled to the sensor contacts 86 by the conductive adhesive patch 62a, which is positioned within the opening 88 of the second double sided adhesive layer 336. The conductive adhesive patch 62a electrically and physically couples the sensor contact pad 76 to the sensor contacts 86 to enable electrical communication between the sensor 38 and the printed circuit board 505.

Figure 30:
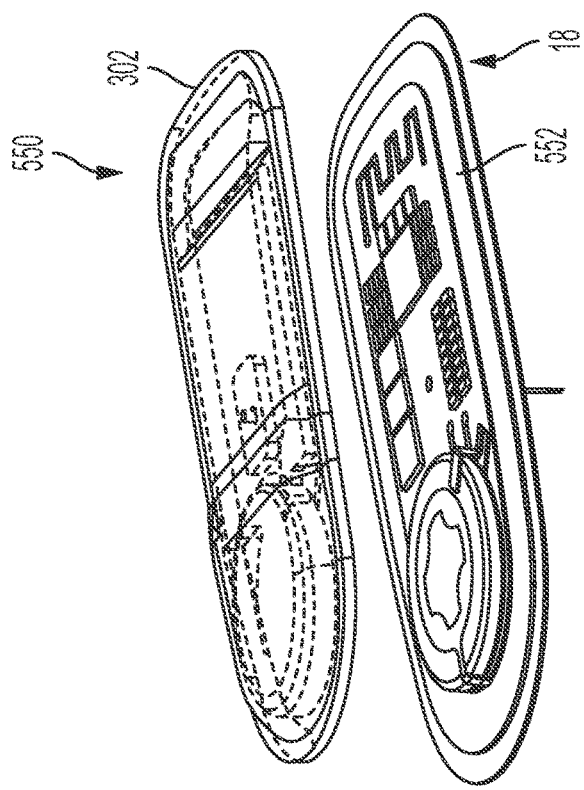
FIG. 30 is an exploded view of another exemplary mounting for a sensor of a physiological characteristic sensor assembly in accordance with various embodiments.
Figure 30A:
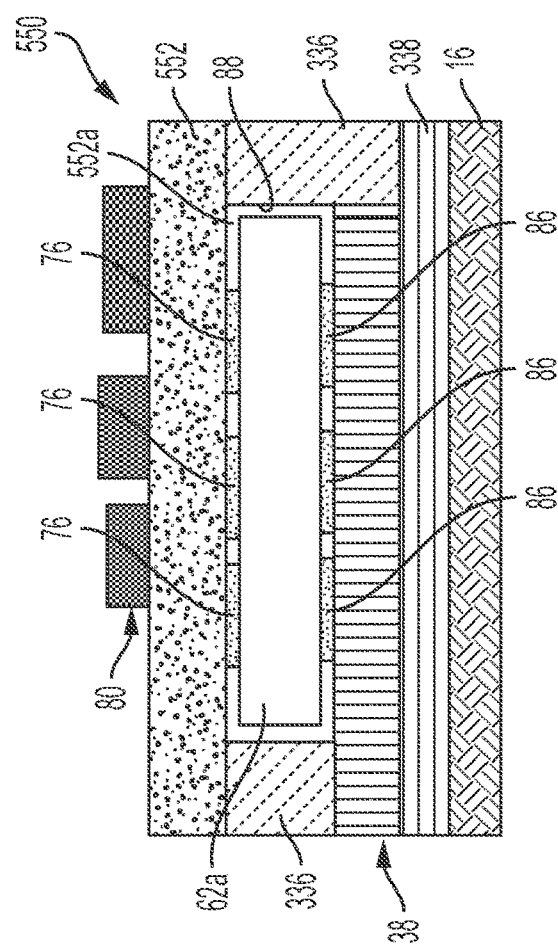
FIG. 30A is a cross-section taken through a portion of the electrical subsystem of FIG. 30, which illustrates the electrical coupling of the sensor.

It should be noted that in other embodiments, the sensor 38 of a physiological characteristic sensor assembly may be coupled differently to a printed circuit board. With reference to FIG. 30, a perspective view provides another exemplary physiological characteristic sensor assembly 550. As the physiological characteristic sensor assembly 550 includes components that are the same or similar to components of the physiological characteristic sensor assembly 10, 300, the same reference numerals will be used to denote the same or similar components. In this example, the physiological characteristic sensor assembly 500 does not include both a rigid printed circuit board and a flexible printed circuit board. Rather, the physiological characteristic sensor assembly 500 includes a flexible printed circuit board 552. In one example, the flexible printed circuit board 552 is composed of a bio-compatible polymer, including, but not limited to polyimide. The electrical components 80 associated with the rigid printed circuit board 56, 332 are electrically and physically coupled to the flexible printed circuit board 552. In this example, the sensor 38 is mounted to a bottom surface 552a of the flexible printed circuit board 552. In this embodiment, the battery 50 is coupled to the printed circuit board 505 with contact clips 50a, 50b instead of the conductive adhesive patches 62b, 62c. With reference to FIG. 30A, in this example, the sensor contact pad 76 is disposed on the bottom surface 552a of the flexible printed circuit board 552. The sensor contact pad 76 is electrically and physically coupled to the sensor contacts 86 by the conductive adhesive patch 62a, which is positioned within the opening 88 of the second double sided adhesive layer 336. The conductive adhesive patch 62a electrically and physically couples the sensor contact pad 76 to the sensor contacts 86 to enable electrical communication between the sensor 38 and the flexible printed circuit board 552.

Figure 31A:
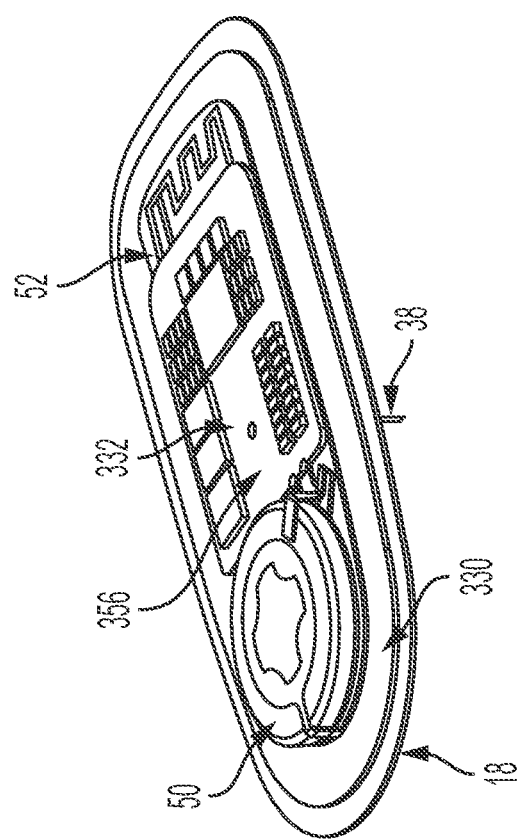
FIG. 31A is a top view of the physiological characteristic sensor assembly of FIG. 31, in which the top housing has been removed.
Figure 31:
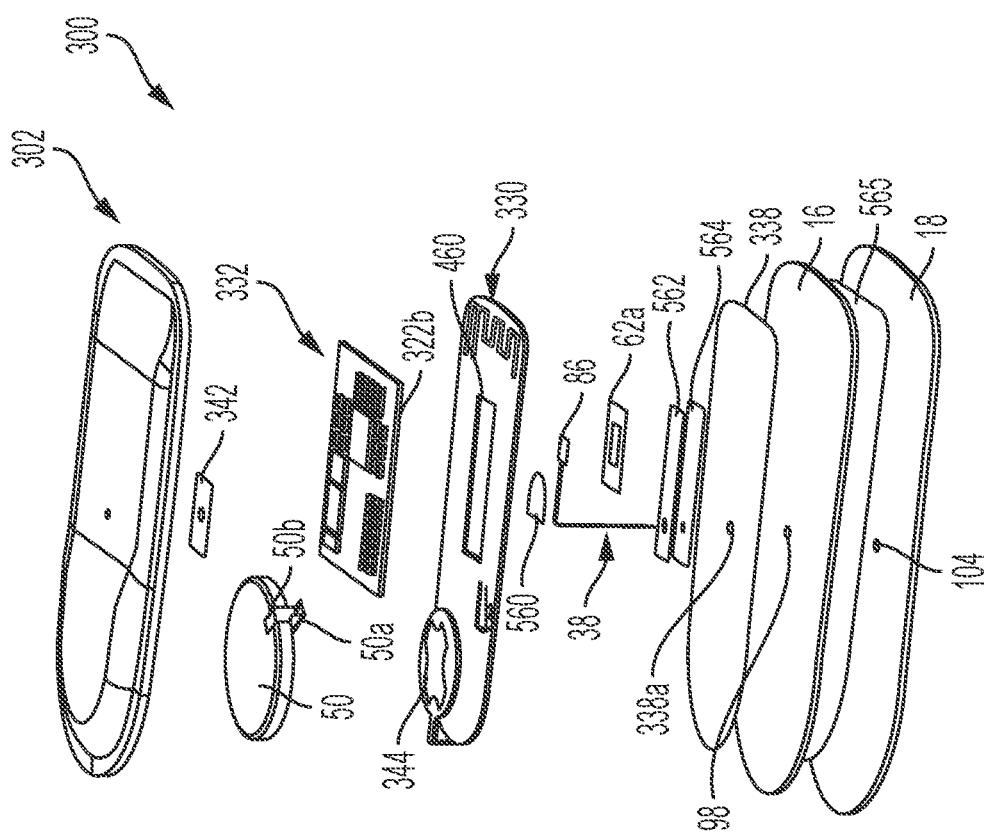
FIG. 31 is an exploded view of another exemplary mounting for a sensor of a physiological characteristic sensor assembly in accordance with various embodiments.

In addition, it should be noted that in other embodiments, the sensor 38 of a physiological characteristic sensor assembly may be coupled differently to a printed circuit board. With reference to FIGS. 31 and 31A, an exploded view provides another exemplary mounting for the sensor 38. In this example, the sensor 38 is mounted to the rigid printed circuit board 332. In this embodiment, the battery 50 is coupled to the flexible printed circuit board 330 with contact clips 50a, 50b instead of the conductive adhesive patches 62b, 62c. In this embodiment, the flexible printed circuit board 330 includes an opening 460 and the physiological characteristic sensor assembly 300 includes adhesive layers 560, 562, 564, 565. In this example, the sensor contact pad 76 is disposed on a bottom surface 332b of the rigid printed circuit board 332. The sensor contact pad 76 is electrically and physically coupled to the sensor contacts 86 by the conductive adhesive patch 62a, which is positioned within the opening 462. The conductive adhesive patch 62a electrically and physically couples the sensor contact pad 76 to the sensor contacts 86 to enable electrical communication between the sensor 38 and the flexible printed circuit board 330. Alternatively, the sensor contacts 86 may be sandwiched between the adhesive layers 562 and 564 to provide waterproofing. In this example, the sensor contacts 86 may face toward the adhesive layer 562 and the adhesive layer 562 may comprise a conductive adhesive patch, like the conductive adhesive patch 62a, to provide electrical communication between the sensor contact pad 76, the sensor contacts 86 and the flexible printed circuit board 330.

Figure 32:
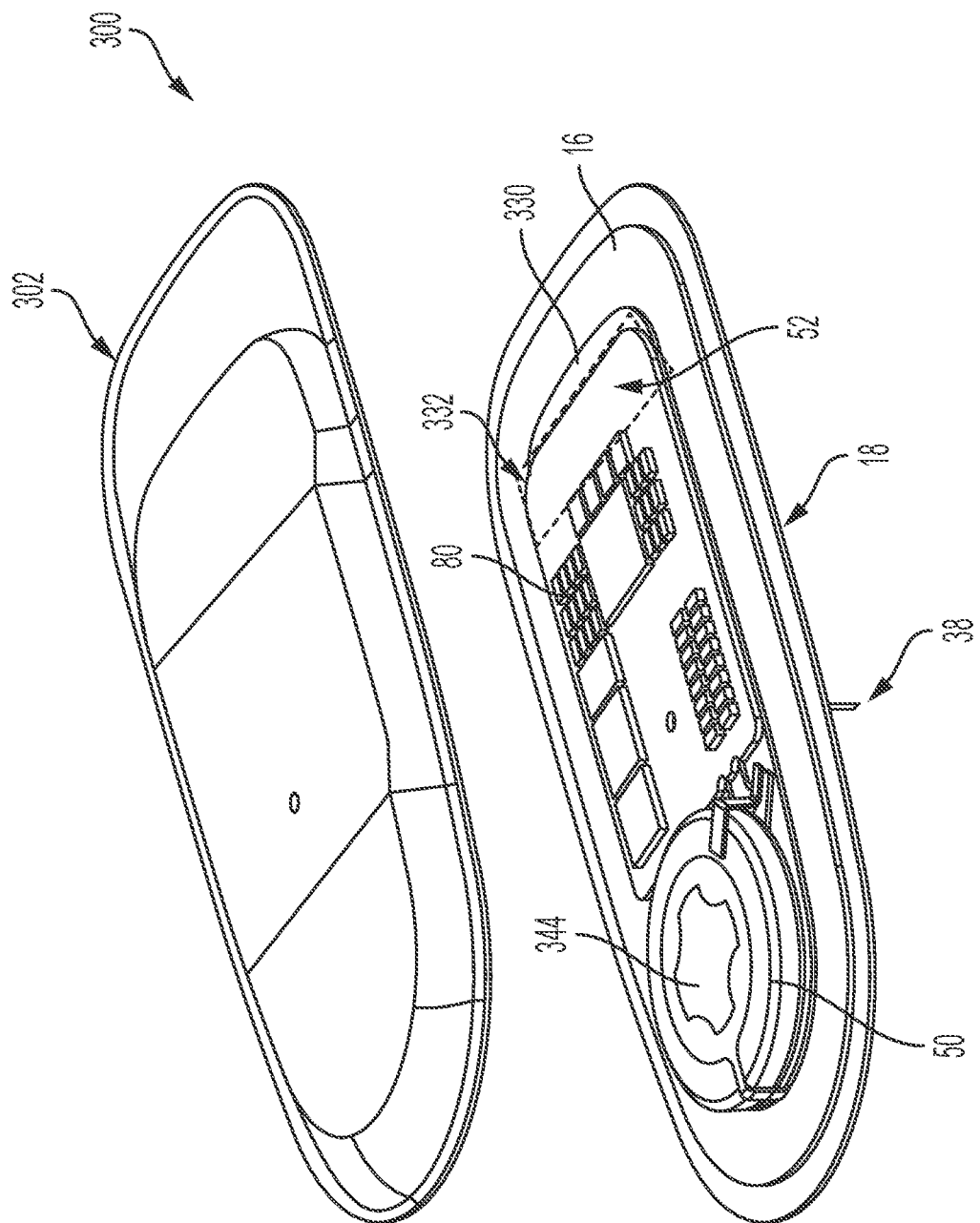
FIG. 32 is a partially exploded view of another exemplary mounting for an antenna of a physiological characteristic sensor assembly in accordance with various embodiments.

In addition, it should be noted that in other embodiments, the antenna 52 may be coupled differently to a printed circuit board. With reference to FIG. 32, a partially exploded view provides another exemplary mounting for the antenna 52 to the rigid printed circuit board 332. In this example, the antenna 52 is mounted on the rigid printed circuit board 332 along with the electrical components 80. In this embodiment, the battery 50 is coupled to the flexible printed circuit board 330 with contact clips 50a, 50b instead of the conductive adhesive patches 62b, 62c. As shown in FIG. 32, the antenna 52 is coupled to or formed on the rigid printed circuit board 332, and the rigid printed circuit board 332 is electrically coupled to the flexible printed circuit board 330.

In addition, it should be noted that in other embodiments, a printed circuit board for a physiological characteristic sensor assembly may be configured differently. With reference to FIG. 33, a top view of another exemplary printed circuit board 600 for a physiological characteristic sensor assembly is shown. In this example, the printed circuit board 600 includes a flexible printed circuit board 602 and a rigid printed circuit board 604. The rigid printed circuit board 604 is constructed as a rigid-flexible printed circuit board such that layers of the flexible printed circuit board 602 are sandwiched between layers of the rigid printed circuit board 604 as shown in FIG. 33A, which is a bottom view of the printed circuit board 600. This results in the printed circuit board 600 comprising a single component, which is both rigid and flexible, having a first flexible printed circuit board region 606, a rigid printed circuit board region 608 and a second flexible printed circuit board region 610.

Figure 34:
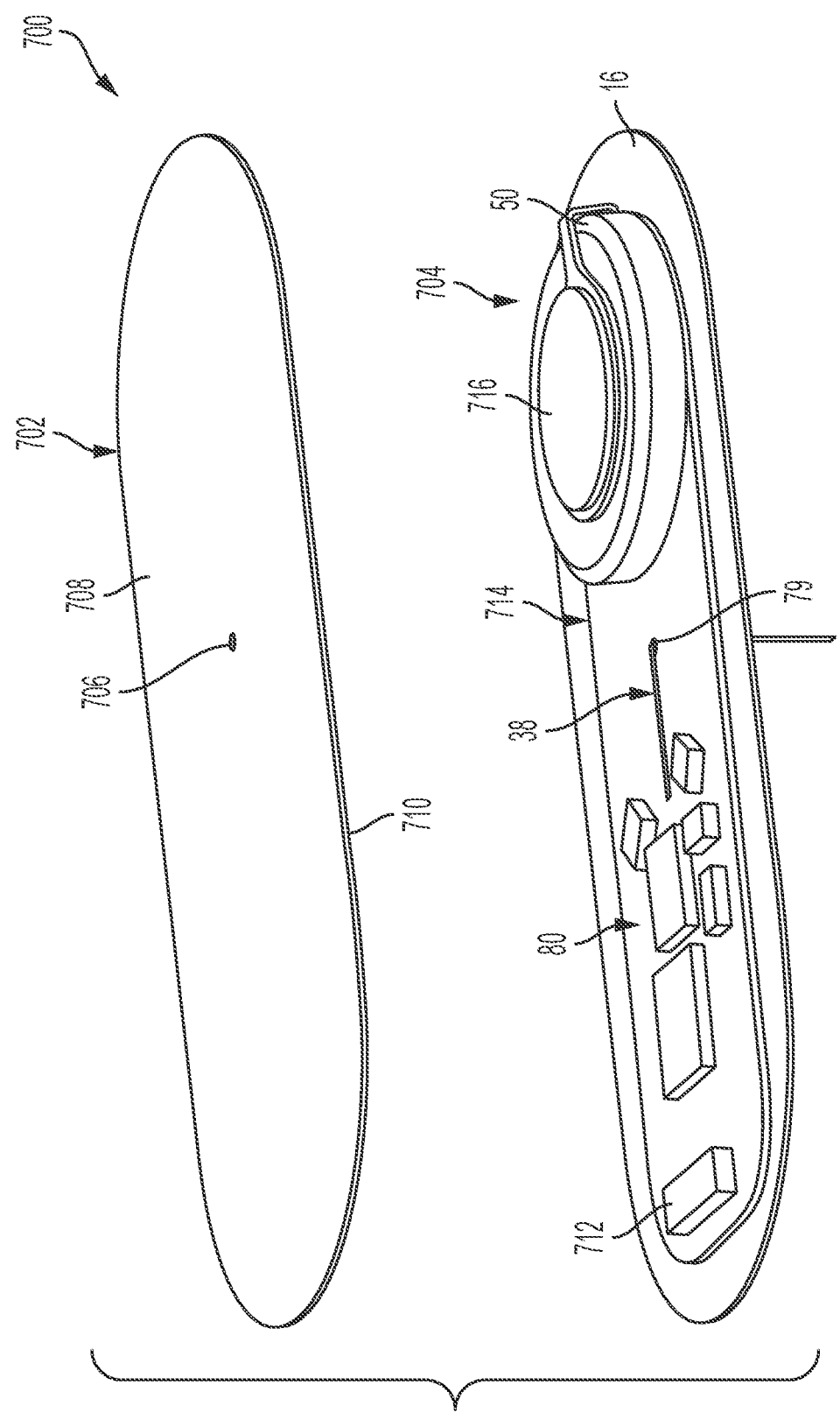
FIG. 34 is a partially exploded perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 34, a physiological characteristic sensor assembly 700 is provided in accordance with various embodiments. The physiological characteristic sensor assembly 700 is flexible, and has a low profile. As the physiological characteristic sensor assembly 700 includes components that are similar or the same as the physiological characteristic sensor assembly 10 discussed with regard to FIGS. 1-9, the same reference numerals will be used to denote the same components. In one example, the physiological characteristic sensor assembly 700 includes a first or top housing 702, an electrical subsystem 704, the lower housing 16 and the coupling member or adhesive patch 18 (not shown). The lower housing 16, in this embodiment, may comprise a thin film layer, composed of a polymer-based material, including, but not limited to, polyurethane or polyethylene terephthalate.

The top housing 702 is opposite the lower housing 16 and the adhesive patch 18. The top housing 702 forms a portion of an outermost surface of the physiological characteristic sensor assembly 700. The top housing 702 is flexible, and in one example is composed of a thin film of a biocompatible polymer, including, but not limited to, a polyurethane or polyethylene terephthalate. The top housing 702 may be molded, three-dimensionally printed, etc. The top housing 702 includes a needle bore 706 that extends through the top housing 702 from a first side 708 to a second side 710. The needle bore 706 cooperates with a sensor introducer, such as the sensor introducer 110 discussed with regard to FIGS. 10-19, to couple the physiological characteristic sensor assembly 700 to the body of the user.

The electrical subsystem 704 is contained between the top housing 702 and the lower housing 16. In one example, the electrical subsystem 704 includes the battery 50, an antenna 712, a flexible printed circuit board 714, the sensor 38, a conductive film 716 and a shim 718. The battery 50 provides power to the various components of the electrical subsystem 304. The battery 50 is electrically and physically coupled to the flexible printed circuit board 714. The antenna 712 enables wireless communication between the physiological characteristic sensor assembly 700 and another device, including, but not limited to, an infusion pump, handheld device (tablet, smart phone, etc.) or other monitoring device. In one example, the antenna 712 is a Bluetooth low energy (BLE) chip antenna that is electrically coupled to the flexible printed circuit board 714. In one example, antenna 712 may also include a near field communication (NFC) antenna and/or RF radio antenna.

Figure 35:
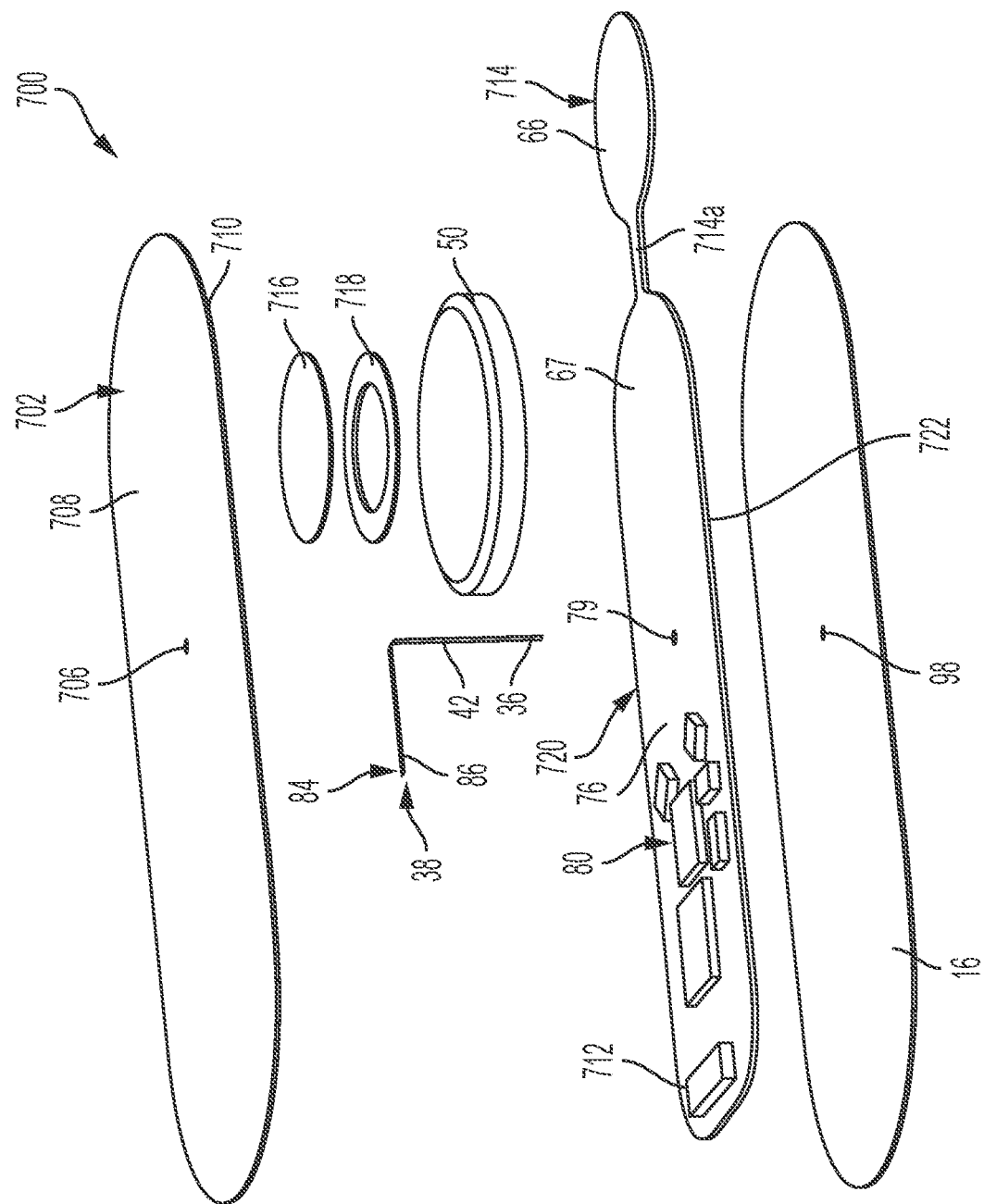
FIG. 35 is an exploded view of the physiological characteristic sensor assembly of FIG. 34.

With reference to FIG. 35, the flexible printed circuit board 714 electrically couples the battery 50 and the antenna 712 to the electrical components 80 associated with the physiological characteristic sensor assembly 700 to enable communication between the battery 50, the antenna 712 and the electrical components 80. In one example, the flexible printed circuit board 714 is composed of a bio-compatible polymer, including, but not limited to polyimide. A top surface 720 of the flexible printed circuit board 714 includes the pair of battery contact pads 66, 67, the sensor contact pad 76 and the one or more contact pads. The battery contact pad 66 is separated by the battery contact pad 67 by a thin portion 714*a* of the flexible printed circuit board 714, which enables the battery contact pad 66 to be folded over on top of the battery 50. The sensor contact pad 76 electrically couples the sensor 38 to the flexible printed circuit board 714. The flexible printed circuit board 714 also includes a bottom surface 722 opposite the top surface 720. The bottom surface 722 is coupled to the lower housing 16. The flexible printed circuit board 714 also includes the sensor bore 79 defined through the top surface 64 and the bottom surface 74. The sensor bore 79 enables the needle 256 of the sensor introducer 110 (FIG. 12) to pass through the flexible printed circuit board 714 and into the sensor 38.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the flexible printed circuit board 714.

The conductive film 716 comprises a suitable biocompatible conductive adhesive film, including, but not limited to a Z-axis conductive adhesive, for example, a pressure sensitive adhesive (PSA) transfer tape that is anisotropically electrically conductive. In this example, the conductive film 716 is composed of 3M Electrically Conductive Transfer Tape 9703, which is commercially available from 3M Company of St. Paul, Minn.; however, it will be understood that other PSA transfer tape that is anisotropically electrically conductive may be employed. The conductive film 716 electrically couples the exposed electrical traces on the surface of flexible printed circuit board 714, which triggers the power-on circuit of the flexible printed circuit board 714 to enable a user to start-up or initiate the physiological characteristic sensor assembly 700 to monitor the BG levels of the user. The shim 718 is composed of a polymer-based material, and is non-conductive. The shim 718 is coupled between the conductive film 716 and the flexible printed circuit board 714 to electrically separate the conductive film 716 from the flexible printed circuit board 714. The application of a force to the conductive film 716 (via the application of a force to the top housing 702) moves the conductive film 716 to generate a signal that is transmitted or communicated by the flexible printed circuit board 714 to the controller to initiate the sensor 38.

Figure 36:
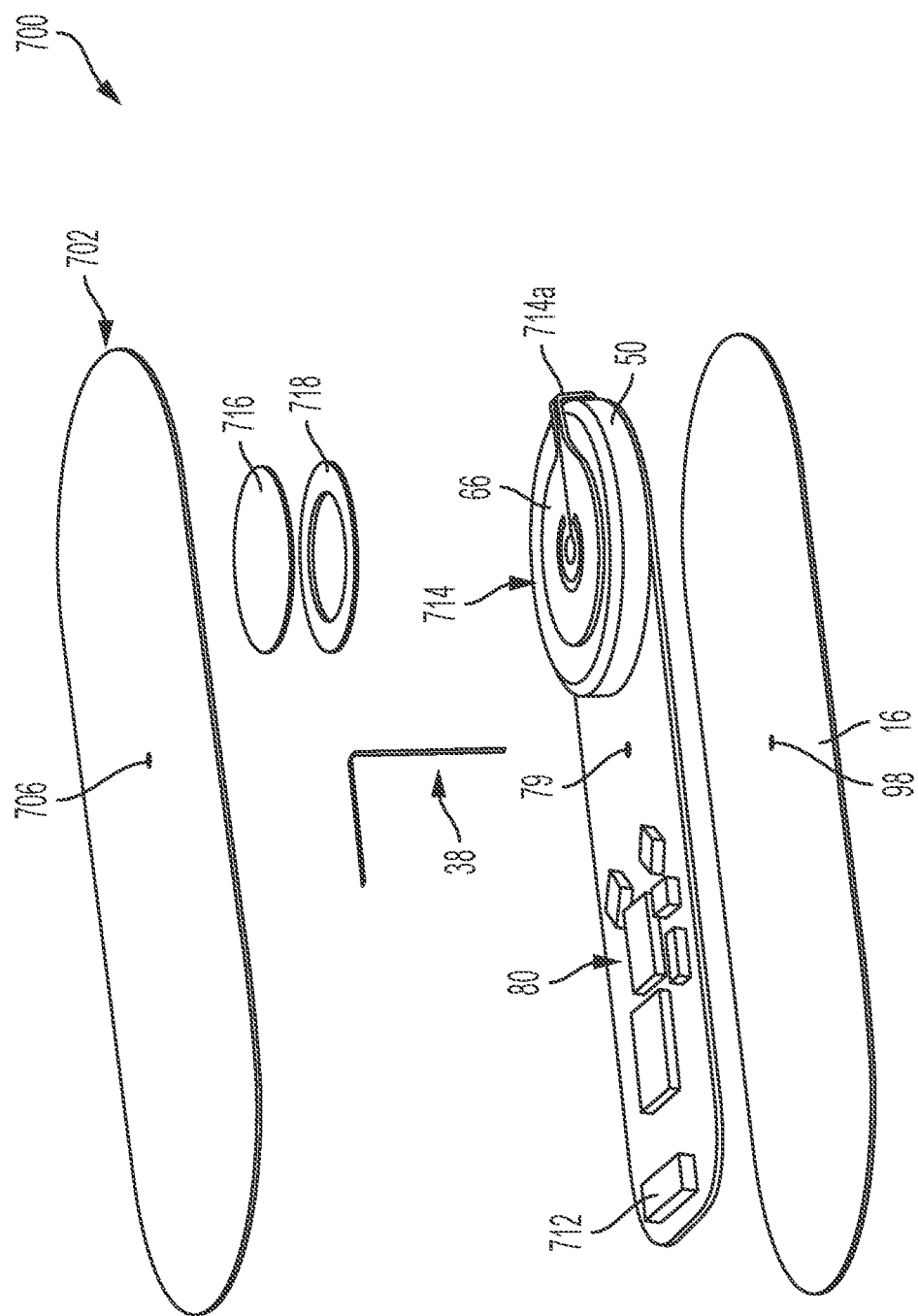
FIG. 36 is a partially exploded view of the physiological characteristic sensor assembly of FIG. 34, which illustrates an action in assembling the physiological characteristic sensor assembly of FIG. 34.

In one example, in order to assemble the physiological characteristic sensor assembly 700, the electrical components 80 are electrically and physically coupled to the flexible printed circuit board 714 by a low temperature reflow soldering. The antenna 712 is electrically and physically coupled to the flexible printed circuit board 714 by a low temperature reflow soldering. The sensor 38 is coupled to the flexible printed circuit board 714 such that the sensor contacts 86 are electrically and physically coupled to the sensor contact pad 76 of the flexible printed circuit board 714. With the sensor bore 79 coaxially aligned with the sensor bore 98, the lower housing 16 is coupled to the flexible printed circuit board 714. The battery 50 is coupled to the battery contact pad 67, and with reference to FIG. 36, the battery contact pad 66 of the flexible printed circuit board 714 is folded over the battery 50. With reference to FIG. 34, the shim 718 is coupled to the flexible printed circuit board 714, via adhesives, for example, so as to be disposed over the battery 50. The conductive film 716 is coupled to the shim 718. The top housing 702 is positioned over the electrical subsystem 704 such that the needle bore 706 is coaxially aligned with the sensor bore 79. The top housing 702 is coupled to the lower housing 16, via thermal welding, for example. The adhesive patch 18 may be coupled to the lower housing 16 for affixing the lower housing 16, and thus, the physiological characteristic sensor assembly 700, to the skin of the user. The physiological characteristic sensor assembly 700 may then be deployed onto a body of the user, and the user may depress the conductive film 716 to initiate the monitoring of the BG levels with the sensor 38. Upon initiation or activation, the controller receives the sensor signals from the sensor 38 and transmits or communicates these sensor signals, via the antenna 712, to the remote device, including, but not limited to, an infusion pump, handheld device (tablet, smart phone, etc.) or other monitoring device.

Figure 37:
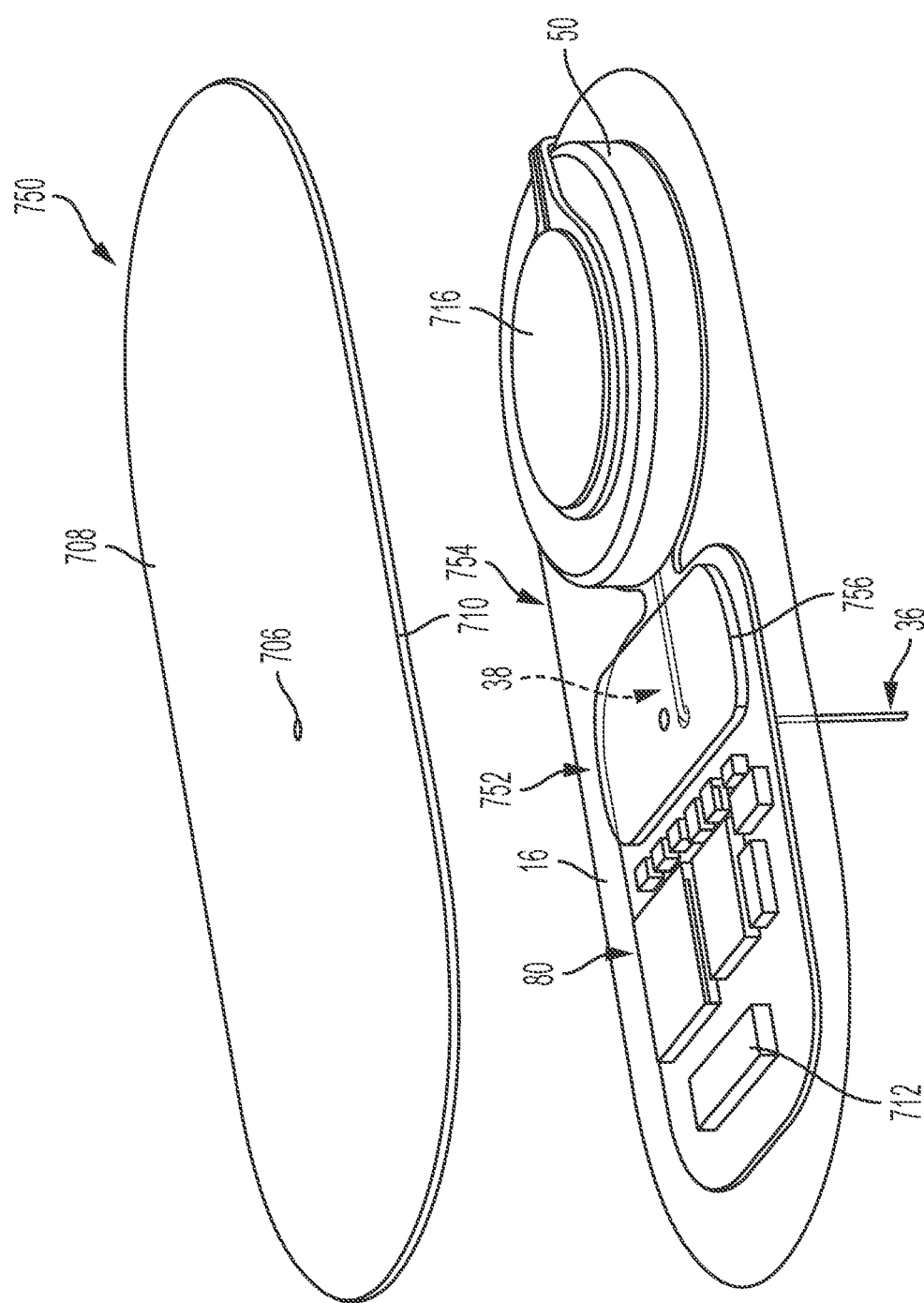
FIG. 37 is a partially exploded perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 37, a physiological characteristic sensor assembly 750 is provided in accordance with various embodiments. The physiological characteristic sensor assembly 750 is flexible, and has a low profile. As the physiological characteristic sensor assembly 750 includes components that are similar or the same as the physiological characteristic sensor assembly 10 discussed with regard to FIGS. 1-9 and the physiological characteristic sensor assembly 700 discussed with regard to FIGS. 34-36, the same reference numerals will be used to denote the same components. In one example, the physiological characteristic sensor assembly 750 includes the top housing 702, an electrical subsystem 752, the lower housing 16 and the coupling member or adhesive patch 18 (not shown). The lower housing 16, in this embodiment, may comprise a thin film layer, composed of a polymer-based material, including, but not limited to, polyurethane or polyethylene terephthalate.

The top housing 702 is opposite the lower housing 16 and the adhesive patch 18. The top housing 702 includes the needle bore 706 that extends through the top housing 702 from the first side 708 to the second side 710. The electrical subsystem 752 is contained between the top housing 702 and the lower housing 16. In one example, the electrical subsystem 752 includes the battery 50, the antenna 712, a flexible printed circuit board 754, the sensor 38, the conductive film 716, the shim 718 and a rigidizer 756. The battery 50 provides power to the various components of the electrical subsystem 752. The battery 50 is electrically and physically coupled to the flexible printed circuit board 754. The antenna 712 enables wireless communication between the physiological characteristic sensor assembly 750 and another device, including, but not limited to, an infusion pump, handheld device (tablet, smart phone, etc.) or other monitoring device.

Figure 38:
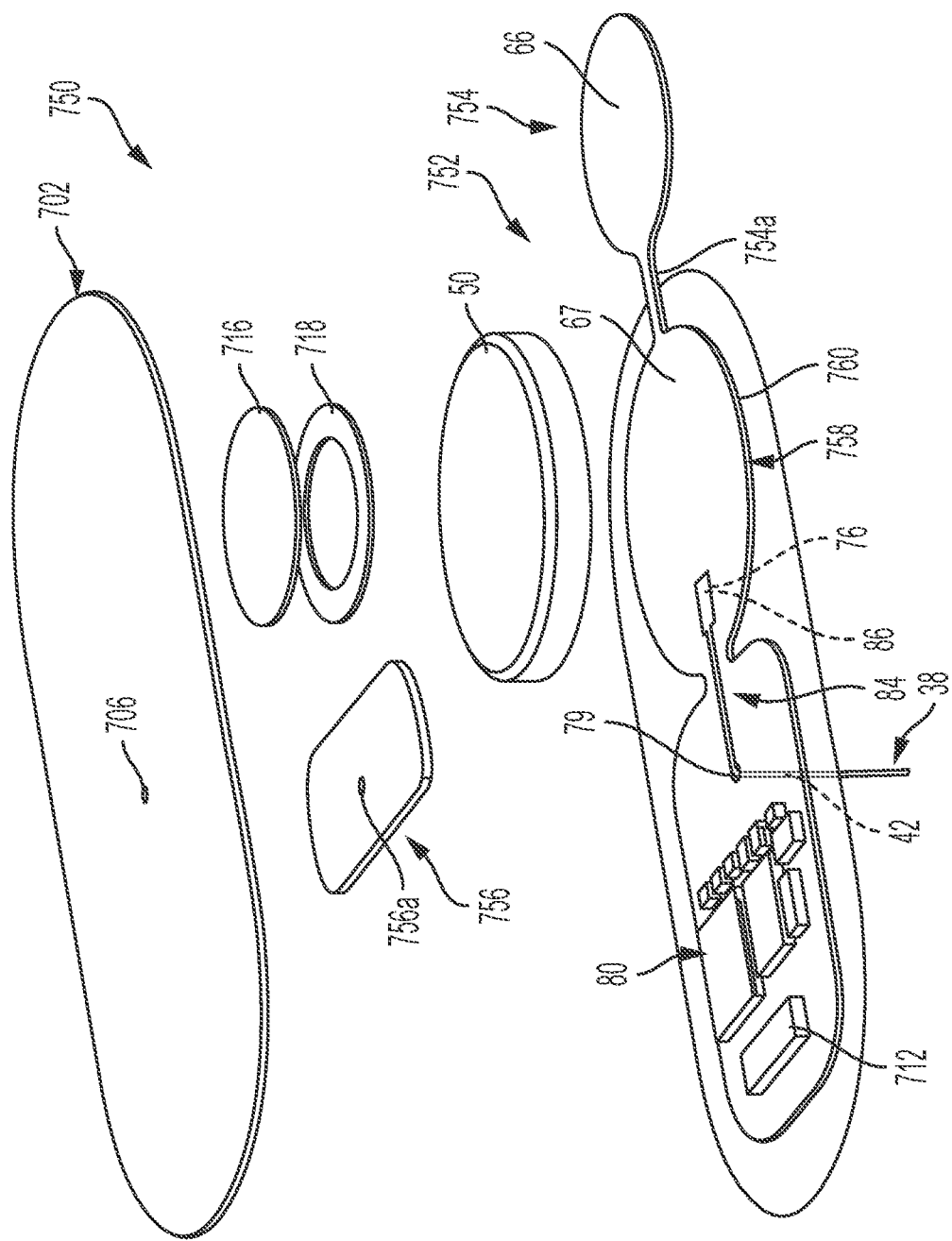
FIG. 38 is an exploded view of the physiological characteristic sensor assembly of FIG. 37.

With reference to FIG. 38, the flexible printed circuit board 754 electrically couples the battery 50 and the antenna 712 to the electrical components 80 associated with the physiological characteristic sensor assembly 750 to enable communication between the battery 50, the antenna 712 and the electrical components 80. In one example, the flexible printed circuit board 754 is composed of a bio-compatible polymer, including, but not limited to polyimide. A top surface 758 of the flexible printed circuit board 754 includes the pair of battery contact pads 66, 67, the sensor contact pad 76 and the one or more contact pads. The battery contact pad 66 is separated by the battery contact pad 67 by a thin portion 754a of the flexible printed circuit board 754, which enables the battery contact pad 66 to be folded over on top of the battery 50. The sensor contact pad 76 electrically couples the sensor 38 to the flexible printed circuit board 754. The flexible printed circuit board 754 also includes a bottom surface 760 opposite the top surface 758. The bottom surface 760 is coupled to the lower housing 16. The flexible printed circuit board 754 also includes the sensor bore 79 defined through the top surface 758 and the bottom surface 760. The sensor bore 79 enables the needle 256 of the sensor introducer 110 (FIG. 12) to pass through the flexible printed circuit board 754 and into the sensor 38.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the flexible printed circuit board 754. The conductive film 716 electrically couples the top housing 702 to the flexible printed circuit board 754 to enable a user to start-up or initiate the physiological characteristic sensor assembly 700 to monitor the BG levels of the user. The shim 718 is coupled between the conductive film 716 and the flexible printed circuit board 754 to electrically separate the conductive film 716 from the flexible printed circuit board 754.

The rigidizer 756 is coupled to the flexible printed circuit board 754 so as to be positioned over a portion of the sensor 38 and between the battery 50 and the electrical components 80. The rigidizer 756 may be coupled to the flexible printed circuit board 754 via any suitable technique, including, adhesives, ultrasonic welding, etc. In one example, the rigidizer 756 is composed of a rigid polymer based material, including, but not limited to acrylonitrile butadiene styrene (ABS), polypropylene, etc. The rigidizer 756 assists in maintaining the coupling of the sensor 38 to the flexible printed circuit board 754. In this embodiment, the rigidizer 756 provides a larger rigid area, so that in the case on an external load that is applied to the physiological characteristic sensor assembly 750 while the user is wearing the physiological characteristic sensor assembly 750, the load will be distributed across the area occupied by the rigidizer 756 rather than focused directly on the sensor 38. The rigidizer 756 defines a needle bore 756a that extends through the rigidizer 756 to enable the needle 256 of the sensor introducer 110 (FIG. 12) to pass through the rigidizer 756 and into the sensor 38.

Figure 39:
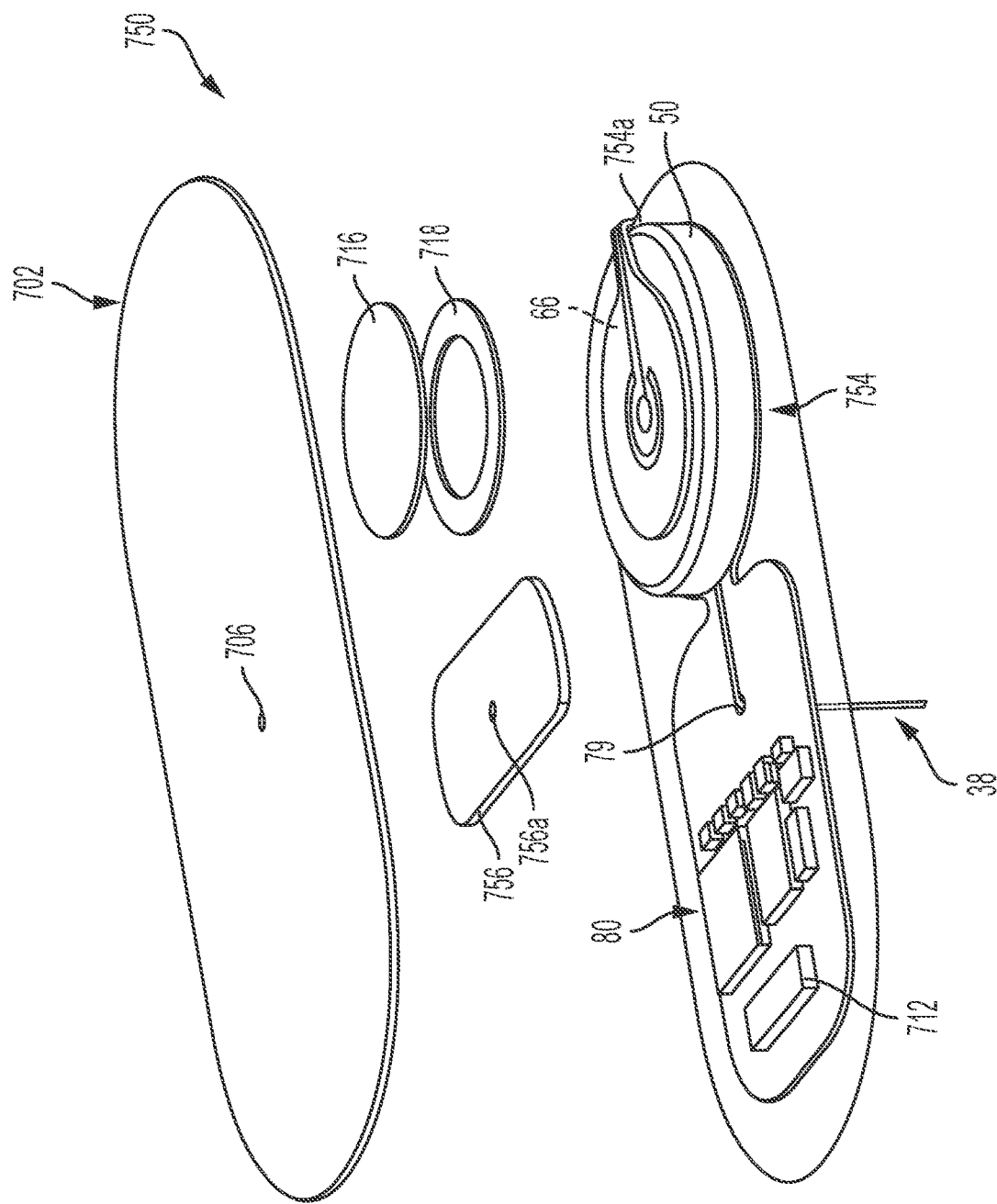
FIG. 39 is a partially exploded view of the physiological characteristic sensor assembly of FIG. 37, which illustrates an action in assembling the physiological characteristic sensor assembly of FIG. 37.

In one example, in order to assemble the physiological characteristic sensor assembly 750, the electrical components 80 are electrically and physically coupled to the flexible printed circuit board 754 by a low temperature reflow soldering. The antenna 712 is electrically and physically coupled to the flexible printed circuit board 754 by a low temperature reflow soldering. The sensor 38 is coupled to the flexible printed circuit board 754 such that the sensor contacts 86 are electrically and physically coupled to the sensor contact pad 76 of the flexible printed circuit board 754. With the sensor bore 79 coaxially aligned with the sensor bore 98, the lower housing 16 is coupled to the flexible printed circuit board 754. The battery 50 is coupled to the battery contact pad 67, and with reference to FIG. 39, the battery contact pad 66 of the flexible printed circuit board 714 is folded over the battery 50. The rigidizer 756 is coupled to the flexible printed circuit board 754 so as to be disposed over a portion of the proximal end 84 of the sensor 38. With reference to FIG. 34, the shim 718 is coupled to the flexible printed circuit board 754, via adhesives, for example, so as to be disposed over the battery 50. The conductive film 716 is coupled to the shim 718. The top housing 702 is positioned over the electrical subsystem 752 such that the needle bore 706 is coaxially aligned with the sensor bore 79. The top housing 702 is coupled to the lower housing 16, via thermal welding, for example. The adhesive patch 18 may be coupled to the lower housing 16 for affixing the lower housing 16, and thus, the physiological characteristic sensor assembly 750, to the skin of the user. The physiological characteristic sensor assembly 750 may then be deployed onto a body of the user, and the user may depress the conductive film 716 to initiate the monitoring of the BG levels with the sensor 38. Upon initiation or activation, the controller receives the sensor signals from the sensor 38 and transmits or communicates these sensor signals, via the antenna 712, to the remote device, including, but not limited to, an infusion pump, handheld device (tablet, smart phone, etc.) or other monitoring device.

Figure 40:
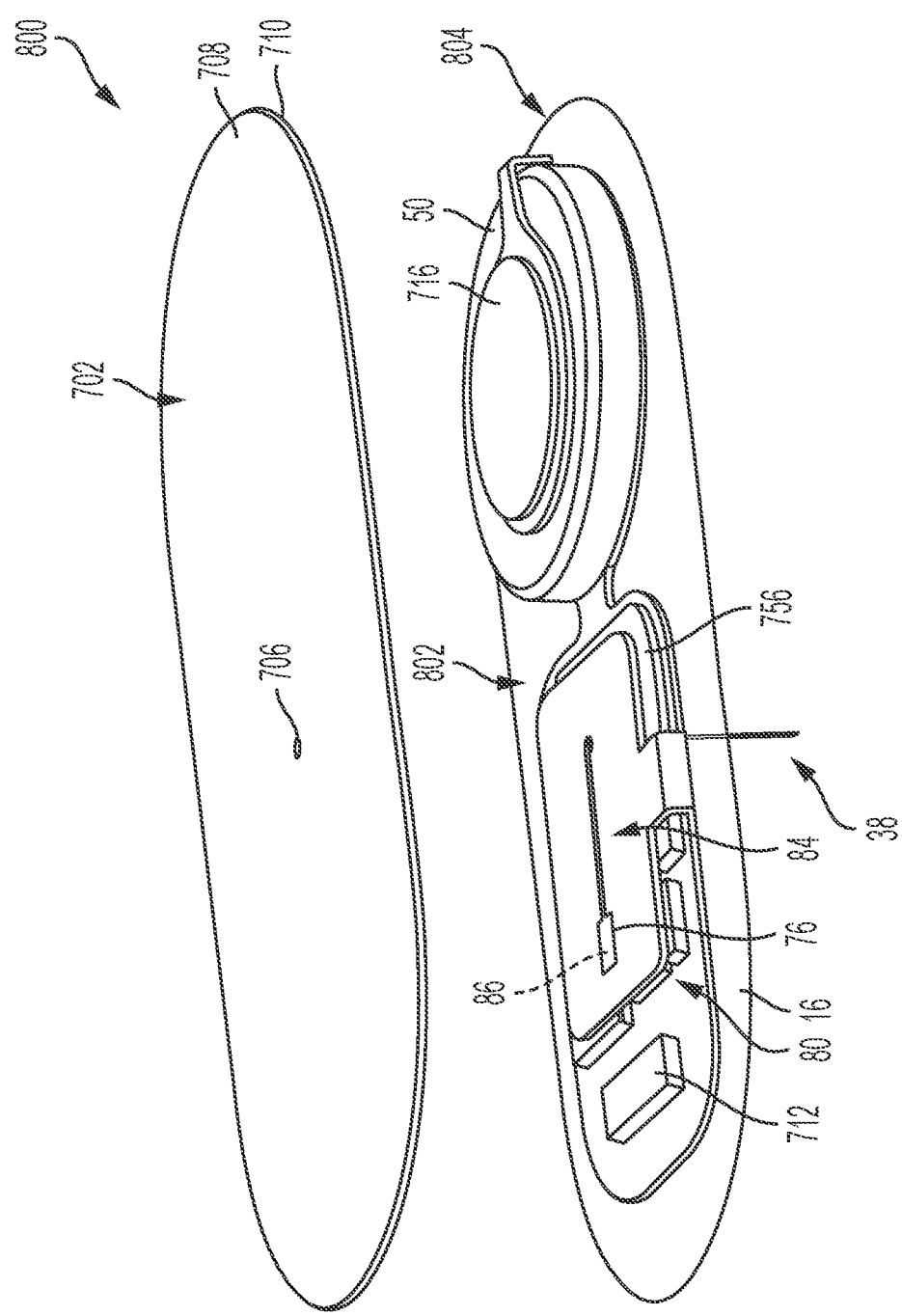
FIG. 40 is a partially exploded perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 40, a physiological characteristic sensor assembly 800 is provided in accordance with various embodiments. The physiological characteristic sensor assembly 800 is flexible, and has a low profile. As the physiological characteristic sensor assembly 800 includes components that are similar or the same as the physiological characteristic sensor assembly 10 discussed with regard to FIGS. 1-9, the physiological characteristic sensor assembly 700 discussed with regard to FIGS. 34-36 and the physiological characteristic sensor assembly 750 discussed with regard to FIGS. 37-39, the same reference numerals will be used to denote the same components. In one example, the physiological characteristic sensor assembly 800 includes the top housing 702, an electrical subsystem 802, the lower housing 16 and the coupling member or adhesive patch 18 (not shown). The lower housing 16, in this embodiment, may comprise a thin film layer, composed of a polymer-based material, including, but not limited to, polyurethane or polyethylene terephthalate.

The top housing 702 is opposite the lower housing 16 and the adhesive patch 18. The top housing 702 includes the needle bore 706 that extends through the top housing 702 from the first side 708 to the second side 710. The electrical subsystem 802 is contained between the top housing 702 and the lower housing 16. In one example, with reference to FIG. 41, the electrical subsystem 802 includes the battery 50, the antenna 712, a flexible printed circuit board 804, the sensor 38, the conductive film 716, the shim 718 and the rigidizer 756. The battery 50 provides power to the various components of the electrical subsystem 802. The battery 50 is electrically and physically coupled to the flexible printed circuit board 804. The antenna 712 enables wireless communication between the physiological characteristic sensor assembly 800 and another device, including, but not limited to, an infusion pump, handheld device (tablet, smart phone, etc.) or other monitoring device.

The flexible printed circuit board 804 electrically couples the battery 50 and the antenna 712 to the electrical components 80 associated with the physiological characteristic sensor assembly 800 to enable communication between the battery 50, the antenna 712 and the electrical components 80. In one example, the flexible printed circuit board 804 is composed of a bio-compatible polymer, including, but not limited to polyimide. A top surface 806 of the flexible printed circuit board 804 includes the pair of battery contact pads 66, 67 and the one or more contact pads. The battery contact pad 66 is separated by the battery contact pad 67 by a thin portion 804a of the flexible printed circuit board 804, which enables the battery contact pad 66 to be folded over on top of the battery 50. The flexible printed circuit board 804 also includes a bottom surface 760 opposite the top surface 758. The bottom surface 760 is coupled to the lower housing 16. The flexible printed circuit board 804 includes the sensor bore 79 defined through the top surface 806 and the bottom surface 808. The sensor bore 79 enables the needle 256 of the sensor introducer 110 (FIG. 12) to pass through the flexible printed circuit board 804 and into the sensor 38. In this example, the flexible printed circuit board 804 includes a wing 810. The wing 810 is coupled to the flexible printed circuit board 804 by a portion 804b of the flexible printed circuit board 804. The wing 810 includes the sensor contact pad 76, which is disposed on a surface 810a of the wing 810, which is opposite a surface 810b of the wing 810 (FIG. 40). The sensor contact pad 76 electrically couples the sensor 38 to the flexible printed circuit board 804. The wing 810 defines a needle bore 810c that extends through the wing 810 to enable the needle 256 of the sensor introducer 110 (FIG. 12) to pass through the wing 810 and into the sensor 38.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the wing 810 of the flexible printed circuit board 804. The conductive film 716 electrically couples the top housing 702 to the flexible printed circuit board 804 to enable a user to start-up or initiate the physiological characteristic sensor assembly 800 to monitor the BG levels of the user. The shim 718 is coupled between the conductive film 716 and the flexible printed circuit board 804 to electrically separate the conductive film 716 from the flexible printed circuit board 804. The rigidizer 756 is coupled to the flexible printed circuit board 804 so as to be positioned over a portion of the sensor 38 and between the battery 50 and the electrical components 80. In this embodiment, the rigidizer 756 provides a larger rigid area, so that in the case on an external load that is applied to the physiological characteristic sensor assembly 800 while the user is wearing the physiological characteristic sensor assembly 800, the load will be distributed across the area occupied by the rigidizer 756 rather than focused directly on the sensor 38. In addition, the rigidizer 756 provides a uniformly level (i.e. horizontal level) for the sensor 38 to be mounted on the flexible printed circuit board 804 which is folded over the electrical components 80.

In one example, in order to assemble the physiological characteristic sensor assembly 800, the electrical components 80 are electrically and physically coupled to the flexible printed circuit board 804 by a low temperature reflow soldering. The antenna 712 is electrically and physically coupled to the flexible printed circuit board 804 by a low temperature reflow soldering. The battery 50 is coupled to the battery contact pad 67, and with reference to FIG. 42, the battery contact pad 66 of the flexible printed circuit board 804 is folded over the battery 50. The rigidizer 756 is coupled to the flexible printed circuit board 804 so as to be disposed over a portion of the proximal end 84 of the sensor 38. The wing 810 is folded over the rigidizer 756 such that the surface 810a is adjacent to the rigidizer 756 and the electrical components 80. With reference to FIG. 34, the shim 718 is coupled to the flexible printed circuit board 804, via adhesives, for example, so as to be disposed over the battery 50. The conductive film 716 is coupled to the shim 718. The sensor 38 is coupled to the flexible printed circuit board 804 such that the sensor contacts 86 are electrically and physically coupled to the sensor contact pad 76 disposed on the wing 810 of the flexible printed circuit board 804. With the sensor bore 79 coaxially aligned with the sensor bore 98, the lower housing 16 is coupled to the flexible printed circuit board 804. The top housing 702 is positioned over the electrical subsystem 802 such that the needle bore 706 is coaxially aligned with the needle bore 810c. The top housing 702 is coupled to the lower housing 16, via thermal welding, for example. The adhesive patch 18 may be coupled to the lower housing 16 for affixing the lower housing 16, and thus, the physiological characteristic sensor assembly 800, to the skin of the user. The physiological characteristic sensor assembly 800 may then be deployed onto a body of the user, and the user may depress the conductive film 716 to initiate the monitoring of the BG levels with the sensor 38. Upon initiation or activation, the controller receives the sensor signals from the sensor 38 and transmits or communicates these sensor signals, via the antenna 712, to the remote device, including, but not limited to, an infusion pump, handheld device (tablet, smart phone, etc.) or other monitoring device.

Figure 43:
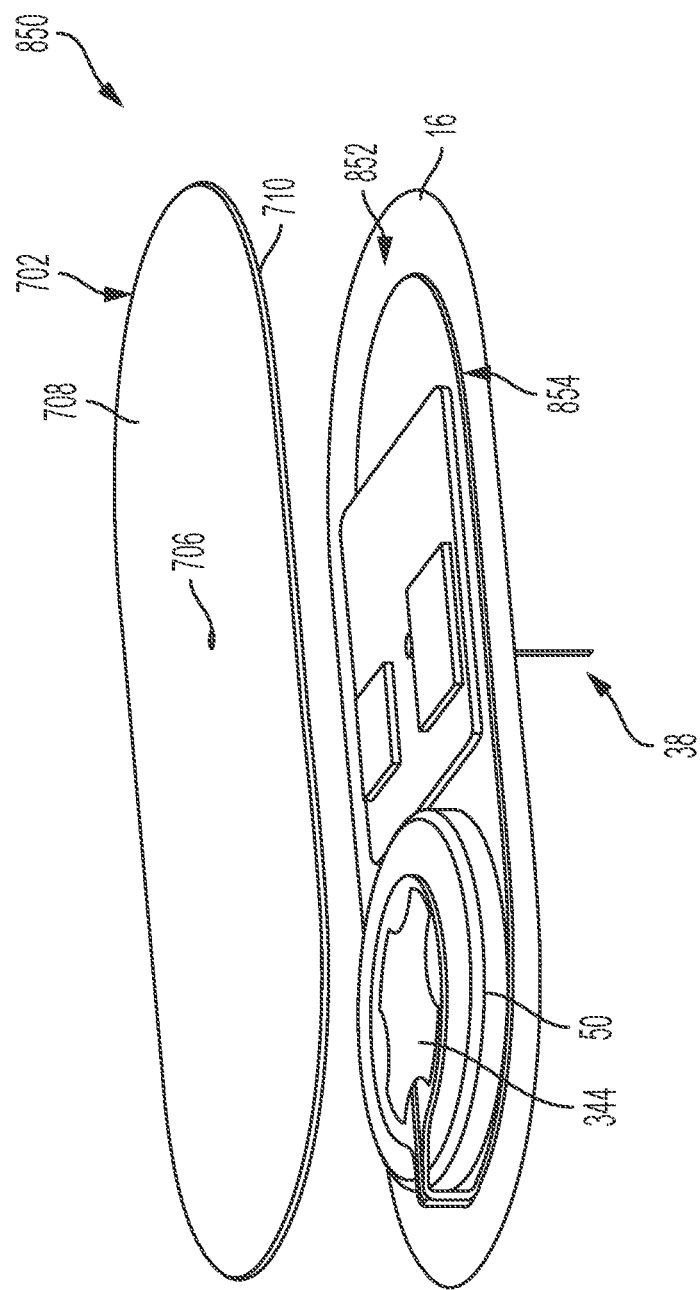
FIG. 43 is a partially exploded perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 43, a physiological characteristic sensor assembly 850 is provided in accordance with various embodiments. The physiological characteristic sensor assembly 850 is flexible, and has a low profile. As the physiological characteristic sensor assembly 850 includes components that are similar or the same as the physiological characteristic sensor assembly 10 discussed with regard to FIGS. 1-9, the physiological characteristic sensor assembly 300 discussed with regard to FIGS. 20-25, and the physiological characteristic sensor assembly 700 discussed with regard to FIGS. 34-36, the same reference numerals will be used to denote the same components. In one example, the physiological characteristic sensor assembly 850 includes the top housing 702, an electrical subsystem 852, the lower housing 16 and the coupling member or adhesive patch 18 (not shown). The lower housing 16, in this embodiment, may comprise a thin film layer, composed of a polymer-based material, including, but not limited to, polyurethane or polyethylene terephthalate.

Figure 44:
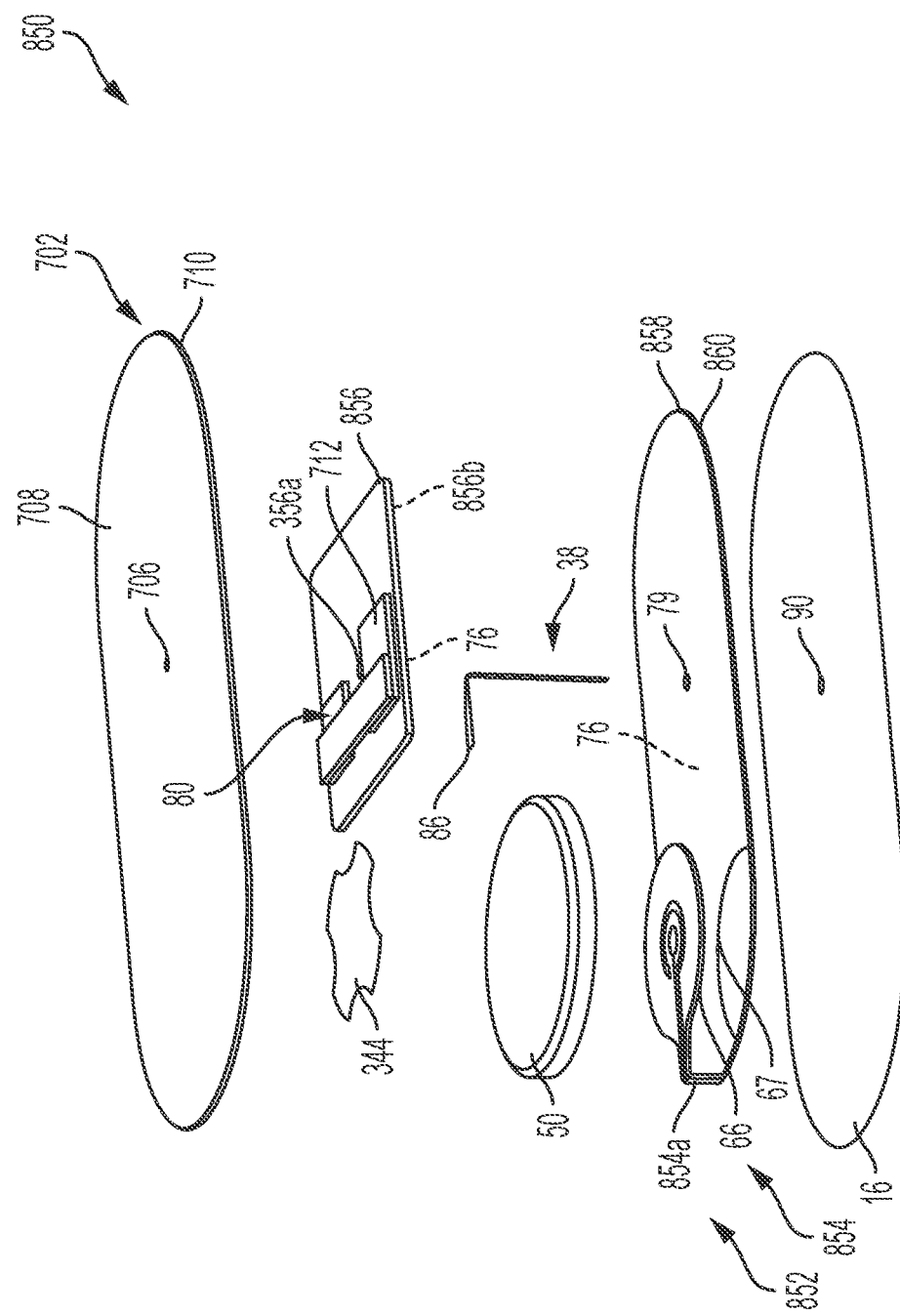
FIG. 44 is an exploded view of the physiological characteristic sensor assembly of FIG. 43.

The top housing 702 is opposite the lower housing 16 and the adhesive patch 18. The top housing 702 includes the needle bore 706 that extends through the top housing 702 from the first side 708 to the second side 710. The electrical subsystem 852 is contained between the top housing 702 and the lower housing 16. In one example, with reference to FIG. 44, the electrical subsystem 852 includes the battery 50, the antenna 712, a flexible printed circuit board 854, a rigid printed circuit board 856, the sensor 38, and the push button 344. The battery 50 provides power to the various components of the electrical subsystem 852. The battery 50 is electrically and physically coupled to the flexible printed circuit board 854. The antenna 712 enables wireless communication between the physiological characteristic sensor assembly 850 and another device, including, but not limited to, an infusion pump, handheld device (tablet, smart phone, etc.) or other monitoring device.

The flexible printed circuit board 854 electrically couples the battery 50 and the antenna 712 to the electrical components 80 associated with the physiological characteristic sensor assembly 850 to enable communication between the battery 50, the antenna 712 and the electrical components 80. In one example, the flexible printed circuit board 854 is composed of a bio-compatible polymer, including, but not limited to polyimide. A top surface 858 of the flexible printed circuit board 854 includes the pair of battery contact pads 66, 67 and the one or more contact pads. The battery contact pad 66 is separated by the battery contact pad 67 by a thin portion 854a of the flexible printed circuit board 854, which enables the battery contact pad 66 to be folded over on top of the battery 50. The flexible printed circuit board 854 also includes a bottom surface 860 opposite the top surface 858. The bottom surface 860 is coupled to the lower housing 16. The flexible printed circuit board 854 includes the sensor bore 79 defined through the top surface 858 and the bottom surface 860. The sensor bore 79 enables the needle 256 of the sensor introducer 110 (FIG. 12) to pass through the flexible printed circuit board 854 and into the sensor 38. In one example, the flexible printed circuit board 854 includes the sensor contact pad 76, which is disposed on the top surface 858. The sensor contact pad 76 electrically couples the sensor 38 to the flexible printed circuit board 854. In another example, the rigid printed circuit board 856 includes the sensor contact pad 76, which is disposed on a bottom surface 856b of the rigid printed circuit board 856. In this example, the sensor contact pad 76 electrically couples the sensor 38 to the rigid printed circuit board 856.

The rigid printed circuit board 856 is electrically and physically coupled to the flexible printed circuit board 854. The rigid printed circuit board 856 is electrically and physically coupled to the electrical components 80 associated with the physiological characteristic sensor assembly 850. The rigid printed circuit board 856 also includes a sensor bore 856a, which is concentric with the sensor bore 79.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 of the flexible printed circuit board 854. The push button 344 enables a user to activate the physiological characteristic sensor assembly 850.

In one example, in order to assemble the physiological characteristic sensor assembly 850, the electrical components 80 and the antenna 712 are electrically and physically coupled to the rigid printed circuit board 856 by a low temperature reflow soldering. The rigid printed circuit board 856 is electrically and physically coupled to the flexible printed circuit board 854. The battery 50 is coupled to the battery contact pad 67, and with reference to FIG. 43, the battery contact pad 66 of the flexible printed circuit board 854 is folded over the battery 50. The push button 344 is coupled to the flexible printed circuit board 854 so as to be disposed over the battery 50. The sensor 38 is coupled to the flexible printed circuit board 854 or the rigid printed circuit board 856 such that the sensor contacts 86 are electrically and physically coupled to the sensor contact pad 76. With the sensor bore 79 coaxially aligned with the sensor bore 98, the lower housing 16 is coupled to the flexible printed circuit board 854. The top housing 702 is positioned over the electrical subsystem 802 such that the needle bore 706 is coaxially aligned with the bore 356a. The top housing 702 is coupled to the lower housing 16, via thermal welding, for example. The adhesive patch 18 may be coupled to the lower housing 16 for affixing the lower housing 16, and thus, the physiological characteristic sensor assembly 850, to the skin of the user. The physiological characteristic sensor assembly 850 may then be deployed onto a body of the user, and the user may depress the push button 344 to initiate the monitoring of the BG levels with the sensor 38. Upon initiation or activation, the controller receives the sensor signals from the sensor 38 and transmits or communicates these sensor signals, via the antenna 712, to the remote device, including, but not limited to, an infusion pump, handheld device (tablet, smart phone, etc.) or other monitoring device.

Figure 44A:
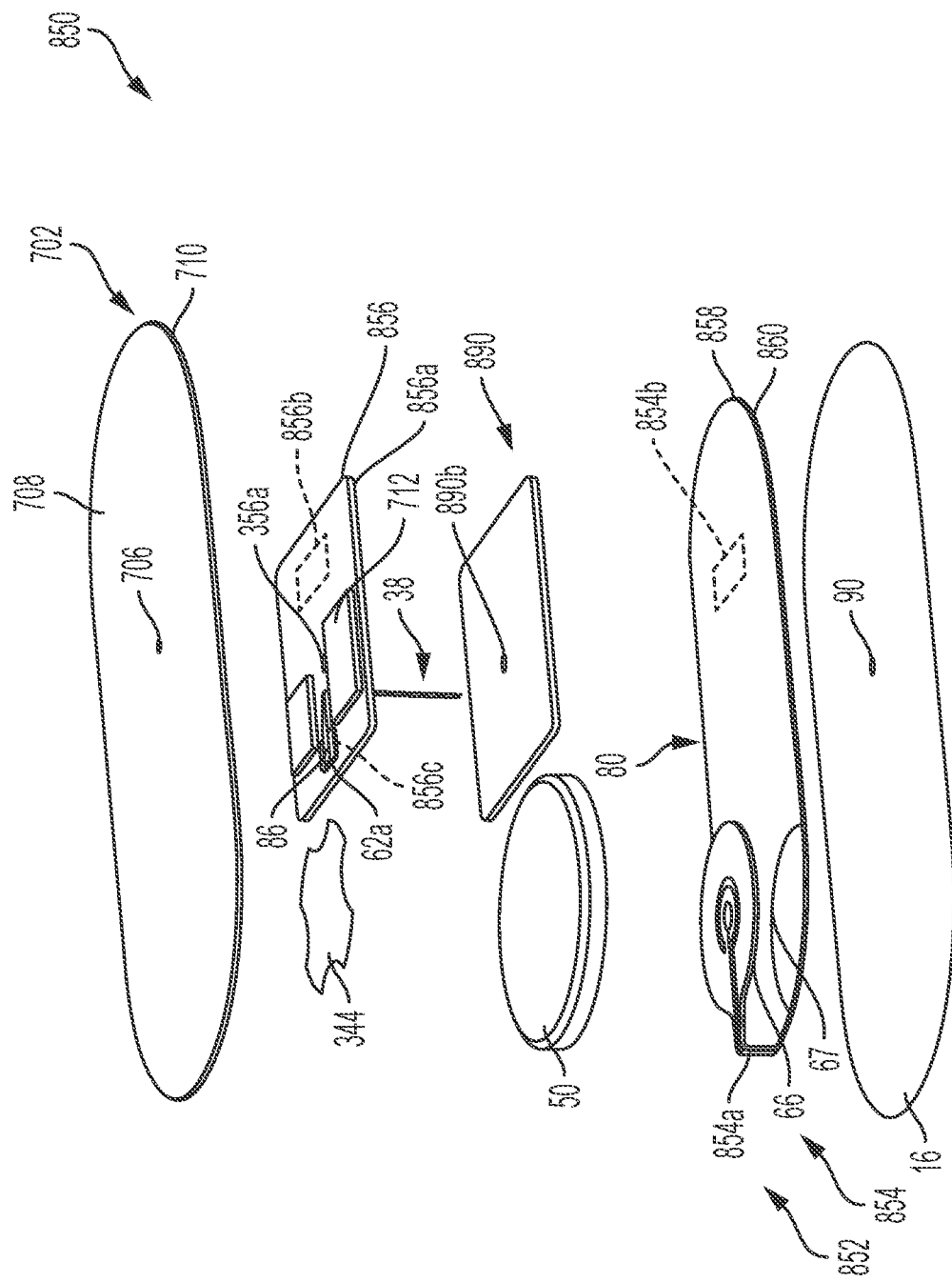
FIG. 44A is a partially exploded view of an alternative arrangement for coupling a rigid circuit board to a flexible circuit board, which in this example is shown with the physiological characteristic sensor assembly of FIG. 43.

In addition, it should be noted that in other embodiments, the rigid printed circuit board 856 may be electrically and physically coupled differently to the flexible printed circuit board 854 of the physiological characteristic sensor assembly 850. With reference to FIG. 44A, a partially exploded view provides another exemplary mounting for the rigid printed circuit board 856 to the flexible printed circuit board 854 for the physiological characteristic sensor assembly 850. In this example, a conductive adhesive layer 890 electrically and physically couples the rigid printed circuit board 856 to the flexible printed circuit board 854. In one example, the conductive adhesive layer 890 is a layer of anisotropically electrically conductive pressure sensitive adhesive. Generally, the conductive adhesive layer 890 is placed on the top surface 858 of the flexible printed circuit board 854; and then, the rigid printed circuit board 856 is placed on top of the conductive adhesive layer 890. In this example, the top surface 858 of the flexible printed circuit board 854 includes exposed contacts 854b, and a bottom surface 856a of the rigid printed circuit board 856 includes exposed contact pads 856b, which are positioned directly above the exposed contact pads 854b of the flexible printed circuit board 854. The corresponding contact pad pairs 856b, 854b of the rigid printed circuit board 856 and the flexible printed circuit board 854, respectively, are then electrically connected via the conductive adhesive layer 890. The conductive adhesive layer 890 also defines a bore 890b, which enables a portion of the sensor 38 to pass through the conductive adhesive layer 890. In addition, in this example, the sensor 38 is electrically and physically coupled to the rigid printed circuit board 856 via the conductive adhesive patch 62a. Thus, in this example, the rigid printed circuit board 856 also includes electrical contact pads 856c for electrically coupling with the sensor contact pads 86 of the sensor 38 via the conductive adhesive patch 62a. It should be noted that the conductive adhesive layer 890 may be used to with any physiological characteristic sensor assembly described herein to couple a rigid printed circuit board to a flexible printed circuit board, and thus, the use of the physiological characteristic sensor assembly 850 is merely an example.

Figure 45:
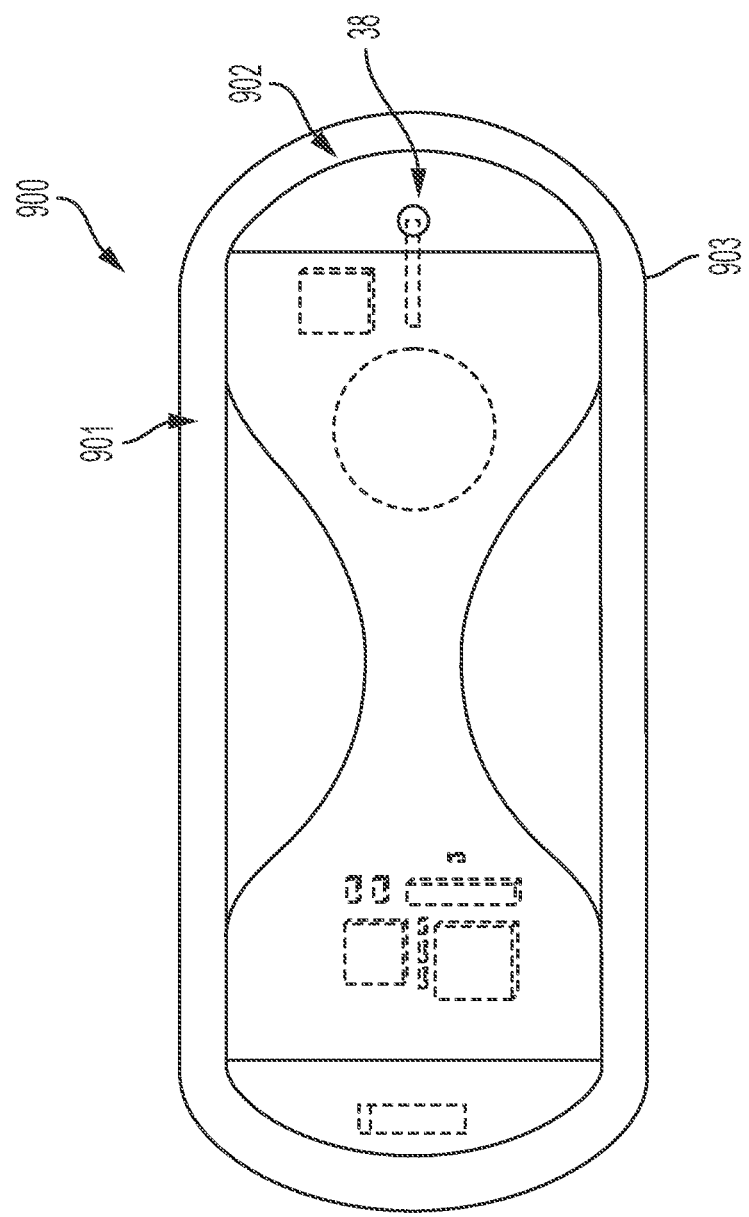
FIG. 45 is a top view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 45, a physiological characteristic sensor assembly 900 is provided in accordance with various embodiments. The physiological characteristic sensor assembly 900 is flexible, and has a low profile. As the physiological characteristic sensor assembly 900 includes components that are similar or the same as the physiological characteristic sensor assembly 10 discussed with regard to FIGS. 1-9, the physiological characteristic sensor assembly 300 discussed with regard to FIGS. 20-25, and the physiological characteristic sensor assembly 700 discussed with regard to FIGS. 34-36, the same reference numerals will be used to denote the same components. In one example, the physiological characteristic sensor assembly 900 includes a first or top housing 901, an electrical subsystem 902, a second or lower housing 903 and the coupling member or adhesive patch 18 (not shown).

Figure 46:
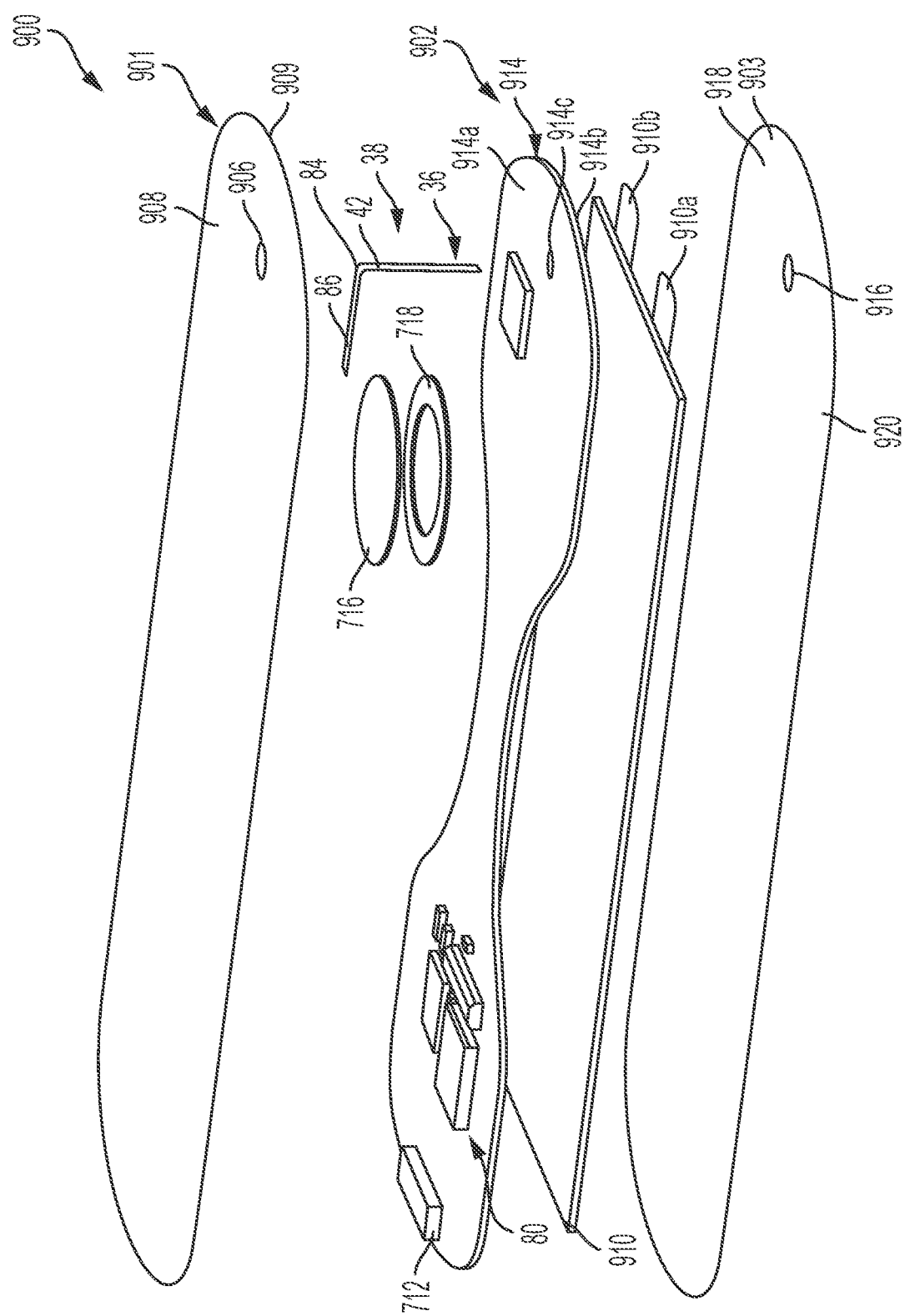
FIG. 46 is a partially exploded perspective view of the physiological characteristic sensor assembly of FIG. 45 in accordance with various embodiments.

With reference to FIG. 46, the top housing 901 is opposite the lower housing 16 and the adhesive patch 18. The top housing 901 forms a portion of an outermost surface of the physiological characteristic sensor assembly 900. The top housing 901 is flexible, and in one example is composed of a thin film of a biocompatible polymer, including, but not limited to, a polyurethane or polyethylene terephthalate. The top housing 901 may be molded, three-dimensionally printed, etc. The top housing 901 includes a needle bore 906 that extends through the top housing 901 from a first side 908 to a second side 909. The needle bore 906 cooperates with a sensor introducer, such as the sensor introducer 110 discussed with regard to FIGS. 10-19, to couple the physiological characteristic sensor assembly 900 to the body of the user.

The electrical subsystem 902 is contained between the top housing 901 and the lower housing 903. In one example, the electrical subsystem 902 includes a power source or battery 912, the antenna 712, a flexible printed circuit board 914, the sensor 38, the conductive film 716 and the shim 718. The battery 910 provides power to the various components of the electrical subsystem 902. The battery 910 is electrically and physically coupled to the flexible printed circuit board 914. In one example, the battery 910 is a flexible thin film battery. It should be noted that in other embodiments the battery 910 may be a coin-cell battery. In one example, the battery 910 is a 25 milliamp Hour (mAh) battery, that is about 0.35 mm to about 0.55 mm thick. The antenna 712 enables wireless communication between the physiological characteristic sensor assembly 900 and another device, including, but not limited to, an infusion pump, handheld device (tablet, smart phone, etc.) or other monitoring device.

The flexible printed circuit board 914 electrically couples the battery 910 and the antenna 712 to the electrical components 80 associated with the physiological characteristic sensor assembly 900 to enable communication between the battery 910, the antenna 712 and the electrical components 80. As discussed previously, in various embodiments, the electrical components 80 are conventional, and include at least a processor, a Bluetooth low energy module, and memory. In one example, the flexible printed circuit board 914 is composed of a bio-compatible polymer, including, but not limited to polyimide. The flexible printed circuit board 914 includes a top surface 914a opposite a bottom surface 914b. The electrical components 80 and the antenna 712 are coupled to the top surface 914a. In one example, the flexible printed circuit board 914 includes the sensor contact pad 76, which is disposed on the top surface 914a. The sensor contact pad 76 electrically couples the sensor 38 to the flexible printed circuit board 914. A bottom surface 914b of the flexible printed circuit board 914 includes a pair of battery contact pads for electrically coupling contact pads 910a, 910b of the battery 910 to the flexible printed circuit board 914. In one example, a conductive adhesive patch, such as the conductive adhesive patches 62b, 62c (not shown) may be employed to couple the battery 910 to the flexible printed circuit board 914. The bottom surface 914b is coupled to the lower housing 903. The flexible printed circuit board 914 includes a bore 914c defined through the top surface 914a and the bottom surface 914b. The bore 914c enables the needle 256 of the sensor introducer 110 (FIG. 12) to pass through the flexible printed circuit board 914 and into the sensor 38.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the flexible printed circuit board 914. The conductive film 716 electrically couples the top housing 901 to the flexible printed circuit board 914 to enable a user to start-up or initiate the physiological characteristic sensor assembly 900 to monitor the BG levels of the user. The shim 718 is coupled between the conductive film 716 and the flexible printed circuit board 914 to electrically separate the conductive film 716 from the flexible printed circuit board 914.

The lower housing 903 is substantially planar, and is flexible. The lower housing 903, in this embodiment, may comprise a thin film layer, composed of a polymer-based material, including, but not limited to, polyurethane or polyethylene terephthalate. The lower housing 903 may be molded, three-dimensionally printed, cast, etc. The lower housing 903 cooperates with the top housing 901 to encase, surround or enclose the electrical subsystem 902. In one example, the lower housing 903 is coupled to the top housing 901 by thermal welding, however, the lower housing 903 may be coupled to the top housing 12 through any suitable technique, including, but not limited to RF welding, ultrasonic welding, epoxy, double sided adhesives, etc. The lower housing 16 includes a bore 916 defined through the lower housing 903 from a first housing side 918 to a second housing side 920. The second housing side 920 is coupled to the adhesive patch 18.

In one example, in order to assemble the physiological characteristic sensor assembly 900, the electrical components 80 and the antenna 712 are electrically and physically coupled to the flexible printed circuit board 914. The battery 910 is coupled to the battery contact pads on the bottom surface 914b of the flexible printed circuit board 914. The sensor 38 is coupled to the flexible printed circuit board 914 such that the sensor contacts 86 are electrically and physically coupled to the sensor contact pad 76. With the bore 914c coaxially aligned with the bore 916, the lower housing 903 is coupled to the flexible printed circuit board 914 such that the battery 910 is positioned between the flexible printed circuit board 914 and the lower housing 903. The shim 718 is coupled to the flexible printed circuit board 914, via adhesives, for example. The conductive film 716 is coupled to the shim 718. The top housing 901 is positioned over the electrical subsystem 902 such that the needle bore 906 is coaxially aligned with the bore 914c. The top housing 901 is coupled to the lower housing 903, via thermal welding, for example. The adhesive patch 18 may be coupled to the lower housing 903 for affixing the lower housing 903, and thus, the physiological characteristic sensor assembly 900, to the skin of the user. The physiological characteristic sensor assembly 900 may then be deployed onto a body of the user, and the user may depress the conductive film 716 to initiate the monitoring of the BG levels with the sensor 38. Upon initiation or activation, the controller receives the sensor signals from the sensor 38 and transmits or communicates these sensor signals, via the antenna 712, to the remote device, including, but not limited to, an infusion pump, handheld device (tablet, smart phone, etc.) or other monitoring device.

Figure 47:
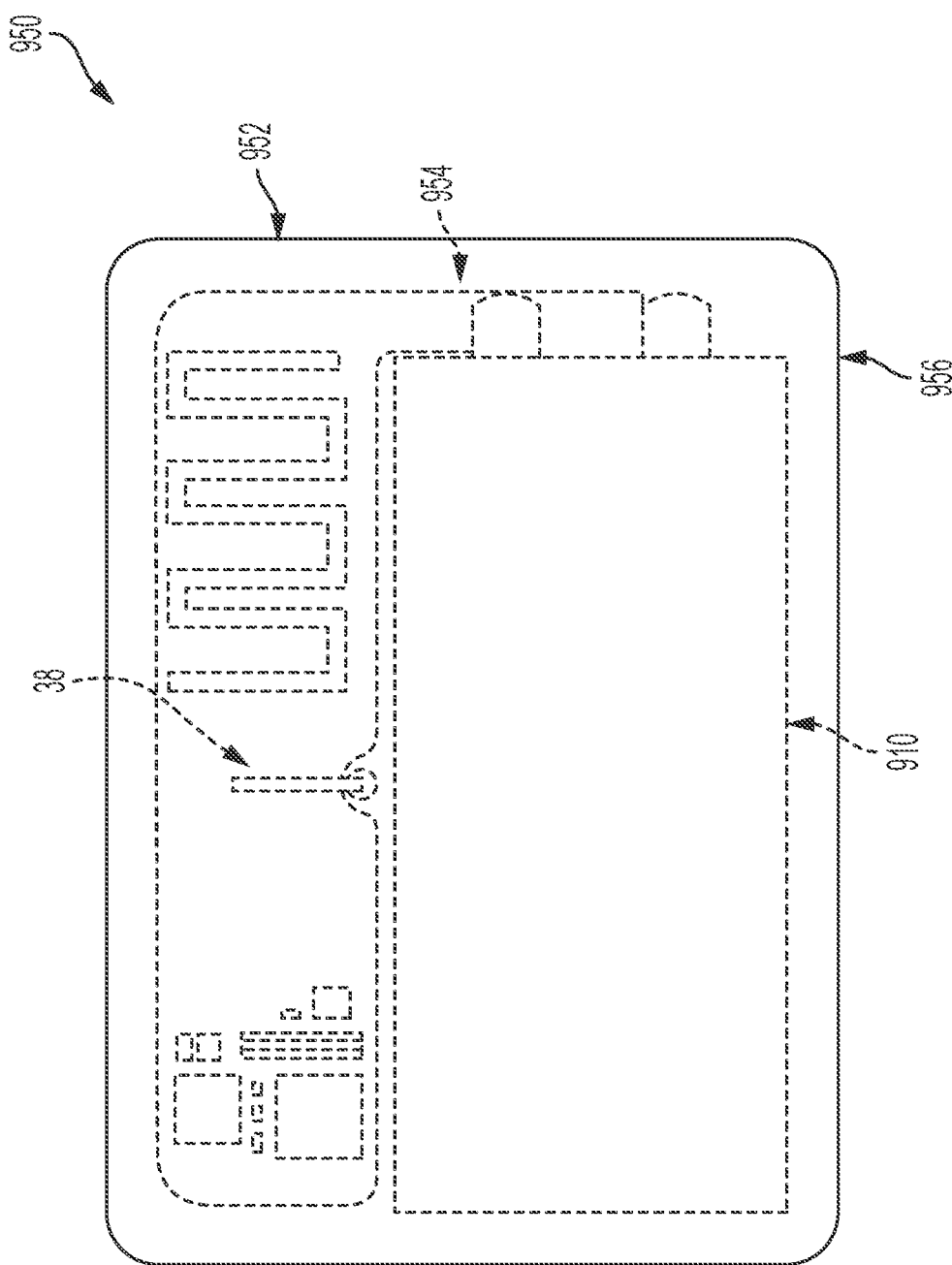
FIG. 47 is a top view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 47, a physiological characteristic sensor assembly 950 is provided in accordance with various embodiments. The physiological characteristic sensor assembly 900 is flexible, and has a low profile. As the physiological characteristic sensor assembly 900 includes components that are similar or the same as the physiological characteristic sensor assembly 10 discussed with regard to FIGS. 1-9, the physiological characteristic sensor assembly 300 discussed with regard to FIGS. 20-25, the physiological characteristic sensor assembly 700 discussed with regard to FIGS. 34-36, the physiological characteristic sensor assembly 900 discussed with regard to FIGS. 45 and 46 the same reference numerals will be used to denote the same components. In one example, the physiological characteristic sensor assembly 950 includes a first or top housing 952, an electrical subsystem 954 and a coupling member or adhesive patch 956.

Figure 48:
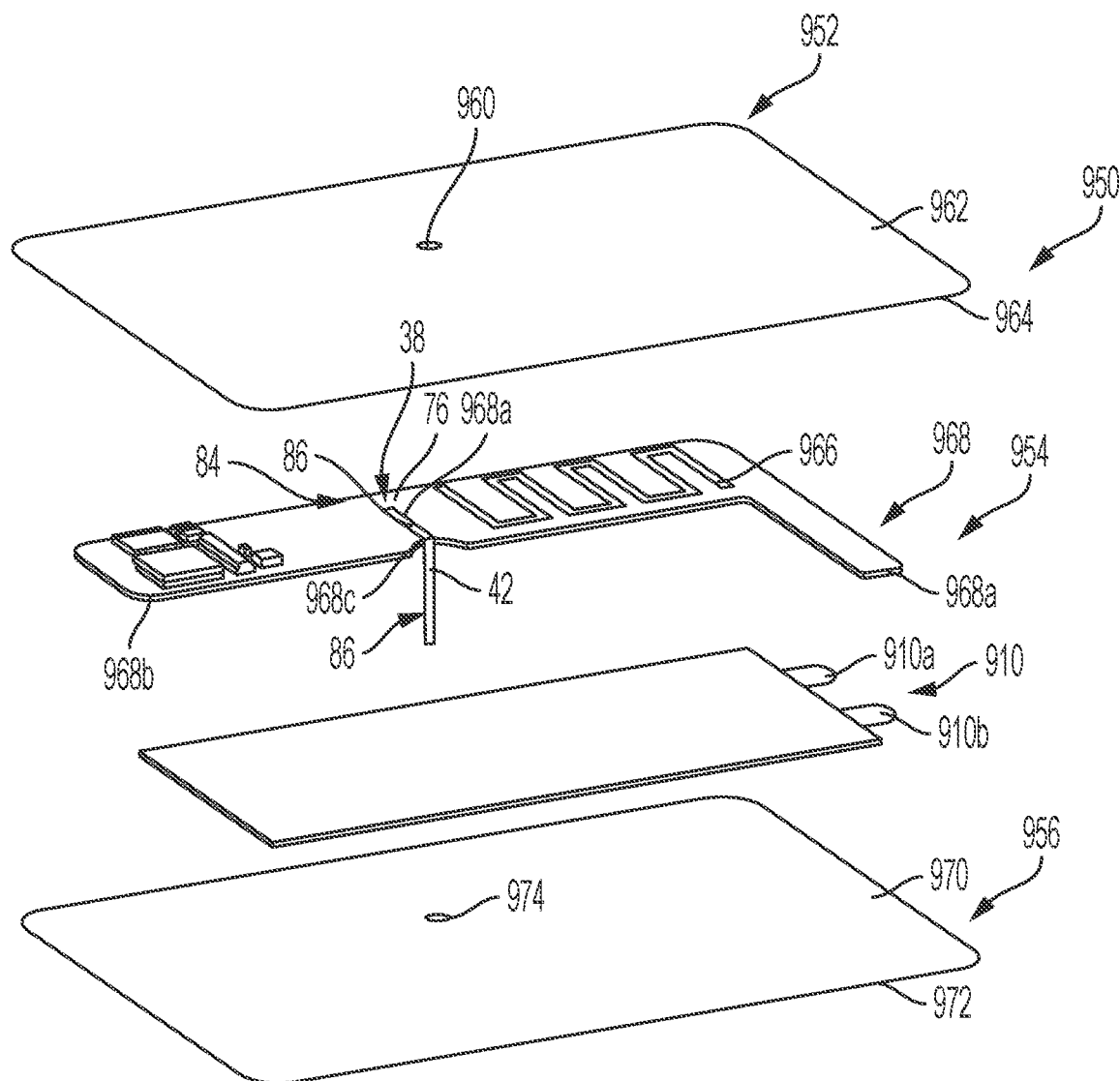
FIG. 48 is a partially exploded perspective view of the physiological characteristic sensor assembly of FIG. 47 in accordance with various embodiments.

With reference to FIG. 48, the top housing 952 is opposite the adhesive patch 956. The top housing 952 forms an outermost surface of the physiological characteristic sensor assembly 950. The top housing 952 is flexible, and in one example is composed of a thin film of a biocompatible polymer, including, but not limited to, a polyurethane or polyethylene terephthalate. In this example, the top housing 952 is about 0.01 mm to about 0.10 mm thick. The top housing 952 may be molded, three-dimensionally printed, etc. The top housing 952 includes a needle bore 960 that extends through the top housing 952 from a first side 962 to a second side 964. The needle bore 906 cooperates with a sensor introducer, such as the sensor introducer 110 discussed with regard to FIGS. 10-19, to couple the physiological characteristic sensor assembly 950 to the body of the user. In this example, the top housing 952 cooperates with the adhesive patch 956 to provide a waterproof seal and electrical insulation for the electrical subsystem 954.

The electrical subsystem 954 is contained between the top housing 952 and the adhesive patch 956. In one example, the electrical subsystem 954 includes the battery 910, an antenna 966, a flexible printed circuit board 968 and the sensor 38. The battery 910 provides power to the various components of the electrical subsystem 902. The battery 910 is electrically and physically coupled to the flexible printed circuit board 968. In one example, the battery 910 is a flexible thin film battery. It should be noted that in other embodiments the battery 910 may be a coin-cell battery. The antenna 966 enables wireless communication between the physiological characteristic sensor assembly 950 and another device, including, but not limited to, an infusion pump, handheld device (tablet, smart phone, etc.) or other monitoring device. In one example, the antenna 966 is a Bluetooth low energy (BLE) trace antenna formed on or coupled to the flexible printed circuit board 968. In other embodiments, the antenna 966 may comprise a chip antenna, wire antenna or a stamped metal antenna. The antenna 966 is in electrically coupled to the flexible printed circuit board 968. The antenna 966 may also include a near field communication (NFC) antenna and/or RF radio antenna.

The flexible printed circuit board 968 electrically couples the battery 910 and the antenna 966 to the electrical components 80 associated with the physiological characteristic sensor assembly 950 to enable communication between the battery 910, the antenna 966 and the electrical components 80. In one example, the flexible printed circuit board 968 is substantially L-shaped, and is composed of a bio-compatible polymer, including, but not limited to polyethylene terephthalate. In this example, the flexible printed circuit board 968 is about 0.35 mm to about 0.45 mm thick. The flexible printed circuit board 968 includes atop surface 968a opposite a bottom surface 968b. The electrical components 80 and the antenna 966 are coupled to the top surface 968a. In one example, the flexible printed circuit board 968 includes the sensor contact pad 76, which is disposed on the top surface 968a. The sensor contact pad 76 electrically couples the sensor 38 to the flexible printed circuit board 968. A bottom surface 968b of the flexible printed circuit board 968 includes a pair of battery contact pads for electrically coupling contact pads 910a, 910b of the battery 910 to the flexible printed circuit board 968. The conductive adhesive patches 62b, 62c (not shown) may be employed to couple the battery 910 to the flexible printed circuit board 968. The bottom surface 968b is coupled to the adhesive patch 956. The flexible printed circuit board 968 includes a sensor cut-out 968c defined through the top surface 968a and the bottom surface 968b. The sensor cut-out 968c is substantially semi-circular, and enables the sensor 38 to pass through the flexible printed circuit board 968.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the flexible printed circuit board 968.

The adhesive patch 956 is coupled to the flexible printed circuit board 968 and affixes the physiological characteristic sensor assembly 950, to the skin of the user. The adhesive patch 956 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied. The adhesive patch 956 is substantially rectangular in shape, and has a first patch side 970 opposite a second patch side 972. The first patch side 970 includes an adhesive layer that couples the flexible printed circuit board 968 to the adhesive patch 956 to couple the top housing 952, the electrical subsystem 954 to the adhesive patch 956. The second patch side 972 includes a second adhesive layer that couples the adhesive patch 18 and the sensor 38 to the skin of the user. In certain instances, the second adhesive layer may be coupled with a second backing liner, which is removable by the user prior to the deployment of the sensor 38 at the sensor site. The adhesive patch 956 also defines a sensor bore 974 that extends through the adhesive patch 956 from the first patch side 970 to the second patch side 972. The sensor bore 974 enables the distal segment end 36 of the sensor 38 to pass through the adhesive patch 956 for subcutaneous placement into the body of the user.

Figure 49:
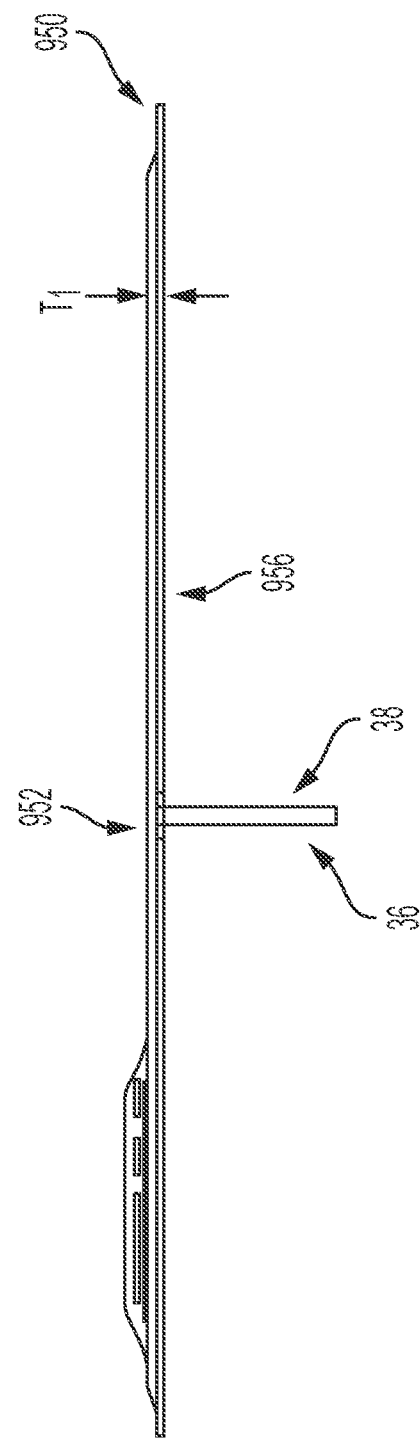
FIG. 49 is a side view of the physiological characteristic sensor assembly of FIG. 47 in accordance with various embodiments.

In one example, in order to assemble the physiological characteristic sensor assembly 950, the electrical components 80 and the antenna 966 are electrically and physically coupled to the flexible printed circuit board 968. The battery 910 is coupled to the battery contact pads on the bottom surface 968b of the flexible printed circuit board 968. The sensor 38 is coupled to the flexible printed circuit board 968 such that the sensor contacts 86 are electrically and physically coupled to the sensor contact pad 76. With the sensor bore 974 coaxially aligned with the distal segment end 36 of the sensor 38, the adhesive patch 956 is coupled to the flexible printed circuit board 968 such that the battery 910 is positioned on the adhesive patch 956 adjacent to and proximate the flexible printed circuit board 968. The top housing 952 is positioned over the electrical subsystem 954 such that the needle bore 960 is coaxially aligned with the sensor bore 974. The top housing 952 is coupled to the adhesive patch 956, via thermal welding, for example. Once assembled, with reference to FIG. 49, the physiological characteristic sensor assembly 950 has a thickness Ti, which is about 0.60 mm to about 0.70 mm. The physiological characteristic sensor assembly 950 may then be deployed onto a body of the user, and the user may activate the physiological characteristic sensor assembly 950 to initiate the monitoring of the BG levels with the sensor 38.

In one example, the physiological characteristic sensor assembly 950 may include the magnet sensor 85, such that the physiological characteristic sensor assembly 950 is activated once a magnetic field generated by a magnet coupled to a sensor introducer, such as the sensor introducer 110, is removed. In other embodiments, the physiological characteristic sensor assembly 950 may include the light sensor 82, such that the physiological characteristic sensor assembly 950 is activated once an ambient light is observed by the light sensor 82. In still other embodiments, the physiological characteristic sensor assembly 950 may include the push button 83, such that the physiological characteristic sensor assembly 950 is activated once the push button 83 is deployed or pressed by a user. In yet another embodiment, the physiological characteristic sensor assembly 950 may be activated based on a signal or transmission received from another device, such as a signal transmitted by a near-field communication system associated with a remote device. Upon activation, the controller receives the sensor signals from the sensor 38 and transmits or communicates these sensor signals, via the antenna 966, to the remote device, including, but not limited to, an infusion pump, handheld device (tablet, smart phone, etc.) or other monitoring device.

Figure 50:
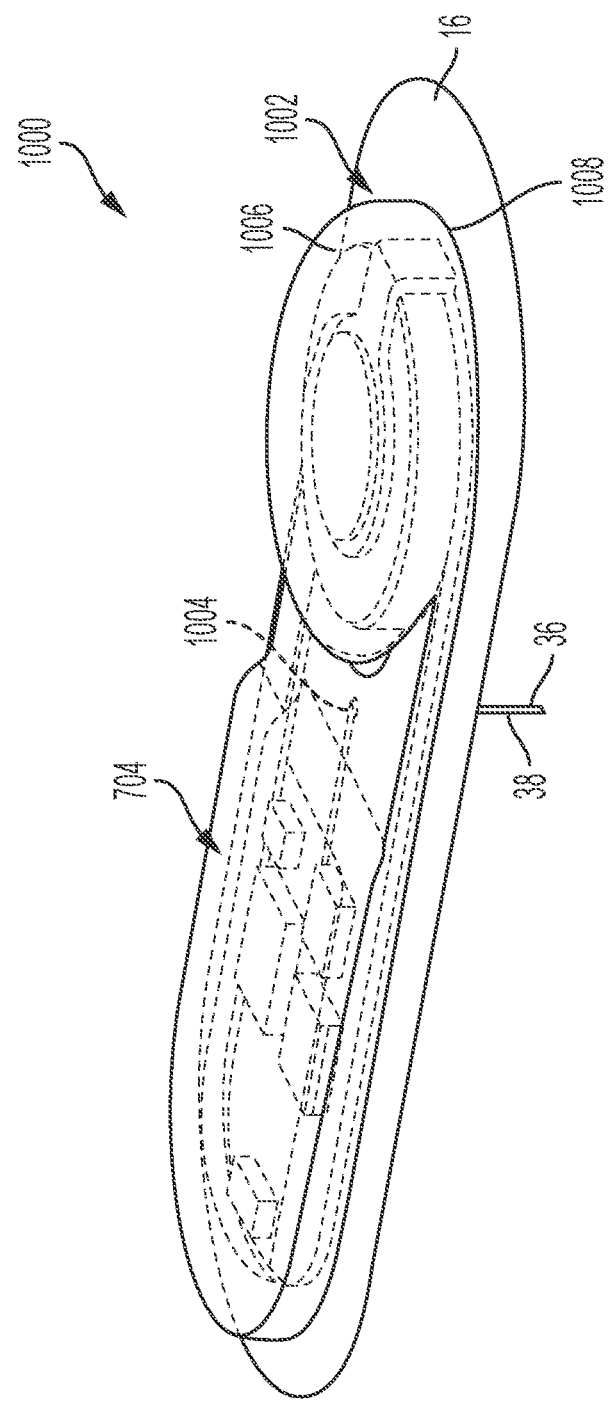
FIG. 50 is a perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 50, a physiological characteristic sensor assembly 1000 is provided in accordance with various embodiments. The physiological characteristic sensor assembly 1000 is flexible, and has a low profile. As the physiological characteristic sensor assembly 100 includes components that are similar or the same as the physiological characteristic sensor assembly 10 discussed with regard to FIGS. 1-9 and the physiological characteristic sensor assembly 700 discussed with regard to FIGS. 34-36, the same reference numerals will be used to denote the same components. In one example, the physiological characteristic sensor assembly 1000 includes a first or top housing 1002, the electrical subsystem 704 (FIG. 51), the lower housing 16 and the coupling member or adhesive patch 18 (not shown). The lower housing 16, in this embodiment, may comprise a thin film layer, composed of a polymer-based material, including, but not limited to, polyurethane or polyethylene terephthalate.

Figure 51:
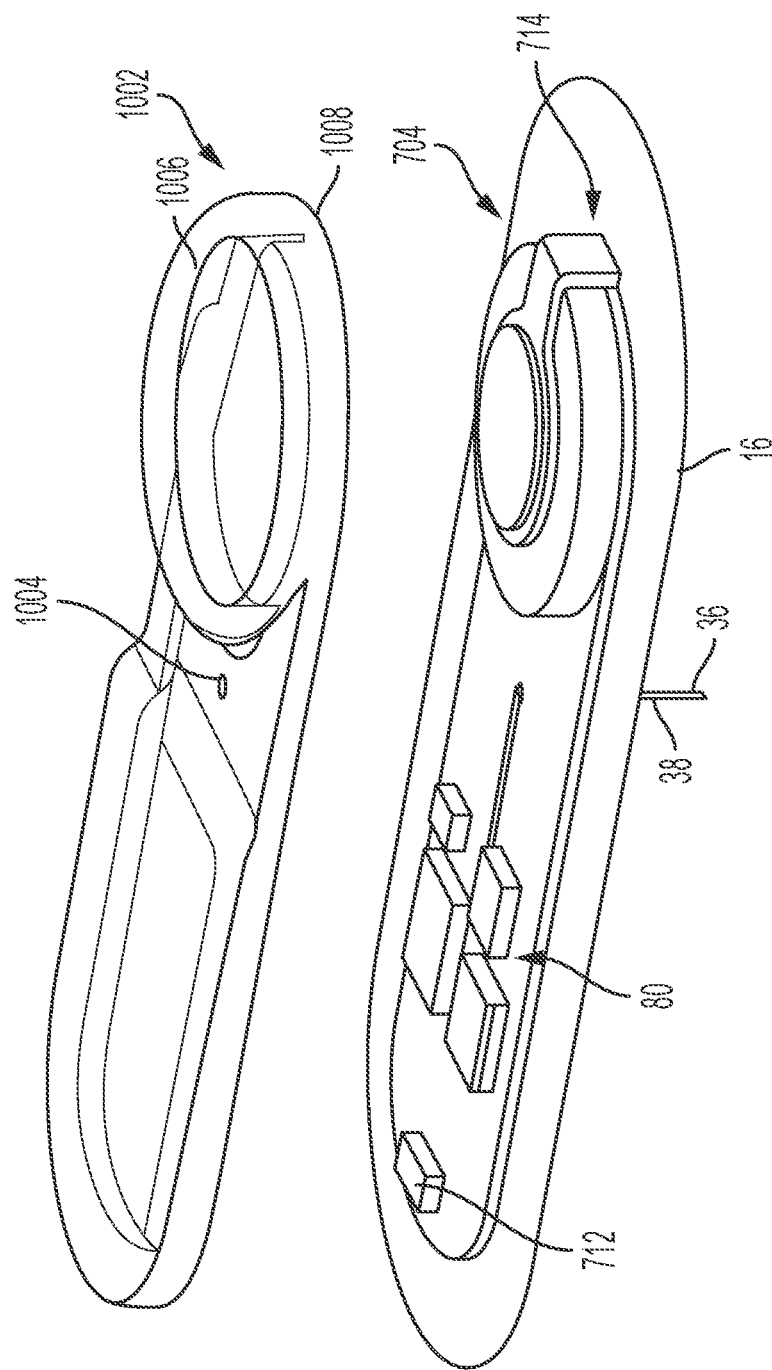
FIG. 51 is a partially exploded view of the physiological characteristic sensor assembly of FIG. 50.

The top housing 1002 is opposite the lower housing 16 and the adhesive patch 18. The top housing 1002 forms a portion of an outermost surface of the physiological characteristic sensor assembly 1000. The top housing 1002 is flexible, and in one example is composed of a biocompatible polymer based material, including, but not limited to, thermoplastic polyurethane. In this example, the top housing 1002 is overmolded onto the electrical subsystem 704 (FIG. 51). The top housing 1002 includes a needle bore 1004 that extends through the top housing 1002 from a first side 1006 to a second side 1008. The needle bore 1004 cooperates with a sensor introducer, such as the sensor introducer 110 discussed with regard to FIGS. 10-19, to couple the physiological characteristic sensor assembly 1000 to the body of the user. As the assembly of the physiological characteristic sensor assembly 1000 is similar to the assembly of the physiological characteristic sensor assembly 700, the assembly of the physiological characteristic sensor assembly 1000 will not be discussed in detail herein. Briefly, with the electrical subsystem 704 assembled, the top housing 1002 is overmolded onto the electrical subsystem 704. The adhesive patch 18 may be coupled to the lower housing 16 for affixing the physiological characteristic sensor assembly 1000 to the skin of the user.

Figure 52:
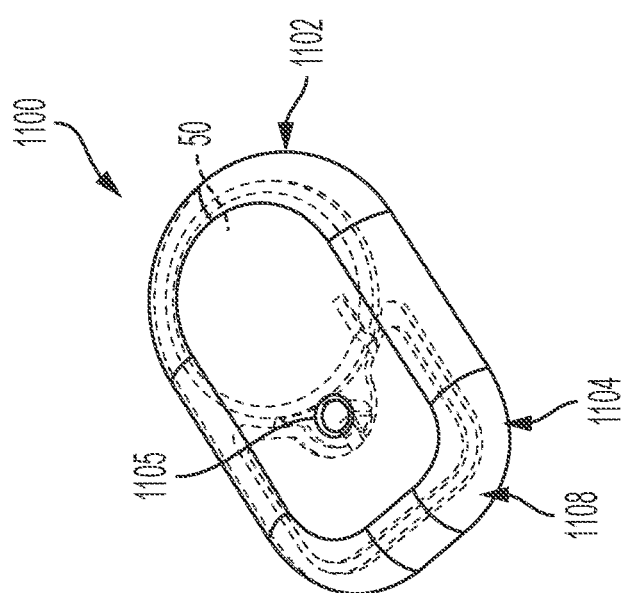
FIG. 52 is a perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 52, a physiological characteristic sensor assembly 1100 is provided in accordance with various embodiments. The physiological characteristic sensor assembly 1100 is flexible, and has a low profile. As the physiological characteristic sensor assembly 1100 includes components that are similar or the same as the physiological characteristic sensor assembly 10 discussed with regard to FIGS. 1-9, the same reference numerals will be used to denote the same components. In one example, the physiological characteristic sensor assembly 1100 includes a first or top housing 1102, an electrical subsystem 1104, a second or lower housing 1106 and the coupling member or adhesive patch 18 (not shown).

The top housing 1102 is opposite the lower housing 1106 and the adhesive patch 18. The top housing 1102 forms a portion of an outermost surface of the physiological characteristic sensor assembly 1100. The top housing 1102 is flexible, and in one example is composed of a biocompatible polymer based material, including, but not limited to, thermoplastic polyurethane or silicone. In this example, the top housing 1102 is formed by molding. The top housing 1102 includes a needle bore 1105 that extends through the top housing 1102 from a first side 1107 to a second side 1108. The needle bore 1105 cooperates with a sensor introducer, such as the sensor introducer 110 discussed with regard to FIGS. 10-19, to couple the physiological characteristic sensor assembly 1100 to the body of the user. The top housing 1102 also defines a recess 1102a and a chamber 1102b that are each sized and shaped to receive a portion of the electrical subsystem 1104.

The electrical subsystem 1104 is contained between the top housing 1102 and the lower housing 1106. In one example, the electrical subsystem 1104 includes the battery 50, the antenna 52, a printed circuit board 1108 and the sensor 38. The battery 50 provides power to the various components of the electrical subsystem 1104. The battery 50 is at least partially received within the recess 1102a of the top housing 1102. The battery 50 is electrically and physically coupled to the printed circuit board 1108. The antenna 52 enables wireless communication between the physiological characteristic sensor assembly 1100 and another device, including, but not limited to, an infusion pump, handheld device (tablet, smart phone, etc.) or other monitoring device. The antenna 52 is electrically and physically coupled to the printed circuit board 1108. The printed circuit board 1108 electrically couples the battery 50 and the antenna 52 to the electrical components 80 (not shown) associated with the physiological characteristic sensor assembly 1100 to enable communication between the battery 50, the antenna 52 and the electrical components 80. The printed circuit board 1108, the antenna 52 and the electrical components 80 are at least partially received within the chamber 1102b of the top housing 1102. In one example, the printed circuit board 1108 is composed of a bio-compatible polymer, including, but not limited to polyimide. In one example, the printed circuit board 1108 includes three portions 1108a-1108c, which are stacked such that the portion 1108b is sandwiched between the portions 1108a, 1108c. In this example, the battery 50 is coupled to the portion 1108b via the pair of contact clips 50a, 50b. The portion 1108b also includes the sensor contact pad 76. The sensor contact pad 76 electrically couples the sensor 38 to the printed circuit board 1108. In this example, each portion 1108a-1108c of the printed circuit board 1108 is curved at a first end 1109 and cooperates with the battery 50 to define a space 1110 to enable the distal segment end 36 of the sensor 38 to pass through. A second end 1111 of the portions 1108a-1108c opposite the first end 1109 may be substantially planar.

The sensor 38 includes the distal segment end 36, the proximal end 84 and the cannulated portion 42 that extends from the distal segment end 36 toward the proximal end 84. The proximal end 84 includes the sensor contacts 86 that electrically couple the sensor 38 to the sensor contact pad 76 on the printed circuit board 1108.

The lower housing 1106 cooperates with the top housing 1102 to enclose the electrical subsystem 1104. The lower housing 1106 is flexible, and in one example is composed of a biocompatible polymer based material, including, but not limited to, thermoplastic polyurethane or silicone. In this example, the lower housing 1106 is formed by molding. The lower housing 1106 includes a sensor bore 1112 that extends through the lower housing 1106 from a first side 1114 to a second side 1116. The sensor bore 1112 enables the distal segment end 36 to pass through the lower housing 1106. The lower housing 1106 also defines a recess 1106a and a chamber 1106b. The recess 1106a of the lower housing 1106 cooperates with the recess 1102a of the top housing 1102 to receive and enclose the battery 50; and the chamber 1106b of the lower housing 1106 cooperates with the chamber 1102b of the top housing 1102 to receive the printed circuit board 1108, the antenna 52 and the electrical components 80.

Figure 54:
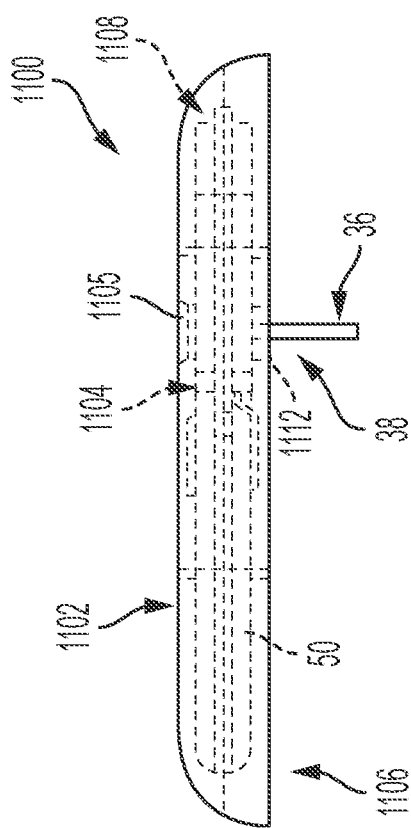
FIG. 54 is a side view of the physiological characteristic sensor assembly of FIG. 52 in accordance with various embodiments.

In one example, in order to assemble the physiological characteristic sensor assembly 1100, the electrical components 80 are electrically and physically coupled to the printed circuit board 1108. The antenna 52 is electrically and physically coupled to the printed circuit board 1108. The sensor 38 is coupled to the printed circuit board 1108 such that the sensor contacts 86 are electrically and physically coupled to the sensor contact pad 76 of the printed circuit board 1108. With the top housing 1102 and the lower housing 1106 molded independently, the assembled electrical subsystem 1104 is sandwiched between the top housing 1102 and the lower housing 1106 such that the needle bore 1105 is coaxially aligned with the cannulated portion 42 of the sensor 38, and the distal segment end 36 of the sensor 38 is received through the sensor bore 1112 of the lower housing 1106 as shown in FIG. 54. The top housing 1102 and the lower housing 1106 are coupled together via heat about the perimeter of the top housing 1102 and the lower housing 1106. In other embodiments, the top housing 1102 and the lower housing 1106 may be coupled together using adhesives, including, but not limited to, epoxy such as cyanoacrylate, ultraviolet light curing adhesives, etc. The physiological characteristic sensor assembly 1100 may then be deployed onto a body of the user, and the user may activate the physiological characteristic sensor assembly 1100 to initiate the monitoring of the BG levels with the sensor 38.

In one example, the physiological characteristic sensor assembly 1100 may include the magnet sensor 85, such that the physiological characteristic sensor assembly 1100 is activated once a magnetic field generated by a magnet coupled to a sensor introducer, such as the sensor introducer 110, is removed. In other embodiments, the physiological characteristic sensor assembly 1100 may include the light sensor 82, such that the physiological characteristic sensor assembly 1100 is activated once an ambient light is observed by the light sensor 82. In still other embodiments, the physiological characteristic sensor assembly 1100 may include the push button 83, such that the physiological characteristic sensor assembly 1100 is activated once the push button 83 is deployed or pressed by a user. In yet another embodiment, the physiological characteristic sensor assembly 1100 may be activated based on a signal or transmission received from another device, such as a signal transmitted by a near-field communication system associated with a remote device. Upon activation, the controller receives the sensor signals from the sensor 38 and transmits or communicates these sensor signals, via the antenna 52, to the remote device, including, but not limited to, an infusion pump, handheld device (tablet, smart phone, etc.) or other monitoring device.

Figure 55:
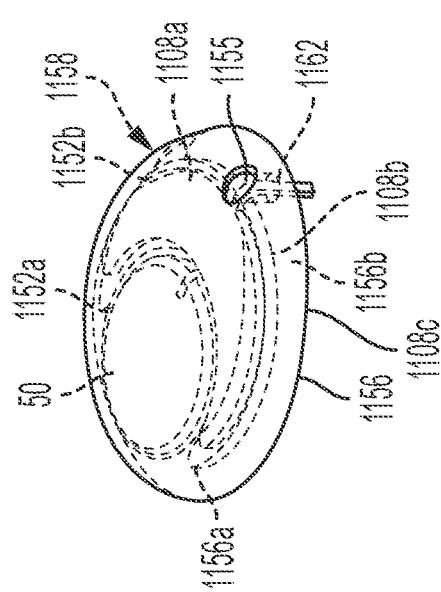
FIG. 55 is a perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 55, a physiological characteristic sensor assembly 1150 is provided in accordance with various embodiments. The physiological characteristic sensor assembly 1150 is flexible, and has a low profile. As the physiological characteristic sensor assembly 1150 includes components that are similar or the same as the physiological characteristic sensor assembly 10 discussed with regard to FIGS. 1-9 and the physiological characteristic sensor assembly 1100 discussed with regard to FIGS. 52-54, the same reference numerals will be used to denote the same components. In one example, the physiological characteristic sensor assembly 1150 includes a first or top housing 1152, an electrical subsystem 1154, a second or lower housing 1156 and the coupling member or adhesive patch 18 (not shown).

The top housing 1152 is opposite the lower housing 1156 and the adhesive patch 18. The top housing 1152 forms a portion of an outermost surface of the physiological characteristic sensor assembly 1150. The top housing 1152 is flexible, and in one example is composed of a biocompatible polymer based material, including, but not limited to, thermoplastic polyurethane or silicone. In this example, the top housing 1152 is formed by molding. The top housing 1152 includes a needle bore 1155 that extends through the top housing 1152 from a first side to a second side. The needle bore 1155 cooperates with a sensor introducer, such as the sensor introducer 110 discussed with regard to FIGS. 10-19, to couple the physiological characteristic sensor assembly 1150 to the body of the user. The top housing 1152 also defines a recess 1152a and a chamber 1152b that are each sized and shaped to receive a portion of the electrical subsystem 1154.

The electrical subsystem 1154 is contained between the top housing 1152 and the lower housing 1156. In one example, the electrical subsystem 1154 includes the battery 50, the antenna 52, a printed circuit board 1158 and the sensor 38. The battery 50 provides power to the various components of the electrical subsystem 1154. The battery 50 is at least partially received within the recess 1152a of the top housing 1152. The battery 50 is electrically and physically coupled to the printed circuit board 1158. The antenna 52 enables wireless communication between the physiological characteristic sensor assembly 1150 and another device, including, but not limited to, an infusion pump, handheld device (tablet, smart phone, etc.) or other monitoring device. The antenna 52 is electrically and physically coupled to the printed circuit board 1158. The printed circuit board 1158 electrically couples the battery 50 and the antenna 52 to the electrical components 80 (not shown) associated with the physiological characteristic sensor assembly 1150 to enable communication between the battery 50, the antenna 52 and the electrical components 80. The printed circuit board 1158, the antenna 52 and the electrical components 80 are at least partially received within the chamber 1152b of the top housing 1152. In one example, the printed circuit board 1158 is composed of a bio-compatible polymer, including, but not limited to polyimide. In one example, the printed circuit board 1108 includes the three portions 1108a-1108c, which are stacked such that the portion 1108b is sandwiched between the portions 1108a, 1108c. In this example, the portions 1108a-1108c of the printed circuit board 1158 have a substantially C-shape or crescent shape, to define the space 1110 for the distal segment end 36 of the sensor 38. The battery 50 is coupled to the portion 1108b via the pair of contact clips 50a, 50b. The portion 1108b also includes the sensor contact pad 76. The sensor contact pad 76 electrically couples the sensor 38 to the printed circuit board 1108.

The sensor 38 includes the distal segment end 36, the proximal end 84 and the cannulated portion 42 that extends from the distal segment end 36 toward the proximal end 84. The proximal end 84 includes the sensor contacts 86 that electrically couple the sensor 38 to the sensor contact pad 76 on the printed circuit board 1158.

The lower housing 1156 cooperates with the top housing 1152 to enclose the electrical subsystem 1154. The lower housing 1156 is flexible, and in one example is composed of a biocompatible polymer based material, including, but not limited to, thermoplastic polyurethane or silicone. In this example, the lower housing 1156 is formed by molding. The lower housing 1156 includes a sensor bore 1162 that extends through the lower housing 1156 from a first side to a second side. The sensor bore 1162 enables the distal segment end 36 to pass through the lower housing 1156. The lower housing 1156 also defines a recess 1156a and a chamber 1156b. The recess 1156a of the lower housing 1156 cooperates with the recess 1152a of the top housing 1152 to receive and enclose the battery 50; and the chamber 1156b of the lower housing 1156 cooperates with the chamber 1152b of the top housing 1152 to receive the printed circuit board 1158, the antenna 52 and the electrical components 80.

Figure 53:
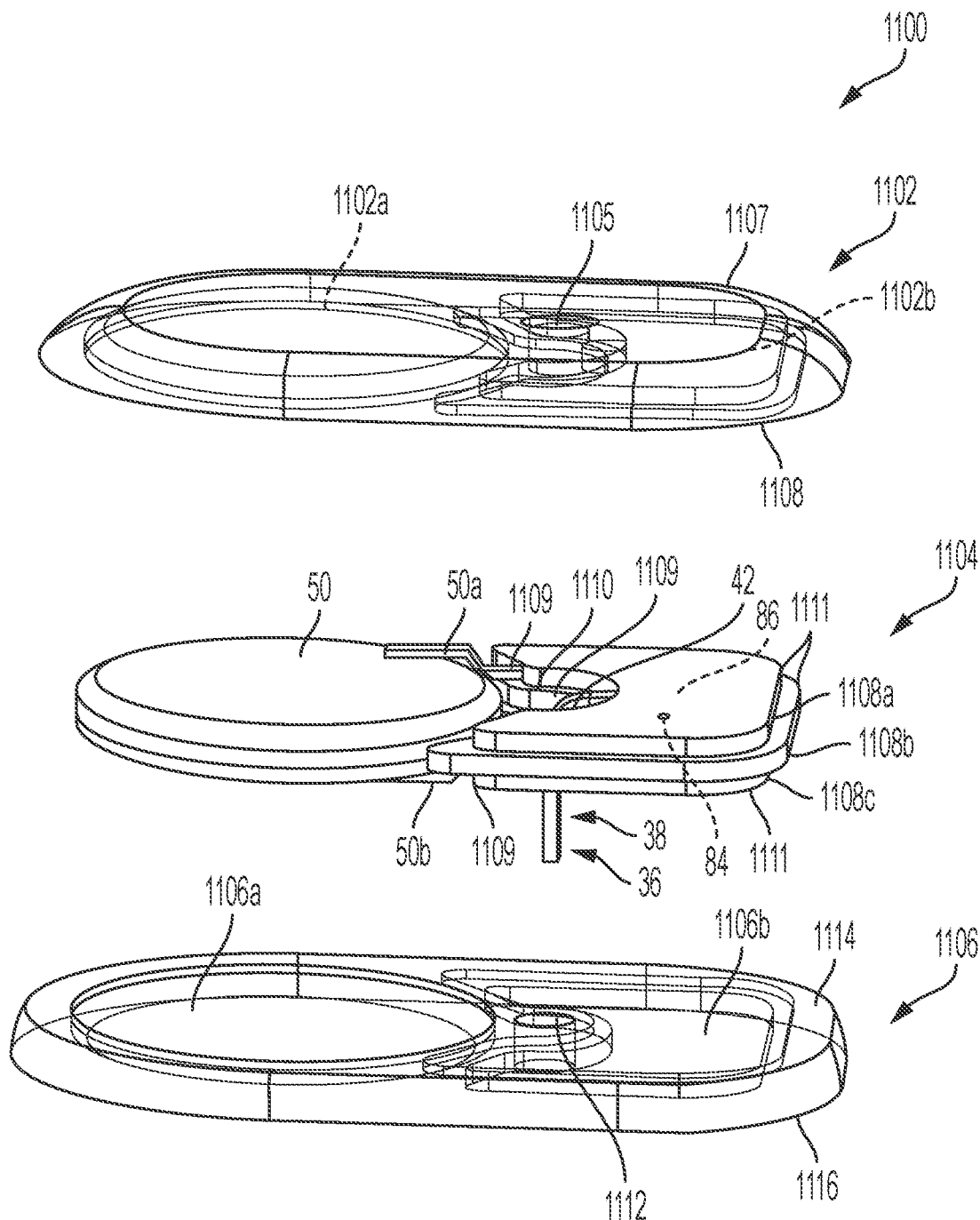
FIG. 53 is a partially exploded view of the physiological characteristic sensor assembly of FIG. 52.

As the assembly of the physiological characteristic sensor assembly 1150 is substantially the same as the assembly of the physiological characteristic sensor assembly 1100, discussed with regard to FIGS. 52-54, the assembly of the physiological characteristic sensor assembly 1150 will not be discussed in detail herein.

Figure 56:
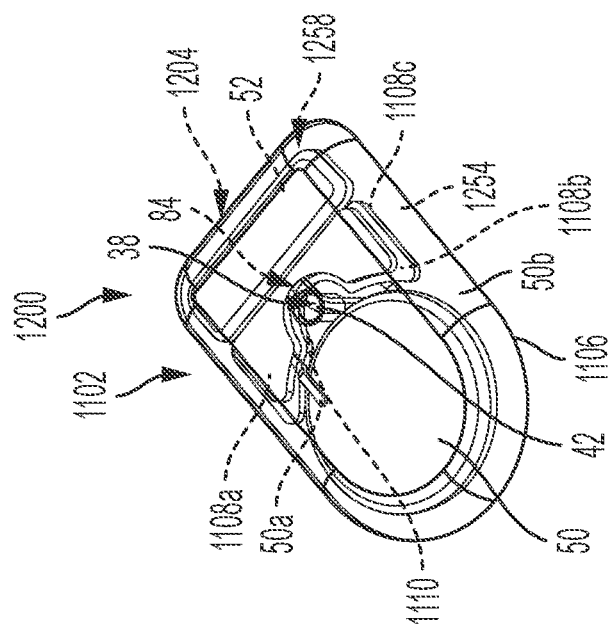
FIG. 56 is a perspective view of another exemplary physiological characteristic sensor assembly in accordance with various embodiments.

It should be noted that in other embodiments, the physiological characteristic sensor assembly 10 may be configured differently to monitor a blood glucose level of a user. With reference to FIG. 56, a physiological characteristic sensor assembly 1200 is provided in accordance with various embodiments. The physiological characteristic sensor assembly 1200 is flexible, and has a low profile. As the physiological characteristic sensor assembly 1200 includes components that are similar or the same as the physiological characteristic sensor assembly 10 discussed with regard to FIGS. 1-9 and the physiological characteristic sensor assembly 1100 discussed with regard to FIGS. 52-54, the same reference numerals will be used to denote the same components. In one example, the physiological characteristic sensor assembly 1200 includes the top housing 1102, an electrical subsystem 1204, the lower housing 1106 and the coupling member or adhesive patch 18 (not shown).

The electrical subsystem 1254 is contained between the top housing 1102 and the lower housing 1106. In one example, the electrical subsystem 1254 includes the battery 50, the antenna 52, a printed circuit board 1258 and the sensor 38. The battery 50 provides power to the various components of the electrical subsystem 1254. The battery 50 is electrically and physically coupled to the printed circuit board 1258. The antenna 52 enables wireless communication between the physiological characteristic sensor assembly 1200 and another device, including, but not limited to, an infusion pump, handheld device (tablet, smart phone, etc.) or other monitoring device. The antenna 52 is electrically and physically coupled to the printed circuit board 1258. In this example, the antenna 52 is spaced apart from the printed circuit board 1258, but electrically and physically coupled to the printed circuit board 1258. The printed circuit board 1258 electrically couples the battery 50 and the antenna 52 to the electrical components 80 (not shown) associated with the physiological characteristic sensor assembly 1200 to enable communication between the battery 50, the antenna 52 and the electrical components 80. In one example, the printed circuit board 1258 is composed of a bio-compatible polymer, including, but not limited to polyimide. In one example, the printed circuit board 1258 includes the three portions 1108*a*-1108*c*. In this example, the battery 50 is coupled to the portion 1108*b* via the pair of clips 50*a*, 50*b*. The portion 1108*b* also includes the sensor contact pad 76. The sensor contact pad 76 electrically couples the sensor 38 to the printed circuit board 1258. In this example, each portion 1108*a*-1108*c* of the printed circuit board 1258 is curved to define the space 1110 to enable the distal segment end 36 of the sensor 38 to pass through.

The sensor 38 includes the distal segment end 36 (not shown), the proximal end 84 and the cannulated portion 42 that extends from the distal segment end 36 toward the proximal end 84. The proximal end 84 includes the sensor contacts 86 (not shown) that electrically couple the sensor 38 to the sensor contact pad 76 on the printed circuit board 1258.

As the assembly of the physiological characteristic sensor assembly 1250 is substantially the same as the assembly of the physiological characteristic sensor assembly 1100, discussed with regard to FIGS. 52-54, the assembly of the physiological characteristic sensor assembly 1200 will not be discussed in detail herein.

It should be noted that in other embodiments, the physiological characteristic sensor assembly 10 may be configured differently to monitor a blood glucose level of a user. With reference to FIG. 57, a physiological characteristic sensor assembly 1300 is provided in accordance with various embodiments. The physiological characteristic sensor assembly 1300 is flexible, and has a low profile. As the physiological characteristic sensor assembly 1300 includes components that are similar or the same as the physiological characteristic sensor assembly 10 discussed with regard to FIGS. 1-9, the physiological characteristic sensor assembly 700 discussed with regard to FIGS. 34-36, the physiological characteristic sensor assembly 750 discussed with regard to FIGS. 37-39 and the physiological characteristic sensor assembly 800 discussed with regard to FIGS. 40-42, the same reference numerals will be used to denote the same components. In one example, the physiological characteristic sensor assembly 1300 includes the top housing 702, an electrical subsystem 1302, the lower housing 16 and the coupling member or adhesive patch 18 (not shown). The lower housing 16, in this embodiment, may comprise a thin film layer, composed of a polymer-based material, including, but not limited to, polyurethane or polyethylene terephthalate.

The top housing 702 is opposite the lower housing 16 and the adhesive patch 18. The top housing 702 includes the needle bore 706 that extends through the top housing 702 from the first side 708 to the second side 710. The electrical subsystem 1302 is contained between the top housing 702 and the lower housing 16. In one example, the electrical subsystem 1302 includes the battery 50, the antenna 52, a flexible printed circuit board 1304, the sensor 38, the conductive film 716, the shim 718 and the rigidizer 756. The battery 50 provides power to the various components of the electrical subsystem 1302. The battery 50 is electrically and physically coupled to the flexible printed circuit board 1304. The antenna 52 enables wireless communication between the physiological characteristic sensor assembly 1300 and another device, including, but not limited to, an infusion pump, handheld device (tablet, smart phone, etc.) or other monitoring device. The antenna 52 is electrically and physically coupled to the flexible printed circuit board 1304.

The flexible printed circuit board 1304 electrically couples the battery 50 and the antenna 52 to the electrical components 80 associated with the physiological characteristic sensor assembly 1300 to enable communication between the battery 50, the antenna 52 and the electrical components 80. In one example, the flexible printed circuit board 1304 is composed of a bio-compatible polymer, including, but not limited to polyimide. A top surface 1306 of the flexible printed circuit board 1304 includes the pair of battery contact pads 66, 67, the sensor contact pad 76 and the one or more contact pads. The battery contact pad 66 is separated by the battery contact pad 67 by a thin portion 1304*a* of the flexible printed circuit board 1304, which enables the battery contact pad 66 to be folded over on top of the battery 50. The sensor contact pad 76 electrically couples the sensor 38 to the flexible printed circuit board 1304. The flexible printed circuit board 1304 also includes a bottom surface 1308 opposite the top surface 1306. The bottom surface 1308 is coupled to the lower housing 16. With reference to FIG. 58, the flexible printed circuit board 1304 includes the sensor bore 79 defined through the top surface 1306 and the bottom surface 1308. The sensor bore 79 enables the needle 256 of the sensor introducer 110 (FIG. 12) to pass through the flexible printed circuit board 1304 and into the sensor 38. In this example, the flexible printed circuit board 1304 includes a wing 1310. The wing 1310 is coupled to the flexible printed circuit board 1304 by a portion 1304*b* of the flexible printed circuit board 1304. With reference back to FIG. 57, wing 1310 includes the antenna 52, which is disposed on a surface 1310*a* of the wing 1310, which is opposite a surface 1310*b* of the wing 1310 (FIG. 58). The wing 1310 defines a needle bore 1310*c* that extends through the wing 1310 to enable the needle 256 of the sensor introducer 110 (FIG. 12) to pass through the wing 1310 and into the sensor 38.

The sensor 38 includes the distal segment end 36, the proximal end 84 and the cannulated portion 42 that extends from the distal segment end 36 toward the proximal end 84. The proximal end 84 includes one or more sensor contacts 86 that electrically couple the sensor 38 to the sensor contact pad 76 on the flexible printed circuit board 1304. The conductive film 716 electrically couples the top housing 702 to the flexible printed circuit board 1304 to enable a user to start-up or initiate the physiological characteristic sensor assembly 1300 to monitor the BG levels of the user. The shim 718 is coupled between the conductive film 716 and the flexible printed circuit board 1304 to electrically separate the conductive film 716 from the flexible printed circuit board 1304. The rigidizer 756 is coupled to the flexible printed circuit board 1304 so as to be positioned over a portion of the sensor 38 and between the battery 50 and the electrical components 80.

Figure 41:
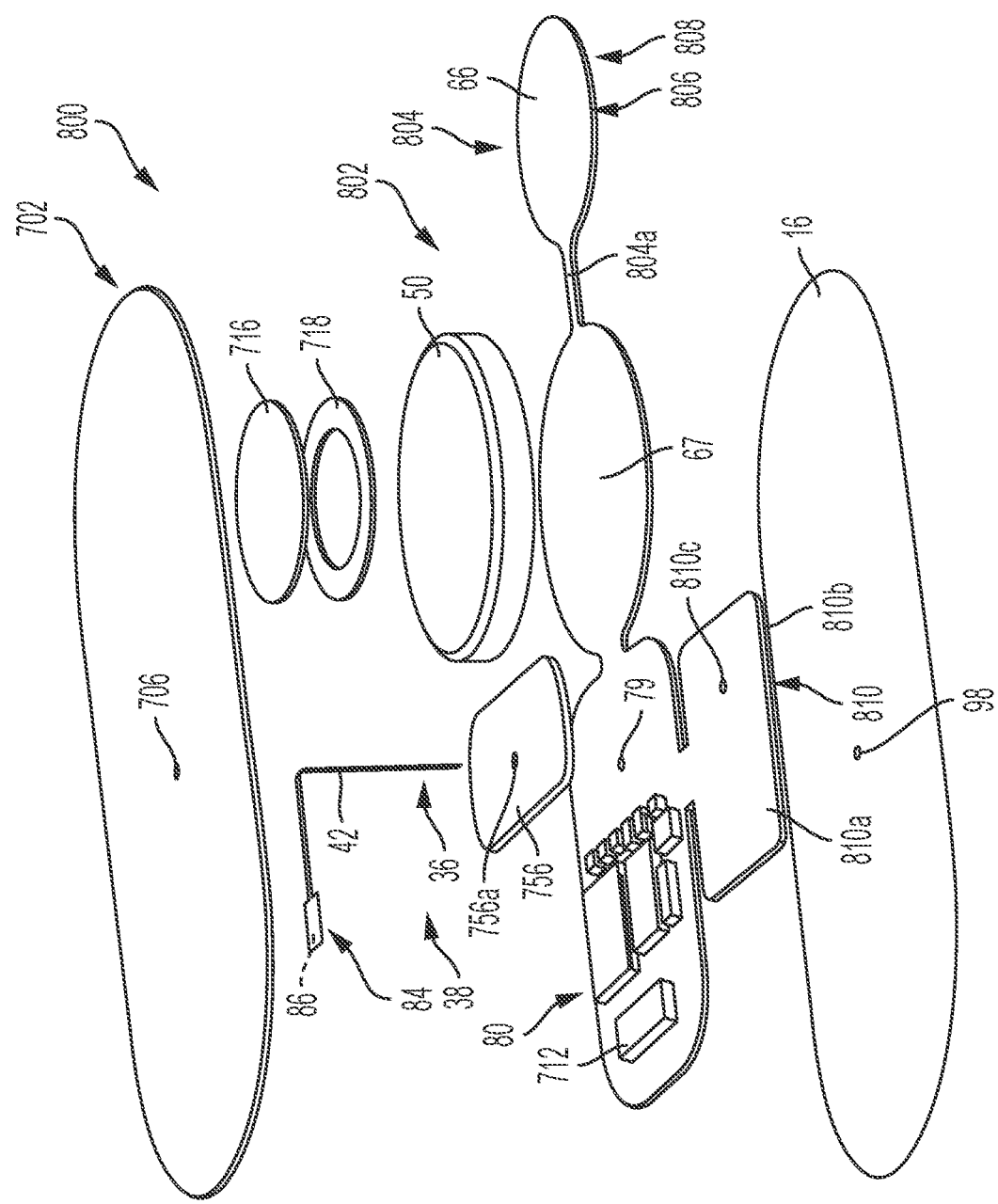
FIG. 41 is an exploded view of the physiological characteristic sensor assembly of FIG. 40.
Figure 42:
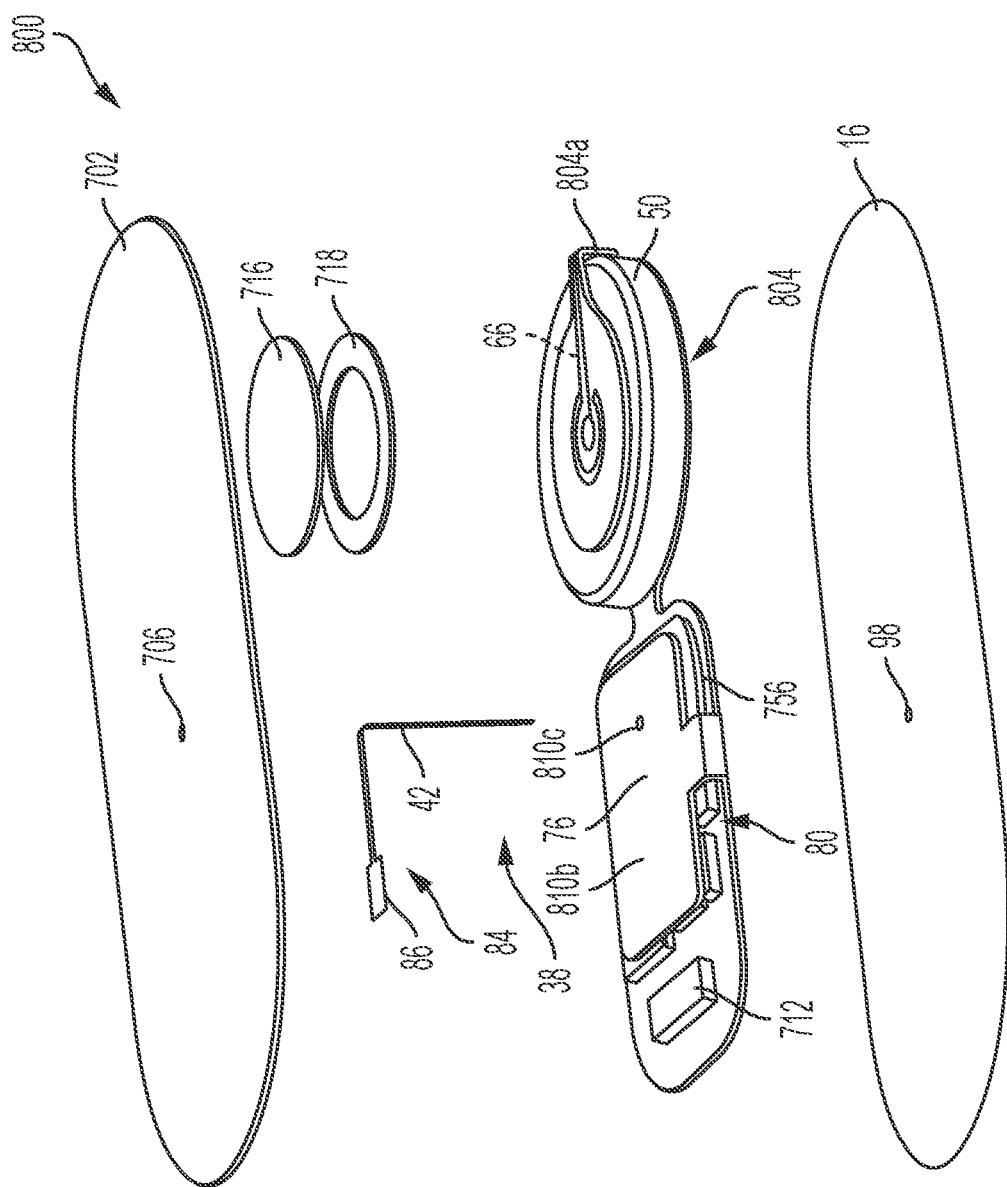
FIG. 42 is a partially exploded view of the physiological characteristic sensor assembly of FIG. 40, which illustrates an action in assembling the physiological characteristic sensor assembly of FIG. 40.

As the assembly of the physiological characteristic sensor assembly 1300 is substantially the same as the assembly of the physiological characteristic sensor assembly 800, discussed with regard to FIGS. 40-42, the assembly of the physiological characteristic sensor assembly 1300 will not be discussed in detail herein.

Figure 59:
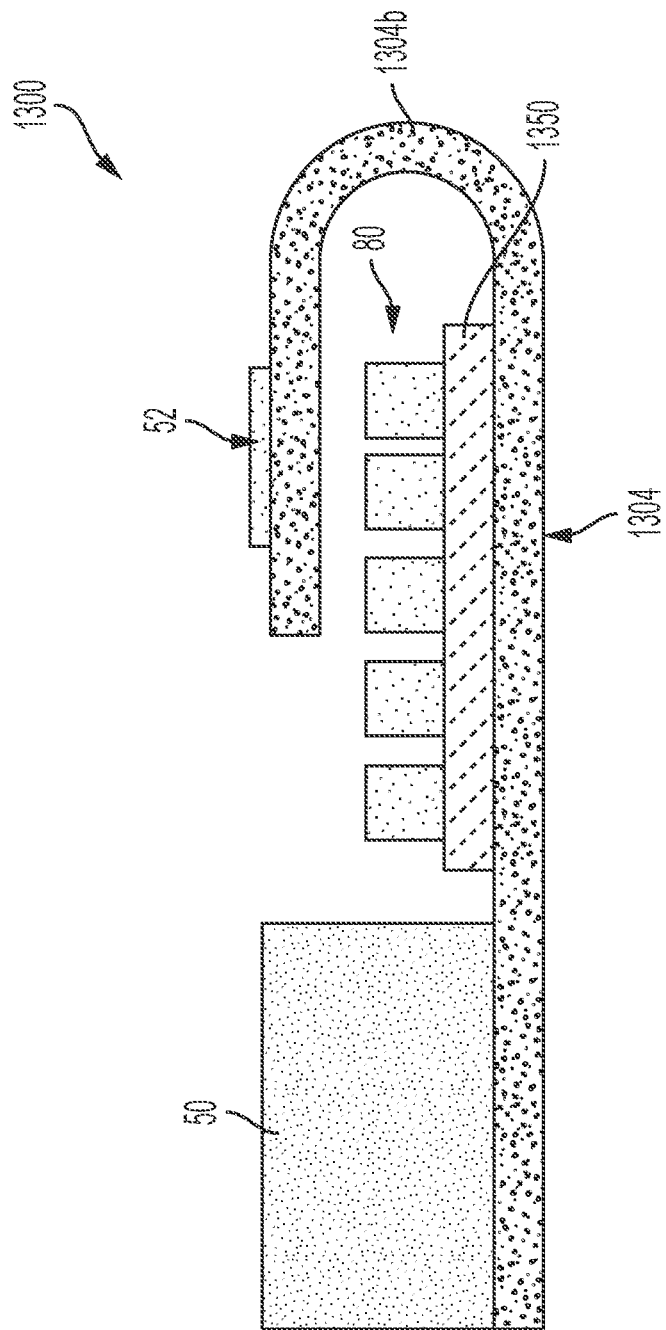
FIG. 59 is a side view of another exemplary physiological characteristic sensor assembly, which illustrates another exemplary arrangement for an electrical subsystem for a physiological characteristic sensor assembly in accordance with various embodiments.

It should be noted that the physiological characteristic sensor assembly 1300 discussed with regard to FIGS. 57 and 58 may be configured differently to monitor a blood glucose level of a user. With reference to FIG. 59, in one example, the physiological characteristic sensor assembly 1300 may include an electrical subsystem having a rigid printed circuit board 1350 physically and electrically coupled to the flexible printed circuit board 1304, via soldering, for example. In the example of FIG. 59, the top housing 702 and the lower housing 16 are not shown for clarity. In this example, the electrical components 80 are physically and electrically coupled to the rigid printed circuit board 1350, which in turn is coupled to the flexible printed circuit board 1304.

Figure 60:
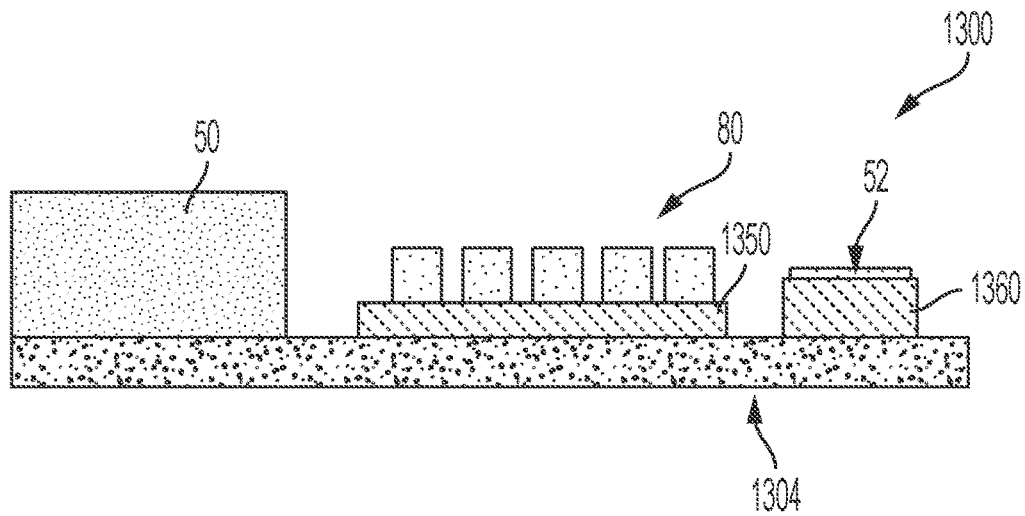
FIG. 60 is a side view of another exemplary physiological characteristic sensor assembly, which illustrates another exemplary arrangement for an electrical subsystem for a physiological characteristic sensor assembly in accordance with various embodiments.

It should be noted that the physiological characteristic sensor assembly 1300 discussed with regard to FIGS. 57-59 may be configured differently to monitor a blood glucose level of a user. With reference to FIG. 60, in one example, the physiological characteristic sensor assembly 1300 may include an electrical subsystem having a second rigid printed circuit board 1360 physically and electrically coupled to the flexible printed circuit board 1304, via soldering, for example. In the example of FIG. 60, the top housing 702 and the lower housing 16 are not shown for clarity. In this example, the antenna 52 is physically and electrically coupled to the second rigid printed circuit board 1360, which in turn is coupled to the flexible printed circuit board 1304. In this example, the antenna 52 is printed on the second rigid printed circuit board 1360.

Figure 61:
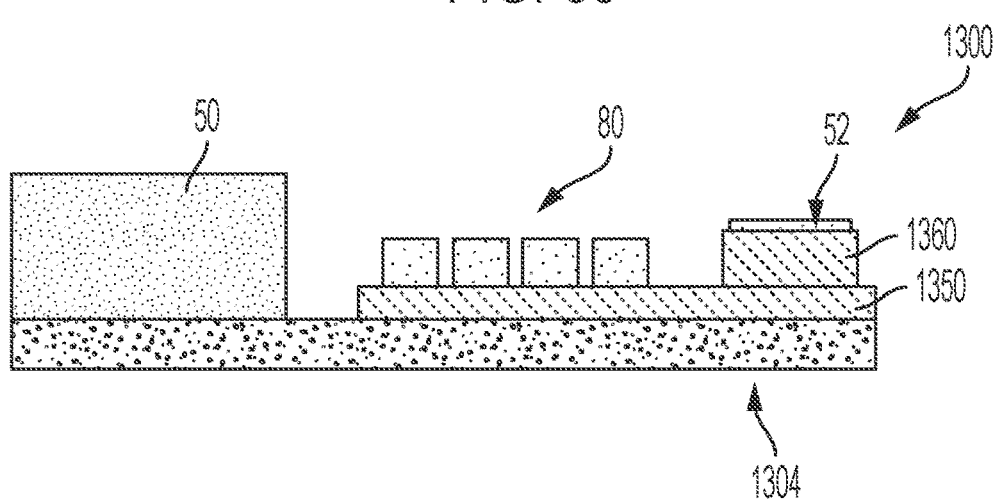
FIG. 61 is a side view of another exemplary physiological characteristic sensor assembly, which illustrates another exemplary arrangement for an electrical subsystem for a physiological characteristic sensor assembly in accordance with various embodiments.

Alternatively, with reference to FIG. 61, in one example, the physiological characteristic sensor assembly 1300 may include an electrical subsystem having the second rigid printed circuit board 1360 physically and electrically coupled to the rigid printed circuit board 1350, via soldering, for example. In the example of FIG. 61, the top housing 702 and the lower housing 16 are not shown for clarity. In this example, the antenna 52 is physically and electrically coupled to the second rigid printed circuit board 1360, which in turn is physically and electrically coupled to the rigid printed circuit board 1350. In one example, the antenna 52 is printed on the second rigid printed circuit board 1360. As a further alternative, with reference to FIG. 61, in one example, the physiological characteristic sensor assembly 1300 may include the second rigid printed circuit board 1360 physically and electrically coupled to the rigid printed circuit board 1350, via soldering, for example. In this example, the antenna 52 is physically and electrically coupled to the second rigid printed circuit board 1360, which in turn is physically and electrically coupled to the rigid printed circuit board 1350. In this example, the antenna 52 is printed on the second rigid printed circuit board 1360.

Figure 62:
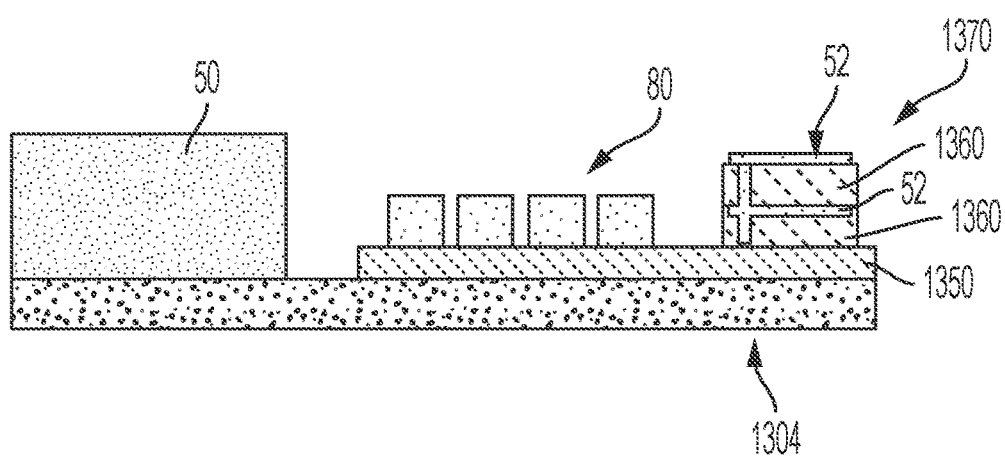
FIG. 62 is a side view of another exemplary physiological characteristic sensor assembly, which illustrates another exemplary arrangement for an electrical subsystem for a physiological characteristic sensor assembly in accordance with various embodiments.

As a further alternative, with reference to FIG. 62, in one example, the physiological characteristic sensor assembly 1300 may include an electrical subsystem having a three dimensional antenna 1370 physically and electrically coupled to the rigid printed circuit board 1350, via soldering, for example. In the example of FIG. 62, the top housing 702 and the lower housing 16 are not shown for clarity. In this example, the three dimensional antenna 1370 include a pair of the antennas 52 coupled to pair of the second rigid printed circuit boards 1360. In one example, a first one of the antennas 52 is physically and electrically coupled to a first one of the second rigid printed circuit board 1360, which in turn is physically and electrically coupled to the rigid printed circuit board 1350. A second one of the antennas 52 is physically and electrically coupled to a second one of the second rigid printed circuit board 1360, which in turn is coupled to the first one of the antennas 52. In this example, the antennas 52 are each printed on the respective one of the second rigid printed circuit boards 1360 and then the antennas 52 are coupled together to work in unison.

In various embodiments, the physiological characteristic sensor assembly 10, 300, 700, 750, 800, 850, 900, 950, 1000, 1100, 1150, 1200, 1250, 1300 may also include a light emitting diode (LED), which may be used to communicate with remote devices, during manufacturing, for example. Further, the physiological characteristic sensor assembly 10, 300, 700, 750, 800, 850, 900, 950, 1000, 1100, 1150, 1200, 1250, 1300 may also include a capacitive sensor on the adhesive patch 18, which is observes whether skin of the user is coupled to the adhesive patch 18 (i.e. observes skin contact) and generates sensor signals based thereon. The sensor signals from the capacitive sensor may be communicated to the controller, which may determine whether the physiological characteristic sensor assembly 10, 300, 700, 750, 800, 850, 900, 950, 1000, 1100, 1150, 1200, 1250, 1300 is in contact with the skin of the user and output a notification, via the respective antenna 52, 712, 966 if the physiological characteristic sensor assembly 10, 300, 700, 750, 800, 850, 900, 950, 1000, 1100, 1150, 1200, 1250, 1300 is no longer in contact with the skin. In other embodiments, the physiological characteristic sensor assembly 10, 300, 700, 750, 800, 850, 900, 950, 1000, 1100, 1150, 1200, 1250, 1300 may also include a 9-axis motion sensor coupled to the respective flexible printed circuit board 54, 330, 552, 602, 714, 754, 804, 854, 914, 968, 1304, for example, which comprises a 3-axis accelerometer, a 3-axis magnetometer, and a 3-axis gyroscope. The use of a 9-axis motion sensor would provide sensor signals to the processor of the physiological characteristic sensor assembly 10, 300, 700, 750, 800, 850, 900, 950, 1000, 1100, 1150, 1200, 1250, 1300 such that the processor may determine position, velocity, acceleration, pitch roll, yaw of the physiological characteristic sensor assembly 10, 300, 700, 750, 800, 850, 900, 950, 1000, 1100, 1150, 1200, 1250, 1300, which enables the processor to further determine, through instructions stored in the memory associated with the processor, sleep, number of steps, running, etc.

Generally, the use of the double sided adhesive layers 58, 60, 334, 336, 338, 340, 560, 562, 564, 565 and the double sided adhesive tape 342 provide waterproofing for the respective physiological characteristic sensor assembly 10, 300 by sealing about the electronics subsystem to inhibit fluids from entering or contacting the electrical subsystem. This prolongs a life of the physiological characteristic sensor assembly 10, 300, while also ensuring the user may shower, swim and engage in other activities without liquids entering into the electrical subsystem. Moreover, it should be noted that each of the physiological characteristic sensor assembly 10, 300, 700, 750, 800, 850, 900, 950, 1000, 1100, 1150, 1200, 1250, 1300 are thin physiological characteristic sensor assembly 10, 300, 700, 750, 800, 850, 900, 950, 1000, 1100, 1150, 1200, 1250, 1300, with an average thickness, measured between the respective top housing 12, 302, 702, 901, 952, 1002, 1102, 1152 and lower housing 16, 903, 1106, 1156 of about 1.0 millimeters to about 2.5 millimeters (mm).

Provided according to various embodiments is a sensor introducer for a physiological characteristic sensor assembly, comprising: a sensor introducer body including: an outer housing that defines an opening to receive the physiological characteristic sensor assembly; an inner housing surrounded by the outer housing; a cradle movable relative to the inner housing from a first position to a second position to deploy the physiological characteristic sensor assembly, the cradle having a cradle flange to receive the physiological characteristic sensor assembly and a cradle body that receives a needle assembly; a lid coupled to the outer housing to enclose the opening that seals the internal space of the sensor introducer from the ambient environment until the user decouple the lid from the outer housing; and wherein the needle assembly is disposed within the cradle body in the third position such that the needle assembly does not extend beyond the cradle flange.

Also provided according to various embodiments is a physiological characteristic sensor system, comprising: a physiological characteristic sensor assembly including a flexible top housing having an alignment feature, a flexible lower housing, an electrical subsystem disposed between the top housing and the lower housing, the electrical subsystem including a physiological characteristic sensor and an adhesive patch having a first adhesive layer opposite a second adhesive layer, the first adhesive layer coupled to the electrical subsystem; and a sensor introducer body including: an outer housing that defines an opening; an inner housing surrounded by the outer housing; a cradle movable relative to the inner housing from a first position to a second position to deploy the physiological characteristic sensor assembly, the cradle having a flange that defines a recess that receives the physiological characteristic sensor assembly and a cradle body that receives a needle shuttle having a needle cradle; a lid coupled to the outer housing to enclose the opening; and a permanent magnet to both couple to a power source of the physiological characteristic sensor assembly to retain the physiological characteristic sensor assembly within the sensor introducer and to turn on the physiological characteristic sensor assembly when the magnet is not in close proximity.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A physiological characteristic sensor system, comprising:
a physiological characteristic sensor assembly including a flexible top housing having a needle port with an alignment recess and a central port, a flexible lower housing, an electrical subsystem disposed between the top housing and the lower housing, the electrical subsystem including a physiological characteristic sensor and a power source, and an adhesive patch having a first adhesive layer opposite a second adhesive layer, the first adhesive layer coupled to the lower housing; and
a sensor introducer body including:
an outer housing that defines an opening;
an inner housing surrounded by the outer housing;
a cradle movable relative to the inner housing from a first position to a second position to deploy the physiological characteristic sensor assembly, the cradle having a flange that defines a recess to receive the physiological characteristic sensor assembly and a cradle body that defines a receptacle to receive a needle shuttle, the flange defining a bore in communication with the recess, with a magnet coupled to the bore, and the physiological characteristic sensor assembly is configured to be received within the recess such that the power source of the physiological characteristic sensor assembly is proximate the magnet, and the magnet is configured to cooperate with the power source to retain the physiological characteristic sensor assembly within the recess;
the needle shuttle received within the receptacle having a needle cradle that defines a needle bore to receive a needle assembly with a needle configured to be coupled to the physiological characteristic sensor, the needle shuttle movable relative to the cradle body, the needle cradle including an alignment projection proximate the needle bore such that the alignment projection is positioned adjacent to a side of the needle assembly, the alignment projection configured to be received within the alignment recess and the needle configured to be received through the central port; and
a lid coupled to the outer housing to enclose the opening.

2. The physiological characteristic sensor system of claim 1, further comprising a collar coupled to a top housing portion of the outer housing and the inner housing, the collar rotatable to enable the cradle to move relative to the inner housing.

3. The physiological characteristic sensor system of claim 1, wherein the alignment projection extends outwardly from an end of the needle cradle to couple to the physiological characteristic sensor assembly, and the lid includes at least one support post that contacts the second adhesive layer to support the physiological characteristic sensor assembly within the sensor introducer body.

4. The physiological characteristic sensor system of claim 1, wherein the outer housing includes a top housing portion and a bottom housing portion, the bottom housing portion defines the opening and the top housing portion includes a projection that extends inwardly toward the bottom housing portion, and the sensor introducer body further comprises a retraction spring disposed between a portion of the needle shuttle and the cradle body, and the retraction spring moves the needle cradle to couple the needle cradle to the projection when the cradle is in a third position.

5. The physiological characteristic sensor system of claim 1, wherein the outer housing includes a top housing portion and a bottom housing portion, the bottom housing portion defines the opening and the top housing portion includes a projection that extends inwardly toward the bottom housing portion and the sensor introducer further comprises a deployment biasing member coupled between the projection and the cradle flange.

6. The physiological characteristic sensor system of claim 1, wherein the cradle body includes at least one locking projection that engages the inner housing to inhibit the movement of the cradle relative to the inner housing in the first position, the at least one locking projection movable relative to the inner housing to enable the cradle to move from the first position to the second position and the outer housing includes an internal flange that contacts the at least one locking projection to disengage the at least one locking projection to enable the cradle to move from the first position to the second position.

7. The physiological characteristic sensor system of claim 1, wherein the electrical subsystem of the physiological characteristic sensor assembly further comprises a magnet sensor that observes a magnetic field of the magnet, and the physiological characteristic sensor of the physiological characteristic sensor assembly is activated based on the magnetic field observed by the magnet sensor.

8. The physiological characteristic sensor assembly of claim 1, wherein the needle port includes a second alignment recess, the alignment recess and the second alignment recess on opposed sides of the central port, the needle cradle includes a second alignment projection proximate the needle bore and the second alignment projection is configured to be received within the second alignment recess.

9. The physiological characteristic sensor system of claim 1, further comprising a first double sided adhesive layer and a second double sided adhesive layer, with the physiological characteristic sensor sandwiched between the first double sided adhesive layer and the second double sided adhesive layer, and the second double sided adhesive layer is coupled to the lower housing.

10. A physiological characteristic sensor system, comprising:
a physiological characteristic sensor assembly including a flexible top housing having a needle port with an alignment recess and a central port, a flexible lower housing, an electrical subsystem disposed between the top housing and the lower housing, the electrical subsystem including a physiological characteristic sensor, a power source and a sensor, and an adhesive patch having a first adhesive layer opposite a second adhesive layer, the first adhesive layer coupled to the lower housing and the second adhesive layer to be coupled to an anatomy; and
a sensor introducer body including:
an outer housing that defines an opening;
an inner housing surrounded by the outer housing;
a cradle movable relative to the inner housing from a first position to a second position to deploy the physiological characteristic sensor assembly, the cradle having a flange that defines a recess to receive the physiological characteristic sensor assembly and a cradle body that defines a receptacle to receive a needle shuttle, the flange defining a bore in communication with the recess, with a magnet coupled to the bore, and the physiological characteristic sensor assembly is configured to be received within the recess such that the power source of the physiological characteristic sensor assembly is proximate the magnet, and the magnet is configured to cooperate with the power source to retain the physiological characteristic sensor assembly within the recess;
the needle shuttle received within the receptacle having a needle cradle that defines a needle bore to receive a needle assembly with a needle configured to be coupled to the physiological characteristic sensor, the needle shuttle movable relative to the cradle body, the needle cradle including an alignment projection proximate the needle bore such that the alignment projection is positioned adjacent to a side of the needle assembly, the alignment projection configured to be received within the alignment recess and the needle configured to be received through the central port; and
a lid coupled to the outer housing to enclose the opening and the lid includes at least one support post that contacts the second adhesive layer to support the physiological characteristic sensor assembly within the sensor introducer body,
wherein the sensor is configured to observe a magnetic field associated with the magnet, and the electrical subsystem is configured to activate the physiological characteristic sensor based on a change in the magnetic field.

11. The physiological characteristic sensor system of claim 10, wherein the physiological characteristic sensor assembly includes a light sensor that is configured to observe an ambient light, and the electrical subsystem is configured to activate the physiological characteristic sensor based on the observation of the ambient light.

12. The physiological characteristic sensor system of claim 10, further comprising a first double sided adhesive layer and a second double sided adhesive layer, with the physiological characteristic sensor sandwiched between the first double sided adhesive layer and the second double sided adhesive layer, and the second double sided adhesive layer is coupled to the lower housing.

13. The physiological characteristic sensor system of claim 10, wherein the cradle body includes at least one locking projection that engages the inner housing to inhibit the movement of the cradle relative to the inner housing in the first position, the at least one locking projection movable relative to the inner housing to enable the cradle to move from the first position to the second position and the outer housing includes an internal flange that contacts the at least one locking projection to disengage the at least one locking projection to enable the cradle to move from the first position to the second position.

\* \* \* \* \*